United States Patent
Gotoh et al.

(10) Patent No.: US 9,315,603 B2
(45) Date of Patent: Apr. 19, 2016

(54) POLYMERIZABLE COMPOUND HAVING OXYGEN-CONTAINING FIVE-MEMBERED RING, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Teizi Satou, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/448,702

(22) Filed: Jul. 31, 2014

(65) Prior Publication Data
US 2015/0034871 A1 Feb. 5, 2015

(30) Foreign Application Priority Data
Jul. 31, 2013 (JP) .................. 2013-158617

(51) Int. Cl.
| | |
|---|---|
| G02F 1/1333 | (2006.01) |
| C08F 122/10 | (2006.01) |
| C09K 19/32 | (2006.01) |
| C07D 307/54 | (2006.01) |
| C07D 407/04 | (2006.01) |
| C07D 405/04 | (2006.01) |
| C07D 271/107 | (2006.01) |
| C09K 19/34 | (2006.01) |
| C09K 19/30 | (2006.01) |
| C09K 19/04 | (2006.01) |

(52) U.S. Cl.
CPC .......... *C08F 122/10* (2013.01); *C07D 271/107* (2013.01); *C07D 307/54* (2013.01); *C07D 405/04* (2013.01); *C07D 407/04* (2013.01); *C09K 19/32* (2013.01); *C09K 19/322* (2013.01); *C09K 19/3405* (2013.01); *C09K 19/3486* (2013.01); *C09K 2019/0411* (2013.01); *C09K 2019/0448* (2013.01); *C09K 2019/0466* (2013.01); *C09K 2019/301* (2013.01); *C09K 2019/3004* (2013.01); *C09K 2019/3009* (2013.01); *C09K 2019/3016* (2013.01); *C09K 2019/3019* (2013.01); *C09K 2019/3027* (2013.01); *C09K 2019/3077* (2013.01); *C09K 2019/323* (2013.01); *C09K 2019/3425* (2013.01)

(58) Field of Classification Search
CPC .. C09K 19/32; C09K 19/322; C09K 19/3405; C09K 19/3486; C09K 2019/3425; C09K 2019/3077; C09K 2019/3004; C09K 2019/3009; C09K 2019/3016; C09K 2019/3019; C09K 2019/301; C09K 2019/0411; C09K 2019/0447; C09K 2019/0466; C09K 2019/3027; C09K 2019/323; C08F 122/10; C07D 307/54; C07D 407/04; C07D 405/04; C07D 271/107
USPC ............... 252/299.01, 299.6, 299.61, 299.62, 252/299.63; 349/182, 183; 526/247, 260, 526/263, 270; 549/370, 414, 500; 546/283.4; 544/333; 548/145
See application file for complete search history.

(56) References Cited

U.S. PATENT DOCUMENTS

| | | | | |
|---|---|---|---|---|
| 6,863,841 | B2 * | 3/2005 | Kirsch ................. | C07D 271/10 252/299.2 |
| 7,968,157 | B2 * | 6/2011 | Takahashi ............ | C07D 271/06 252/299.61 |
| 2003/0143343 | A1 | 7/2003 | Kawabata et al. | |
| 2004/0011996 | A1 | 1/2004 | Klasen-Memmer et al. | |
| 2010/0309423 | A1 | 12/2010 | Bernatz et al. | |
| 2011/0101269 | A1 | 5/2011 | Bernatz et al. | |

FOREIGN PATENT DOCUMENTS

| | | |
|---|---|---|
| JP | 2004-035722 A | 2/2004 |
| JP | 2004-131704 A | 4/2004 |
| JP | 2010-536894 A | 12/2010 |
| JP | 2010-537256 A | 12/2010 |
| WO | 2006093351 A1 | 9/2006 |

* cited by examiner

*Primary Examiner* — Geraldina Visconti
(74) *Attorney, Agent, or Firm* — Hogan Lovells US LLP

(57) ABSTRACT

An object is to provide a polymerizable compound having high polymerization reactivity, a high conversion ratio and high solubility in a liquid crystal composition, a polymerizable composition containing the compound, a liquid crystal composite prepared from the composition, and a liquid crystal display device having the composite. A solution is a polymerizable compound represented by formula (1).

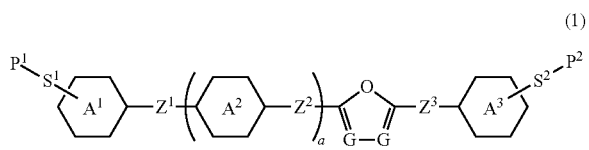

(1)

In the formula, for example, $P^1$ and $P^2$ are —OCO—($CH_3$)C=$CH_2$; $S^1$ and $S^2$ are a single bond; ring $A^1$, ring $A^2$ and ring $A^3$ are 1,4-phenylene; $Z^1$, $Z^2$ and $Z^3$ are a single bond; two of G is —CH= or —N=; and a is 0 or 1.

17 Claims, No Drawings

POLYMERIZABLE COMPOUND HAVING OXYGEN-CONTAINING FIVE-MEMBERED RING, LIQUID CRYSTAL COMPOSITION AND LIQUID CRYSTAL DISPLAY DEVICE

TECHNICAL FIELD

The invention relates to a polymerizable compound, a polymerizable composition containing the polymerizable compound and a liquid crystal composition, a liquid crystal composite prepared from the polymerizable composition, and a liquid crystal display device.

BACKGROUND ART

A liquid crystal display device utilizes optical anisotropy, dielectric anisotropy or the like of liquid crystal molecules in a liquid crystal composition. A classification based on an operating mode of liquid crystal molecules include a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is combined with the liquid crystal composition is known. Specific examples of the mode include a polymer sustained alignment (PSA) mode or a polymer stabilized (PS) mode. In the liquid crystal display device having the mode, the liquid crystal composition to which a polymerizable compound is injected into a display device. The polymerizable compound is polymerized by irradiation with ultraviolet light in a state in which voltage is applied between electrodes, thereby forming the polymer in the liquid crystal composition. The method gives the liquid crystal display device in which response time is shortened and image sticking is improved.

The method can be applied to the liquid crystal display devices having various operating modes, and such modes as PS-TN, PS-IPS, PS-FFS, PSA-VA and PSA-OCB are known. The polymerizable compound used in the device having such a mode is considered to have high capacity to align the liquid crystal molecules, but solubility in the liquid crystal composition is far from high. An attempt has been made for improving the solubility in the liquid crystal composition so far, but an improvement in the solubility tends to cause a decrease in polymerization reactivity. Therefore, desire has been expressed for development of the polymerizable compound having a suitable balance between the solubility and the polymerization reactivity.

CITATION LIST

Patent Literature

Patent literature No. 1: US 2003/0143343 A.
Patent literature No. 2: JP 2004-131704 A.
Patent literature No. 3: JP 2004-35722 A.
Patent literature No. 4: JP 2010-536894 A.
Patent literature No. 5: JP 2010-537256 A.
Patent literature No. 6: WO 2006/093351 A.

SUMMARY OF INVENTION

Technical Problem

A first object of the invention is to provide a polymerizable compound having high polymerization reactivity, a high conversion ratio and high solubility in a liquid crystal composition. A second object is to provide a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. The object is to provide a liquid crystal composite having a proper balance with regard to at least two of physical properties. A third object is to provide a liquid crystal display device having a wide temperature range in which the device can be used, a short response time, a high voltage holding ratio, a low threshold voltage, a large contrast ratio and a long service life.

Solution to Problem

The invention concerns a compound represented by formula (1), a polymerizable composition containing the compound and a liquid crystal composition, a liquid crystal composite prepared from the polymerizable composition, and a liquid crystal display device having the liquid crystal composite.

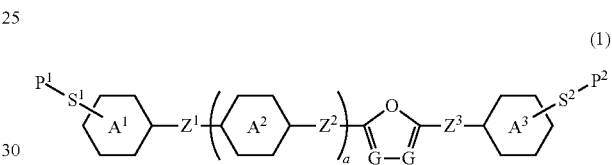

(1)

In formula (1),
$P^1$ and $P^2$ are independently a polymerizable group;
$S^1$ and $S^2$ are independently a single bond or alkylene having 1 to 6 carbons, and in the alkylene, at least one of —$CH_2$— may be replaced by —O—, —COO—, —OCO—, —CH=CH— or —C≡C—;
ring $A^1$, ring $A^2$ and ring $A^3$ are independently cyclohexylene, cyclohexenylene, phenylene, naphthylene, anthracenylene, tetrahydropyranylene, dioxanylene, pyrimidinylene or pyridinylene, and in the groups, at least one of hydrogen may be replaced by halogen, alkyl having 1 to 12 carbons, alkoxy having 1 to 12 carbons, alkyl having 1 to 12 carbons in which at least one of hydrogen is replaced by halogen, or alkoxy having 1 to 12 carbons in which at least one of hydrogen is replaced by halogen, one or two of hydrogen may be replaced by —$S^3$—$P^3$, $P^3$ is defined herein in a manner identical with the definition of $P^1$ or $P^2$, and $S^3$ is defined in a manner identical with the definition of $S^1$ or $S^2$;
two of G are —CH= or —N=;
$Z^1$, $Z^2$ and $Z^3$ are independently a single bond, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—C($CH_3$)=CH—, —C($CH_3$)=C($CH_3$)—COO—, —OCO—C($CH_3$)=C($CH_3$)—, —≡C—, —COCH=CH—, —CH=CHCO—, —C($CH_3$)=C($CH_3$)—, —CH=CH—$CH_2$O—, —O$CH_2$—CH=CH—, —CH=CH—O$CH_2$—, —$CH_2$O—CH=CH— or —CO—; and a is 0 or 1.

The invention also concerns an optical isotropic body, formed by polymerization of the polymerizable composition.
The invention further concerns use of at least one selected from the group of the compound, the polymerizable composition and the liquid crystal composite in a liquid crystal display device.

Advantageous Effects of Invention

A first advantage according to the present invention is a polymerizable compound having high polymerization reactivity, a high conversion ratio and high solubility in a liquid crystal composition. A second advantage is a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. The advantage is the liquid crystal composite having a proper balance with regard to at least two of the physical properties. A third advantage is a liquid crystal display device having a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a non-polymerizable compound having a liquid crystal phase such as a nematic phase and a smectic phase, and a non-polymerizable compound having no liquid crystal phase but mixed for the purpose of adjusting physical properties of a composition, such as a maximum temperature, a minimum temperature, viscosity and dielectric anisotropy. The compounds have a 6-membered ring such as 1,4-cyclohexylene and 1,4-phenylene, and rod-like molecular structure. "Liquid crystal composition" is a mixture of liquid crystal compounds. "Polymerizable compound" is added to the composition for the purpose of forming a polymer. "Polymerizable composition" is a mixture of the polymerizable compound, the liquid crystal composition, an additive and so forth. "Liquid crystal composite" is formed by polymerization of the polymerizable composition. "Liquid crystal display device" is a generic term for a liquid crystal display panel and a liquid crystal display module. The maximum temperature of the nematic phase is a phase transition temperature between the nematic phase and an isotropic phase in the liquid crystal composition, the polymerizable composition or the liquid crystal composite, and may be occasionally abbreviated as the maximum temperature. The minimum temperature of the nematic phase may be occasionally abbreviated as the minimum temperature. "Polymerization reactivity" means a degree of ease when a reactant polymerizes. "Conversion ratio" is a weight ratio of reactant consumed by a chemical reaction to an original reactant.

The liquid crystal composition is prepared by mixing the liquid crystal compounds. A ratio (content) of the liquid crystal compounds is expressed in terms of weight percent (% by weight) based on the weight of the liquid crystal composition. The additive such as an optically active compound, an antioxidant, an ultraviolet light absorber, a light stabilizer, a heat stabilizer and an antifoaming agent is added, when necessary, to the composition. A ratio (content) of the additive is expressed in terms of weight percent (% by weight) based on the weight of the liquid crystal composition in a manner similar to the ratio of the liquid crystal compounds. Weight parts per million (ppm) may be occasionally used. A ratio of a polymerization initiator and a polymerization inhibitor is exceptionally expressed based on the weight of a compound allowing polymerization.

A compound represented by formula (1) may be occasionally abbreviated as compound (1). The abbreviation is also applied to a compound represented by formula (2), or the like. Compound (1) means one compound or two or more compounds represented by formula (1). In ring $A^1$ (or $A^3$) in compound (1), a diagonal line crossing a hexagonal shape means that a bonding position of —$S^1$—$P^1$ (or —$S^2$—$P^2$) on a 6-membered ring can be arbitrarily selected. In formulas (1) to (15), a symbol such as $A^1$, $B^1$ and $C^1$ surrounded by a hexagonal shape corresponds to ring $A^1$, ring $B^1$ and ring $C^1$, respectively. A symbol of $R^{13}$ is used for a plurality of formulas, such as formula (6) and formula (7). In the compounds, two terminal groups represented by two of arbitrary $R^{13}$ may be identical or different. In formula (9), when j is 2, two symbols D1 exist in one formula. In the compound, two rings represented by the two symbols $D^1$ may be identical or different. The above rule is also applied to a symbol such as $Z^{15}$, $C^1$ and $P^3$.

An expression in the context of "at least one of "A" may be replaced by "B"" means that, when the number of "A" is one, a position of "A" is arbitrary, and also when the number of "A" is two or more, positions thereof can be freely selected without restriction. An expression in the context of "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. For example, alkyl in which at least one of —$CH_2$— (or —$CH_2CH_2$—) may be replaced by —O— (or —CH=CH—) includes alkyl, alkenyl, alkoxy, alkoxyalkyl, alkoxyalkenyl and alkenyloxyalkyl. In addition, a case where two of consecutive —$CH_2$— is replaced by —O— to form —O—O— is not preferred. A case where —$CH_2$— of a methyl moiety (—$CH_2$—H) in alkyl or the like is replaced by —O— to form —O—H is not preferred, either.

Then, 2-fluoro-1,4-phenylene means two divalent groups described below. In a chemical formula thereof, fluorine may be leftward (L) or may be rightward (R). The rule is also applied to an asymmetrical divalent ring in tetrahydropyran-2,5-diyl or the like.

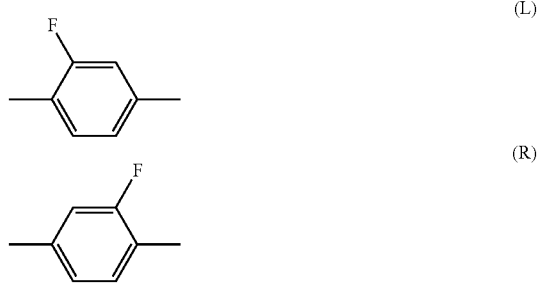

The invention includes the content described in items described below.

Item 1. A compound represented by formula (1):

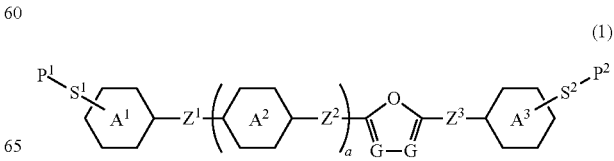

wherein, in formula (1),

P¹ and P² are independently a polymerizable group;

S¹ and S² are independently a single bond or alkylene having 1 to 6 carbons, and in the alkylene, at least one of —CH$_2$— may be replaced by —O—, —COO—, —OCO—, —CH=CH— or —C≡C—;

ring A¹, ring A² and ring A³ are independently cyclohexylene, cyclohexenylene, phenylene, naphthylene, anthracenylene, tetrahydropyranylene, dioxanylene, pyrimidinylene or pyridinylene, and in the groups, at least one of hydrogen may be replaced by halogen, alkyl having 1 to 12 carbons, alkoxy having 1 to 12 carbons, alkyl having 1 to 12 carbons in which at least one of hydrogen is replaced by halogen, or alkoxy having 1 to 12 carbons in which at least one of hydrogen is replaced by halogen, one or two of hydrogen may be replaced by —S³—P³, P³ is defined herein in a manner identical with the definition of P¹ or P², and S³ is defined in a manner identical with the definition of S¹ or S²;

two of G are —CH= or —N=;

Z¹, Z² and Z³ are independently a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH— or —CO—; and a is 0 or 1.

Item 2. The compound according to item 1, wherein, in formula (1) according to item 1, P¹, P² and P³ are a group represented by formula (P-1):

—OCO-(M)C=CH$_2$ (P-1)

wherein, in formula (P-1), M is hydrogen, fluorine, —CH$_3$ or —CF$_3$.

Item 3. The compound according to item 1, represented by any one of formulas (1-1) to (1-6):

(1-1)

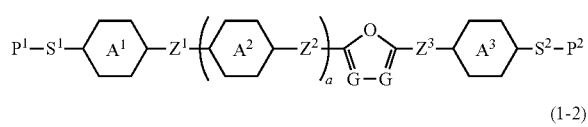
(1-2)

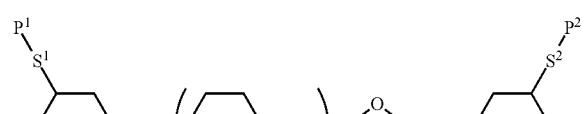
(1-3)

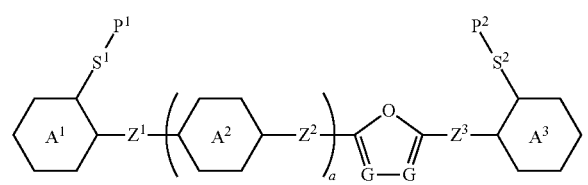

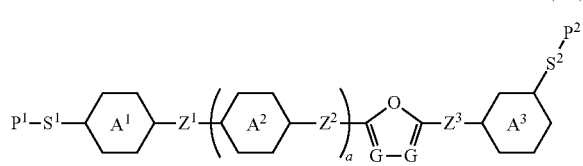
(1-4)

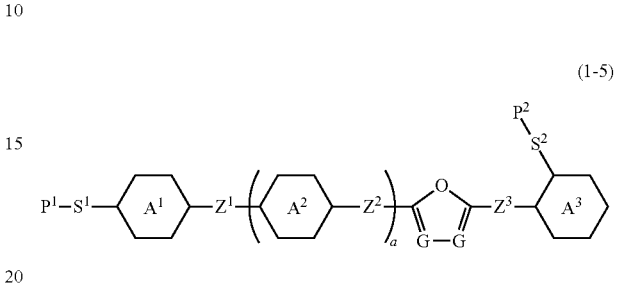
(1-5)

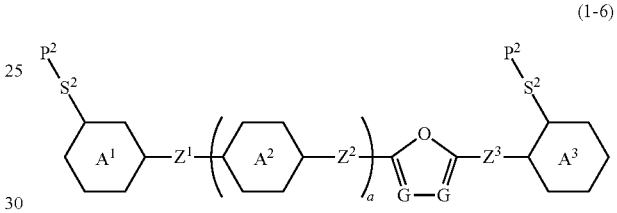
(1-6)

wherein, in formulas (1-1) to (1-6), P¹ and P² are independently a group represented by formula (P-1):

—OCO-(M)C=CH$_2$ (P-1)

wherein, in group (P-1), M is hydrogen, fluorine, —CH$_3$ or —CF$_3$; in formulas (1-1) to (1-6), S¹ and S² are independently a single bond, —CH$_2$O—, —OCH$_2$—, —COO—, —OCO—, —CH=CH—, —CH$_2$CH$_2$O—, —OCH$_2$CH$_2$—, —CH=CHO—, —OCH=CH— or —C≡C—;

ring A¹, ring A² and ring A³ are independently cyclohexylene, cyclohexenylene or phenylene, and in the groups, at least one of hydrogen may be replaced by fluorine, alkyl having 1 to 10 carbons, alkoxy having 1 to 10 carbons, alkyl having 1 to 10 carbons in which at least one of hydrogen is replaced by halogen, or alkoxy having 1 to 10 carbons in which at least one of hydrogen is replaced by halogen, one or two of hydrogen may be replaced by —S³—P³, P³ is defined herein in a manner identical with the definition of P¹ or P², and S³ is defined in a manner identical with the definition of A¹ or S²;

two of G are —CH= or —N=;

Z¹, Z² and Z³ are independently a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH— or —CO—; and a is 0 or 1.

Item 4. The compound according to item 3, wherein a is 0 in formulas (1-1) to (1-6) according to item 3.

Item 5. The compound according to item 1, represented by any of formulas (1-a) to (1-f):

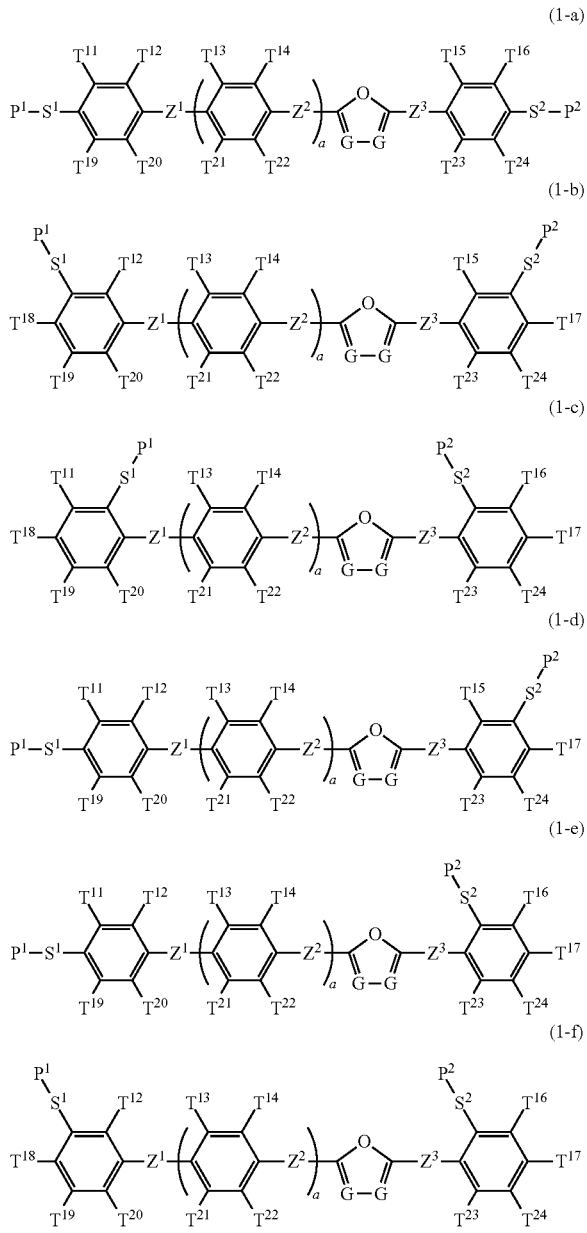

wherein, in formulas (1-a) to (1-f), $P^1$ and $P^2$ are independently a group represented by formula (P-1):

$$-OCO\text{-}(M)C{=}CH_2 \quad (P\text{-}1)$$

wherein, in formula (P-1), M is hydrogen, fluorine, $-CH_3$ or $-CF_3$: in formulas (1-a) to (1-f), $S^1$ and $S^2$ are independently a single bond, $-CH_2O-$, $-OCH_2-$, $-COO-$, $-OCO-$, $-CH{=}CH-$, $-CH_2CH_2O-$, $-OCH_2CH_2-$, $-CH{=}CHO-$, $-OCH{=}CH-$ or $-C{\equiv}C-$;

two of G are $-CH{=}$ or $-N{=}$;

$T^{11}, T^{12}, T^{13}, T^{14}, T^{15}, T^{16}, T^{17}, T^{18}, T^{19}, T^{20}, T^{21}, T^{22}, T^{23}$ and $T^{24}$ are independently hydrogen, fluorine, $-CH_3$, $-CHF_2$ or $-CF_3$;

$Z^1, Z^2$ and $Z^3$ are independently a single bond, $-COO-$, $-OCO-$, $-CH{=}CH-$, $-CH{=}CH-COO-$, $-OCO-CH{=}CH-$, $-C(CH_3){=}CH-COO-$, $-OCO-CH{=}C(CH_3)-$, $-CH{=}C(CH_3)-COO-$, $-OCO-C(CH_3){=}CH-$, $-C(CH_3){=}C(CH_3)-COO-$, $-OCO-C(CH_3){=}C(CH_3)-$, $-C{\equiv}C-$, $-COCH{=}CH-$, $-CH{=}CHCO-$, $-C(CH_3){=}C(CH_3)-$, $-CH{=}CH-CH_2O-$, $-OCH_2-CH{=}CH-$, $-CH{=}CH-OCH_2-$, $-CH_2O-CH{=}CH-$ or $-CO-$; and a is 0 or 1.

Item 6. The compound according to item 5, wherein a is 0 in formulas (1-a) to (1-f) according to item 5.

Item 7. The compound according to item 5, wherein, in formulas (1-a) to (1-f) according to item 5, $P^1$ and $P^2$ are independently $-OCO-CH{=}CH_2$ or $-OCO-(CH_3)C{=}CH_2$; $S^1$ and $S^2$ are independently a single bond, $-CH_2O-$, $-OCH_2-$, $-CH_2CH_2O-$, $-OCH_2CH_2-$, $-CH{=}CHO-$ or $-OCH{=}CH-$; two of G are $-CH{=}$ or $-N{=}$; $T^{11}, T^{12}, T^{13}, T^{14}, T^{15}, T^{16}, T^{17}, T^{18}, T^{19}, T^{20}, T^{21}, T^{22}, T^{23}$ and $T^{24}$ are independently hydrogen or fluorine; $Z^1$ and $Z^3$ are a single bond, $-COO-$, $-OCO-$, $-CH{=}CH-$, $-CH{=}CH-COO-$, $-OCO-CH{=}CH-$, $-C(CH_3){=}CH-COO-$, $-OCO-CH{=}C(CH_3)-$, $-CH{=}C(CH_3)-COO-$, $-OCO-C(CH_3){=}CH-$, $-C(CH_3){=}C(CH_3)-COO-$, $-OCO-C(CH_3){=}C(CH_3)-$ or $-C{\equiv}C-$; and a is 0.

Item 8. The compound according to item 5, wherein, in formula (1-a) according to item 5, $P^1$ and $P^2$ are independently $-OCO-CH{=}CH_2$ or $-OCO-(CH_3)C{=}CH_2$; $S^1$ and $S^2$ are a single bond; two of G are $-CH{=}$ or $-N{=}$; $T^{11}, T^{12}, T^{15}, T^{16}, T^{19}, T^{20}, T^{23}$ and T are hydrogen; $Z^1$ and $Z^3$ are a single bond; and a is 0.

Item 9. A polymerizable composition, containing at least one compound according to any one of items 1 to 8.

Item 10. The polymerizable composition according to item 9, further containing at least one compound selected from the group of compounds represented by formulas (2) to (4):

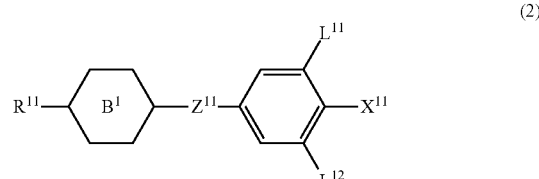

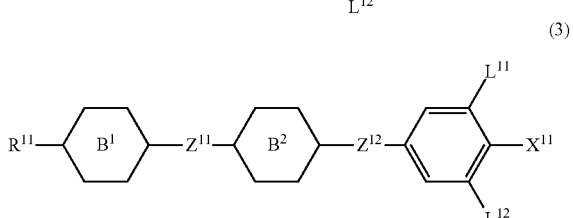

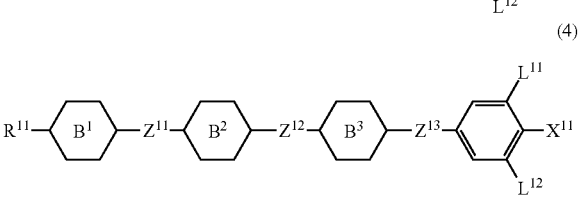

wherein, in formulas (2) to (4), $R^{11}$ is alkyl having 1 to 10 carbons or alkenyl having 2 to 10 carbons, and in the alkyl and the alkenyl, at least one of $-CH_2-$ may be replaced by $-O-$, and in the groups, at least one of hydrogen may be replaced by fluorine;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring B$^1$, ring B$^2$ and ring B$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

Item 11. The polymerizable composition according to item 9, further containing at least one compound selected from the group of compounds represented by formula (5):

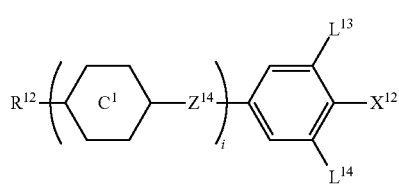
(5)

wherein, in formula (5), $R^{12}$ is alkyl having 1 to 10 carbons or alkenyl having 2 to 10 carbons, and in the alkyl and the alkenyl, at least one of —CH$_2$— may be replaced by —O—, and in the groups, at least one of hydrogen may be replaced by fluorine;

$X^{12}$ is —C≡N or —C≡C—C≡N;

ring C$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

Item 12. The polymerizable composition according to item 9, further containing at least one compound selected from the group of compounds represented by formulas (6) to (12):

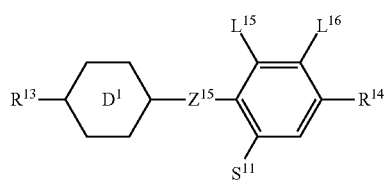
(6)

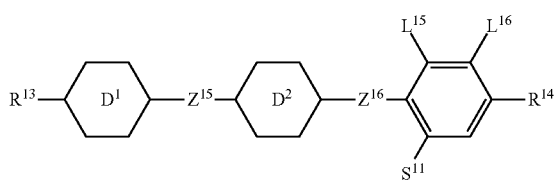
(7)

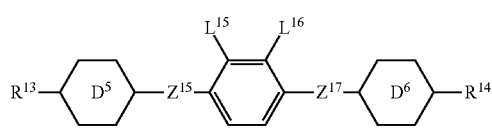
(8)

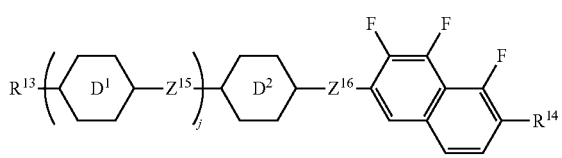
(9)

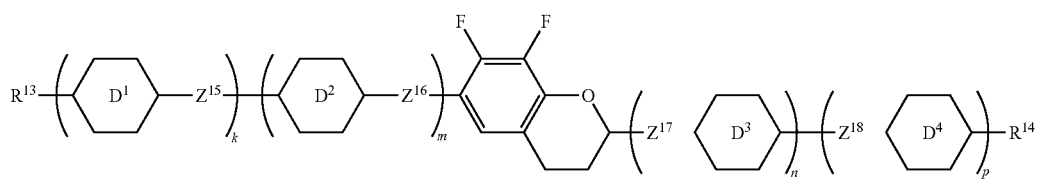
(10)

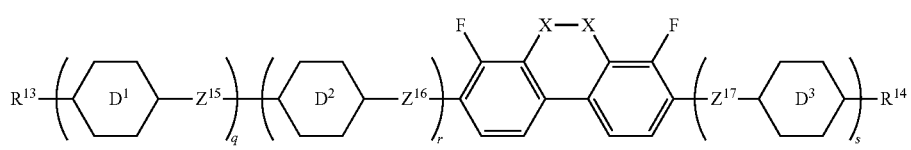
(11)

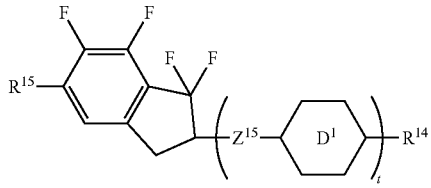

(12)

wherein, in formulas (6) to (12), $R^{13}$ and $R^{14}$ are independently alkyl having 1 to 10 carbons or alkenyl having 2 to 10 carbons, and in the alkyl and the alkenyl, at least one of —$CH_2$— may be replaced by —O—, and in the groups, at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and in the groups, at least one of hydrogen may be replaced by fluorine;

ring $D^1$, ring $D^2$, ring $D^3$ and ring $D^4$ are independent 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or —$CH_3$;

X is —CHF— or —$CF_2$—; and j, k, m, n, p, q, r and s are independently 0 or 1, a sum of k, m, n, and p is 1 or 2, a sum of q, r, and s is 0, 1, 2 or 3, and t is 1, 2 or 3.

Item 13. The polymerizable composition according to any one of items 10 to 12, further containing at least one compound selected from the group of compounds represented by formulas (13) to (15):

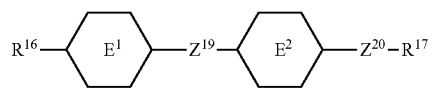

(13)

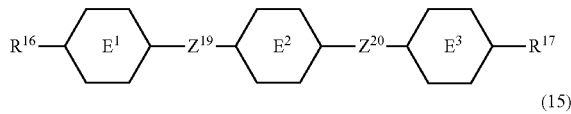

(14)

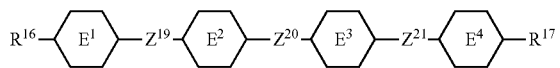

(15)

wherein, in formulas (13) to (15), $R^{16}$ and $R^{17}$ are independently alkyl having 1 to 10 carbons or alkenyl having 2 to 10 carbons, and in the alkyl or the alkenyl, at least one of —$CH_2$— may be replaced by —O—, and in the groups, at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene, or pyrimidine-2,5-diyl; and $Z^{19}$, $Z^{20}$ and $Z^{21}$ are independently a single bond, —$CH_2CH_2$—, —CH=CH—, —C≡C—, or —COO—.

Item 14. A liquid crystal composite, formed by polymerization of the polymerizable composition according to any one of items 9 to 13.

Item 15. An optical isotropic body, formed by polymerization of the polymerizable composition according to any one of items 9 to 13.

Item 16. A liquid crystal display device, including the polymerizable composition according to any one of items 9 to 13, or the liquid crystal composite according to item 14.

Item 17. A liquid crystal display system comprising at least one selected from the group of the compound according to any one of items 1 to 8, the polymerizable composition according to any one of items 9 to 13, and the liquid crystal composite according to item 14, in a liquid crystal display device.

The invention further includes the following items: (1) the polymerizable composition, further containing at least one optically active compound; (2) the polymerizable composition, further containing at least one antioxidant, ultraviolet light absorber and/or antifoaming agent; (3) the polymerizable composition, further containing a polymerizable compound different from the compound represented by formula (1); (4) use of compound (1) in a liquid crystal display device having a PSA mode; (5) use of at least one compound selected from the group of compounds represented by formulas (1-1) to (1-6) in the liquid crystal display device having the PSA mode; (6) use of the polymerizable composition containing at least one of the compounds in the liquid crystal display device having the PSA mode; (7) use of the liquid crystal composite formed by polymerization of the polymerizable composition in the liquid crystal display device having the PSA mode; and (8) use of the compound, the polymerizable composition or the liquid crystal composite in a liquid crystal display device having a PS-TN, PS-IPS, PS-FFS, PSA-VA, or PSA-OCB mode.

The invention further includes the following items: (10) use of the composition containing the compound represented by formula (1) and at least one compound selected from the group of compounds represented by formula (2), (3), or (4) in the liquid crystal display device having the PSA mode; (11) use of the composition containing the compound represented by formula (1) and at least one compound selected from the group of compounds represented by formula (5) in the liquid crystal display device having the PSA mode; (12) use of the composition containing the compound represented by formula (1), and at least one compound selected from the group of compounds represented by formula (6), (7), (8), (9), (10), (11) or (12) in the liquid crystal display device having the PSA mode; and (13) use of the composition containing the compound represented by formula (1), and at least one compound selected from the group of compounds represented by formula (13), (14) or (15) in the liquid crystal display device having the PSA mode.

Compound (1) will be first described, and then description will be made in the order of a synthesis method, a polymerizable composition, a liquid crystal composite and a liquid crystal display device.

1. Compound (1)

The invention concerns polymerizable compound (1) having an oxygen-containing five-membered ring. Compound (1) has a rod-like molecular structure similar to the structure of the liquid crystal compound, and therefore solubility in the liquid crystal composition is high.

Specific preferred examples of the polymerizable groups ($P^1$ to $P^3$), connecting groups ($S^1$ to $S^3$), rings ($A^1$ to $A^3$) or bonding groups ($Z^1$ to $Z^3$) in compound (1) are as described below. The examples are applied also to a subordinate formula of compound (1).

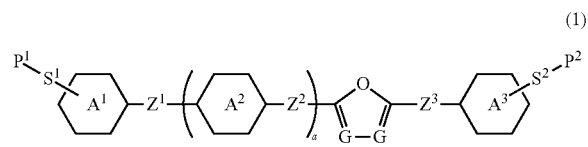

(1)

In formula (1), $P^1$ and $P^2$ are independently a polymerizable group. Examples of the polymerizable group include acryloyloxy, methacryloyloxy, acrylamide, methacrylamide, vinyloxy, vinylcarbonyl, allyloxy, allylcarbonyl, oxiranyl, oxetanyl, 3,4-epoxycyclohexyl or maleimide. In the groups, at least one of hydrogen may be replaced by fluorine, —$CH_3$ or —$CF_3$. Preferred $P^1$ or $P^2$ is —OCO-($M^1$)C=CH($M^2$), wherein, $M^1$ and $M^2$ are independently hydrogen, fluorine, —$CH_3$ or —$CF_3$. Further preferred $P^1$ or $P^2$ is —OCO-(M)C=$CH_2$, wherein, M is hydrogen, fluorine, —$CH_3$ or —$CF_3$. Preferred M is hydrogen, fluorine or —$CH_3$. Further preferred M is hydrogen or —$CH_3$. Particularly preferred $P^1$ or $P^2$ is —OCO—HC=$CH_2$ or —OCO—($CH_3$)C=$CH_2$.

In formula (1), $S^1$ and $S^2$ are independently a single bond or alkylene having 1 to 6 carbons, and in the alkylene, at least one of —$CH_2$— may be replaced by —O—, —COO—, —OCO—, —CH=CH— or —C≡C—. Preferred $S^1$ or $S^2$ is a single bond, —CH=CH—, —C≡C— or alkylene having 1 to 4 carbons, and in the alkylene, one or two of —$CH_2$— may be replaced by —O—, —COO—, —OCO—, —OCOO—, CH=CH— or —C≡C—. Further preferred $S^1$ or $S^2$ is a single bond, —$CH_2CH_2O$—, —$OCH_2CH_2$—, —CH=CHO— or —OCH=CH—. Most preferred $S^1$ or $S^2$ is a single bond.

In formula (1), ring $A^1$, ring $A^2$ and ring $A^3$ are independently cyclohexylene, cyclohexenylene, phenylene, naphthylene, anthracenylene, tetrahydropyranylene, dioxanylene, pyrimidinylene or pyridinylene, and in the groups, at least one of hydrogen may be replaced by halogen, alkyl having 1 to 12 carbons, alkoxy having 1 to 12 carbons, alkyl having 1 to 12 carbons in which at least one of hydrogen is replaced by halogen or alkoxy having 1 to 12 carbons in which at least one of hydrogen is replaced by halogen, one or two of hydrogen may be replaced by —$S^3$—$P^3$, wherein $P^3$ is defined in a manner identical with the definition of $P^1$ or $P^2$, and $S^3$ is defined in a manner identical with the definition of $S^1$ or $S^2$. Preferred examples of alkyl in which at least one of hydrogen is replaced by halogen include alkyl in which at least one of hydrogen is replaced by fluorine or chlorine. Further preferred examples include alkyl in which at least one of hydrogen is replaced by fluorine. Preferred examples of alkoxy in which at least one of hydrogen is replaced by halogen include alkoxy in which at least one of hydrogen is replaced by fluorine or chlorine. Further preferred examples include alkoxy in which at least one of hydrogen is replaced by fluorine.

Preferred ring $A^1$, ring $A^2$ or ring $A^3$ is 1,4-cyclohexylene, 1,4-phenylene, naphthalene-1,4-diyl, naphthalene-1,5-diyl, naphthalene-2,6-diyl, tetrahydropyran-2,5-diyl, 1,3-dioxane-2,5-diyl, pyrimidine-2,5-diyl or pyridine-2,5-diyl, and in the rings, at least one of hydrogen may be replaced by fluorine, chlorine, alkyl having 1 to 3 carbons, or alkyl having 1 to 3 carbons in which at least one of hydrogen is replaced by halogen. Further preferred ring $A^1$, ring $A^2$ or ring $A^3$ is 1,4-cyclohexylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-3-fluoro-1,4-phenylene, 2-methyl-1,4-phenylene, 2-trifluoromethyl-1,4-phenylene, naphthalene-2,6-diyl, tetrahydropyran-2,5-diyl, 1,3-dioxane-2,5-diyl, pyrimidine-2,5-diyl or pyrimidine-2,5-diyl. Particularly preferred ring $A^1$, ring $A^2$ or ring $A^3$ is 1,4-cyclohexylene, 1,4-phenylene, 2-fluoro-1,4-phenylene, 2-methyl-1,4-phenylene or 2-trifluoromethyl-1,4-phenylene. Most preferred ring $A^1$, ring $A^2$ or ring $A^3$ is 1,4-phenylene.

In formula (1), two of G are —CH= or —N=. When two of G are —CH=, the ring is furan-2,5-diyl. When two of G are the ring is 1,3,4-oxadiazole-2,5-diyl. Preferred G is —CH=.

In formula (1), $Z^1$, $Z^2$ and $Z^3$ are independently a single bond, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—C($CH_3$)=CH—, —C($CH_3$)=C($CH_3$)—COO—, —OCO—C($CH_3$)=C($CH_3$)—, —C≡C—, —COCH=CH—, —CH=CHCO—, —C($CH_3$)=C($CH_3$)—, —CH=CH—$CH_2$O—, —$OCH_2$—CH=CH—, —CH=CH—$OCH_2$—, —$CH_2O$—CH=CH— or —CO—. Preferred $Z^1$, $Z^2$ or $Z^3$ is a single bond, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—C($CH_3$)=CH—, —C($CH_3$)=C($CH_3$)—COO—, —OCO—C($CH_3$)=C($CH_3$)—, —C≡C—, —COCH=CH—, —CH=CHCO— or —CO—. Further preferred $Z^1$, $Z^2$ or $Z^3$ is a single bond, —COO—, —OCO—, —CH=CH— or —C≡C—. Particularly preferred $Z^1$, $Z^2$ or $Z^3$ is a single bond. When the bonding groups have —CH=CH—, a configuration thereof may be a cis form or may be a trans form. A preferred configuration is a trans form.

In formula (1), a is 0 or 1. When G is —CH=, preferred a is 0 or 1. Further preferred a is 0. When G is —N=, preferred a is 0.

The polymerizable compound having target physical properties can be obtained by properly selecting a combination of the polymerizable groups ($P^1$ to $P^3$), the connecting groups ($S^1$ to $S^3$), the rings ($A^1$ to $A^3$), the ring (furan or oxadiazole) and the bonding groups ($Z^1$ to $Z^3$) with reference to the preferred examples described above. A case where an element of $S^1$ to be bonded with $P^1$ is oxygen in —$S^1$—$P^1$ is not preferred because a —O—O— bond such as —$CH_2O$—OCO—CH=$CH_2$ is formed. No significant difference in physical properties of the compound is caused, and therefore compound (1) may include a higher amount of isotope such as $^2H$ (deuterium) and $^{13}C$ than an amount of natural abundance.

Preferred examples of compound (1) include compound (1-1) to (1-6). Among the compounds, compound (1-1), (1-2) or (1-3) is preferred. Further preferred examples include compounds (1-a) to (1-f). Among the compounds, compound (1-a), (1-b) or (1-c) is preferred. Among the compounds, compound (1-a) is preferred. Specific examples of compound (1) include compound (No. 1) to compound (No. 243), and the compounds are shown in Examples. Preferred examples among the compounds include compound (No. 1) to compound (No. 14), compound (No. 163), compound (No. 164), compound (No. 167) or compound (No. 168). Further preferred examples include compound (No. 1) or compound (No. 8). Most preferred examples include compound (No. 1).

2. Synthesis Method

A method for synthesizing compound (1) will be described. Compound (1) can be synthesized by properly combining methods in organic synthetic chemistry. A method for introducing an objective terminal group, ring or bonding group into a starting material is described in books such as Houben-Wyle, Methoden der Organischen Chemie (Georg-Thieme Verlag, Stuttgart), Organic Syntheses (John Wily & Sons, Inc.), Organic Reactions (John Wily & Sons, Inc.), Comprehensive Organic Synthesis (Pergamon Press), New Experimental Chemistry Course (Shin Jikken Kagaku Koza in Japanese) (Maruzen Co., Ltd.) or the like.

2-1. Formation of Bonding Group Z

An example of a method for forming bonding groups $Z^1$ to $Z^3$ in compound (1) is as described in a scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1M) correspond to compound (1). In formation of ester, a method for synthesizing a compound having —COO— is shown. A compound having —COO— can also be synthesized by the synthesis method. Any other asymmetrical bonding group can be synthesized in a similar manner.

(1) Formation of a Single Bond

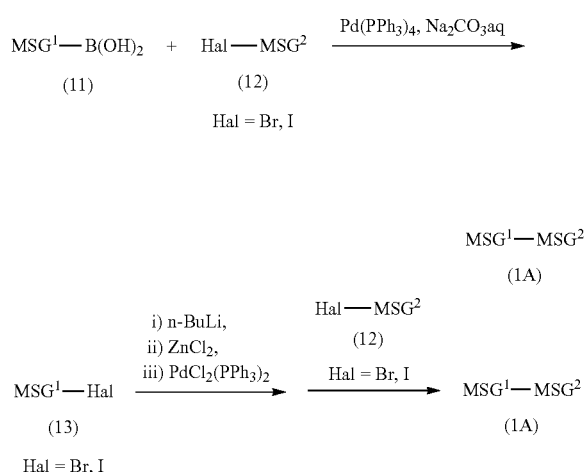

Compound (1A) is prepared by allowing arylboronic acid (11) to react, in the presence of a catalyst such as tetrakis(triphenylphosphine)palladium in an aqueous solution of carbonate, with compound (12) to be prepared according to a publicly known method. Compound (1A) is also prepared by allowing compound (13) to be prepared according to a publicly known method to react with n-butyllithium and subsequently with zinc chloride, and further with compound (12) in the presence of a catalyst such as dichlorobis(triphenylphosphine)palladium.

(2) Formation of —COO—

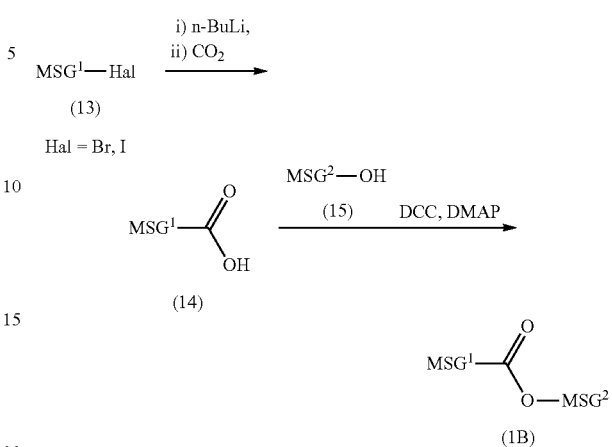

Carboxylic acid (14) is obtained by allowing compound (13) to react with n-butyllithium, and subsequently with carbon dioxide. Compound (1B) is prepared by dehydrating condensation of, in the presence of 1,3-dicyclohexylcarbodiimide (DCC) and N,N-dimethyl-4-aminopyridine (DMAP), compound (14) and phenol (15) to be prepared according to a publicly known method.

(3) Formation of —CH═CH—

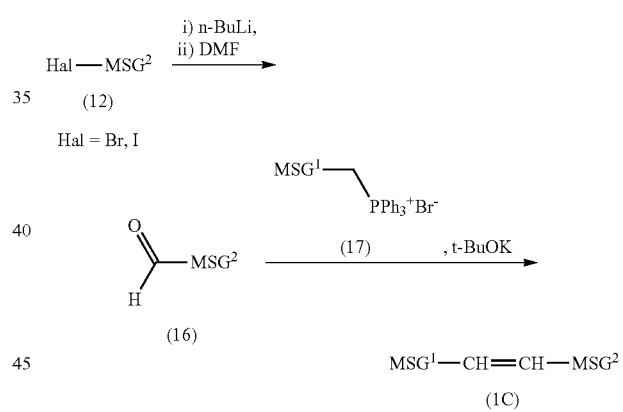

Aldehyde (16) is obtained by treating compound (12) with n-butyllithium and then allowing the treated compound to react with formamide such as N,N-dimethylformamide (DMF). Compound (1C) is prepared by allowing aldehyde (16) to react with phosphorus ylide generated by treating phosphonium salt (17) to be prepared according to a publicly known method with a base such as potassium tert-butoxide. Because a cis isomer is formed depending on reaction conditions, the cis isomer is isomerized into a trans isomer according to a publicly known method, when necessary.

(4) Formation of —CH═CH—COO—

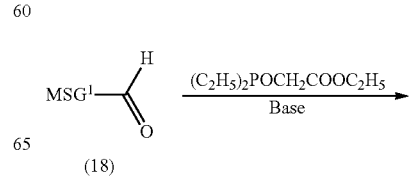

17
-continued

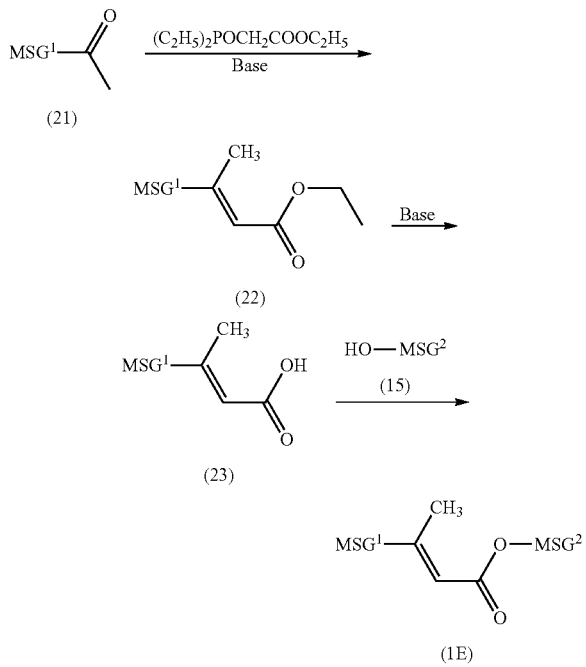

Phosphorus ylide is prepared by allowing a base such as sodium hydride to act on ethyl diethylphosphoacetate, and ester (19) is obtained by allowing the phosphorus ylide to react with aldehyde (18). Carboxylic acid (20) is obtained by hydrolyzing ester (19) in the presence of a base such as sodium hydroxide. Compound (1D) is prepared by dehydrating condensation of the compound and compound (15).

(5) Formation of —C(CH$_3$)=CH—COO—

Phosphorus ylide is prepared by allowing a base such as sodium hydride to act on ethyl diethylphosphoacetate, and ester (22) is obtained by allowing the phosphorus ylide to react with methyl ketone (21). Carboxylic acid (23) is obtained by hydrolyzing ester (22) in the presence of a base such as sodium hydroxide, and then compound (1E) is prepared by dehydrating condensation of the compound and compound (15).

18

(6) Formation of —CH=C(CH$_3$)—COO—

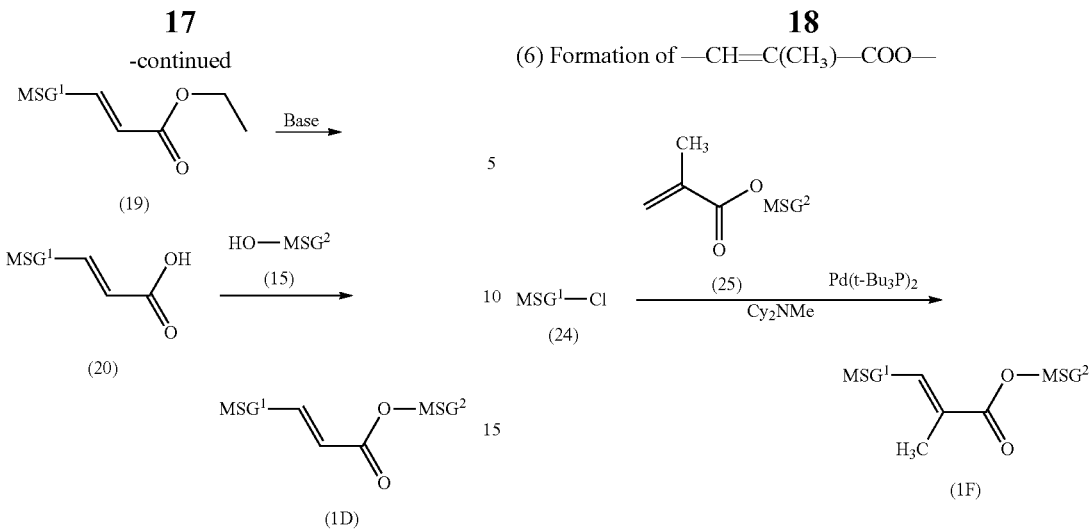

Compound (1F) is prepared by allowing compound (24) prepared according to a publicly known method to react with compound (25) prepared according to a publicly known method in the presence of a base such as N,N-dicyclohexylmethylamine (Cy$_2$NMe), and a catalyst such as bis(tri-tert-butylphosphine)palladium.

(7) Formation of —C(CH$_3$)=C(CH$_3$)—COO—

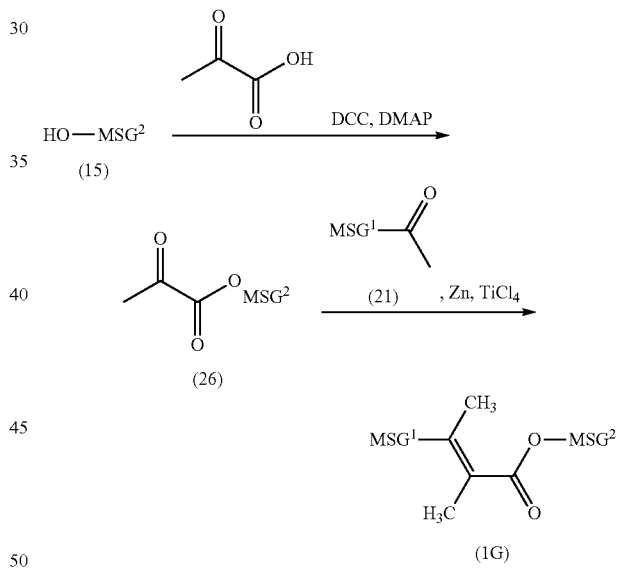

Compound (26) is obtained by dehydrating condensation of compound (15) and pyruvic acid. Compound (1G) is prepared by allowing compound (26) to react with compound (21) in the presence of zinc and titanium tetrachloride.

(8) Formation of —C≡C—

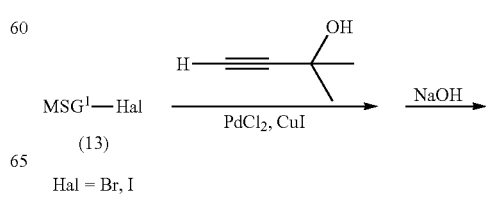

Hal = Br, I

-continued

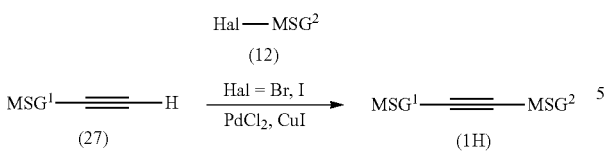

Compound (27) is obtained by allowing 2-methyl-3-butyn-2-ol to react with compound (13) in the presence of a catalyst including dichloropalladium and copper halide, and then deprotecting the resulting product under basic conditions. Compound (1H) is prepared by allowing compound (24) to react with compound (12) in the presence of a catalyst including dichloropalladium and copper halide.

(9) Formation of —COCH=CH—

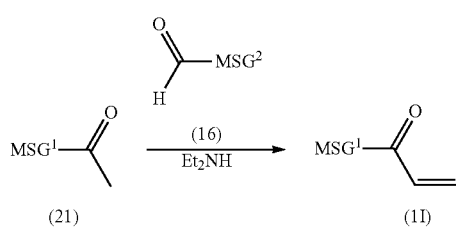

Compound (1I) is prepared by allowing compound (21) to react with compound (16) in the presence of a base such as diethylamine.

(10) Formation of —C(CH$_3$)=C(CH$_3$)—

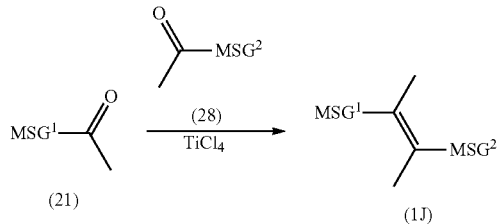

Compound (1J) is prepared by allowing compound (21) to react with compound (28) in the presence of titanium tetrachloride.

(11) Formation of —CH=CH—CH$_2$O—

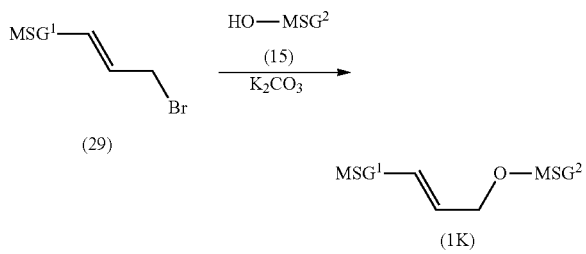

Compound (1K) is prepared by allowing compound (29) to react with compound (15) in the presence of a base such as potassium carbonate.

(12) Formation of —CH=CH—OCH$_2$—

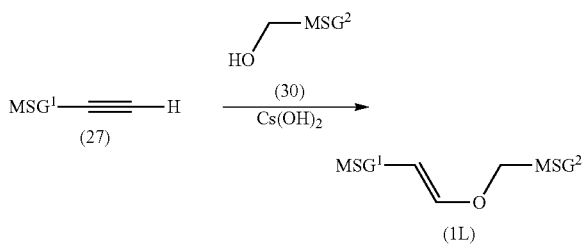

Compound (1L) is prepared by allowing compound (27) to react with compound (30) in the presence of a base such as cesium hydroxide.

(13) Formation of —CO—

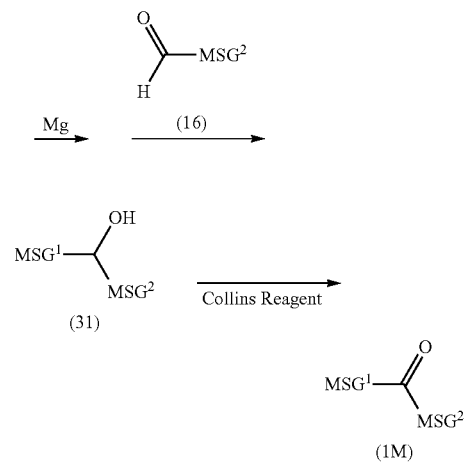

A Grignard reagent is prepared by allowing compound (13) to react with magnesium. Compound (31) is obtained by allowing compound (16) to react with the reagent. Compound (1M) is prepared by allowing the resulting product to react with an oxidizing agent such as a Collins reagent.

2-2. Formation of Connecting Group S

In a compound in which the polymerizable group is —OCO-(M$^1$)C=CH(M$^2$), a method for forming connecting group S will be described in sections (1) to (5).

(1) Single Bond

An example of a method for forming compound (1) in which connecting group S is a single bond is as described in a scheme below. In the scheme, MSG$^1$ is a monovalent organic group having at least one ring. Compounds (1N) to (10) correspond to compound (1).

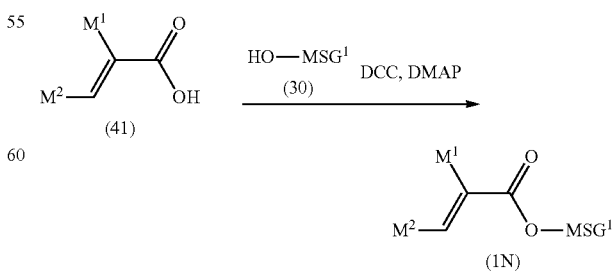

(M$^1$, M$^2$ = H, F, CH$_3$, CF$_3$)

When neither $M^1$ nor $M^2$ is —$CF_3$, when $M^1$ is fluorine and $M^2$ is not —$CF_3$, or when $M^1$ is —$CF_3$ and $M^2$ is not fluorine, carboxylic acid (41) shown in the scheme above is commercially available. Compound (1N) is prepared by allowing dehydrating condensation of carboxylic acid (41) and compound (30) in the presence of DCC and DMAP.

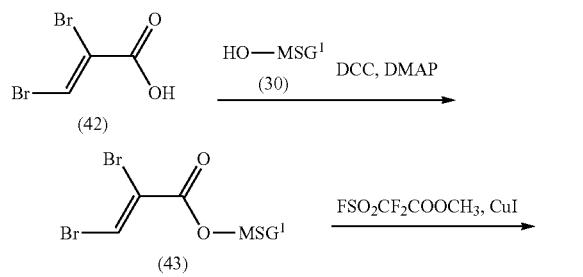

When both $M^1$ and $M^2$ are —$CF_3$, compound (43) is obtained by allowing dehydrating condensation of carboxylic acid (42) and compound (30) in the presence of DCC and DMAP. Compound (1O) is prepared by allowing compound (43) to react with methyl 2,2-difluoro-2-(fluorosulfonyl)acetate in the presence of a catalyst of copper iodide.

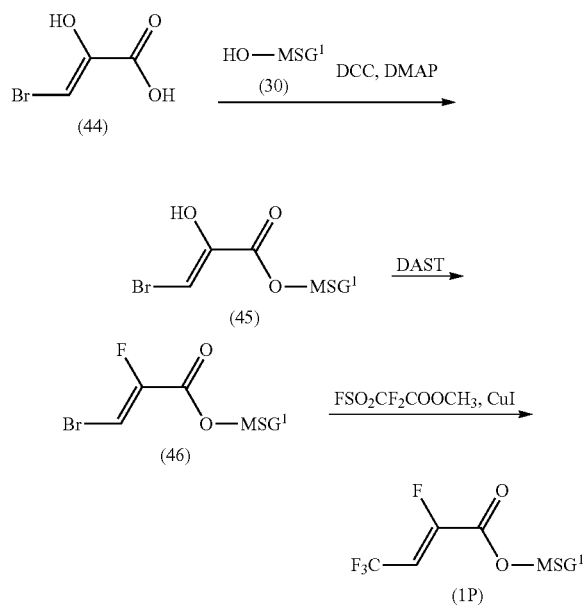

When $M^1$ is fluorine and $M^2$ is —$CF_3$, Compound (45) is obtained by allowing dehydrating condensation of carboxylic acid (44) and compound (30) in the presence of DCC and DMAP. Compound (46) is obtained by fluorinating compound (45) with a fluorinating agent such as DAST. Compound (1P) is prepared by allowing compound (46) to react with methyl 2,2-difluoro-2-(fluorosulfonyl)acetate in the presence of a catalyst of copper iodide.

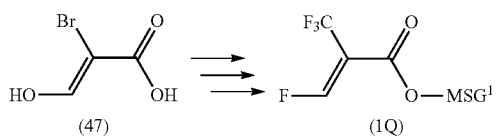

When $M^1$ is —$CF_3$ and $M^2$ is fluorine, compound (1Q) is prepared using carboxylic acid (47) as a starting material, and in accordance with the method described above.

An example of a method for forming a connecting group (S being not a single bond) in compound (1) is as described in a scheme below. In the scheme, $MSG^1$ is a monovalent organic group having at least one ring. Compounds (1R) to (1U) correspond to compound (1).

(2) Formation of —$(CH_2)_g$—O—

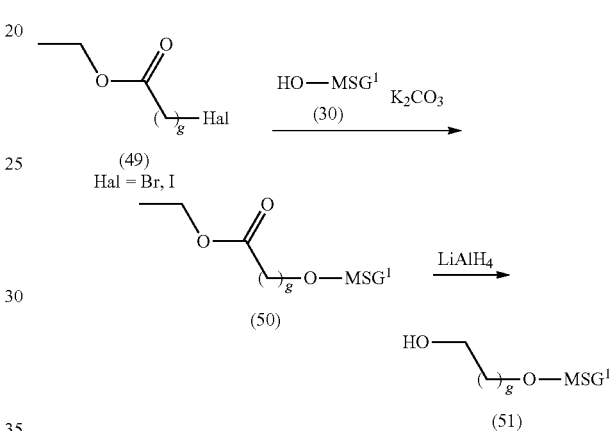

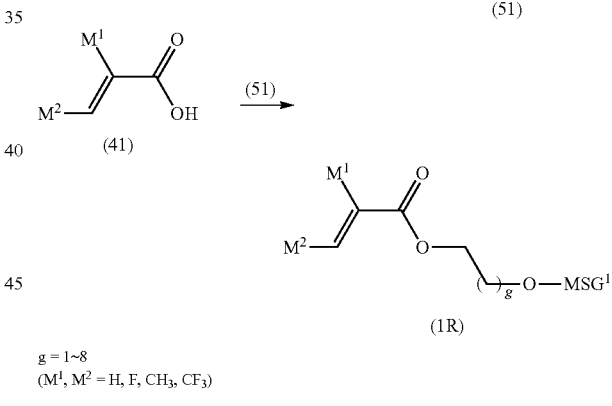

$g = 1\sim8$
($M^1$, $M^2$ = H, F, $CH_3$, $CF_3$)

Compound (50) is obtained by allowing compound (49) prepared according to a publicly known method to react with compound (30) in the presence of potassium carbonate or the like. Compound (51) is obtained by reducing compound (50) with a reducing agent such as lithium hydride aluminum. Compound (1R) is obtained by dehydrating condensation of compound (51) and carboxylic acid (41).

(3) Formation of —$(CH_2)_g$—CH=CH—

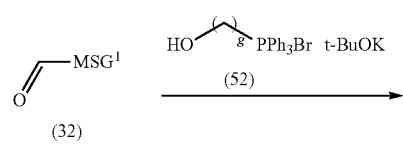

-continued

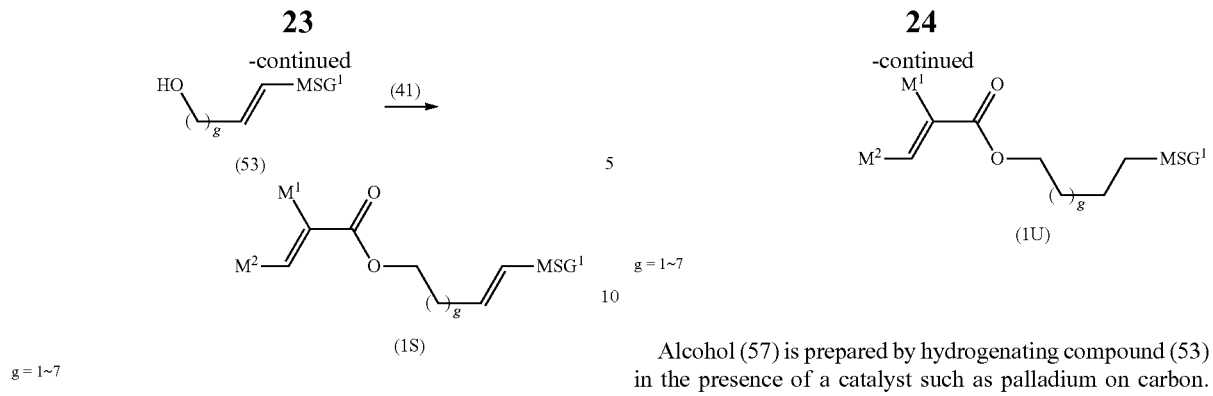

g = 1~7

Compound (53) is obtained by allowing phosphorus ylide generated by treating phosphonium salt (52) prepared according to a publicly known method with a base such as potassium tert-butoxide to react with aldehyde (32). Compound (1S) is obtained by dehydrating condensation of compound (53) and carboxylic acid (41).

(4) Formation of —CH=CH—

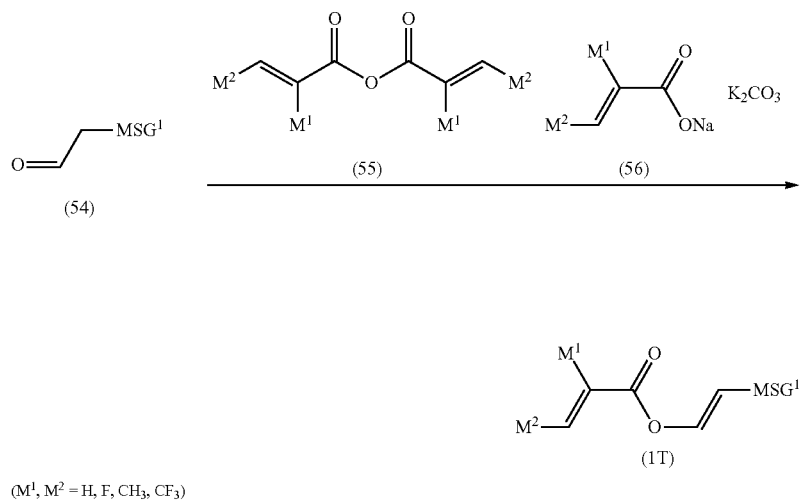

($M^1$, $M^2$ = H, F, $CH_3$, $CF_3$)

Compound (1T) is obtained by allowing reaction of aldehyde (54) prepared according to a publicly known method, acid anhydride (55) and sodium carboxylate (56) in the presence of potassium carbonate or the like.

(5) Formation of —$(CH_2)_g$—$CH_2CH_2$—

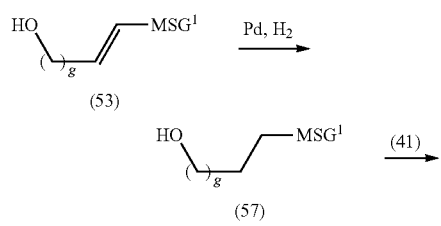

Alcohol (57) is prepared by hydrogenating compound (53) in the presence of a catalyst such as palladium on carbon. Compound (1U) is obtained by allowing dehydrating condensation of the alcohol and carboxylic acid (41).

3. Polymerizable Composition

A polymerizable composition contains at least one of compound (1) as a first component. The component of the composition may include only the first component. A composition may also contain a second component and a third component.

A kind of the second component or the like depends on a kind or application of an objective polymer. The polymerizable composition may further contain any other polymerizable compound different from compound (1) as the second component. Preferred examples of other polymerizable compounds include acrylate, methacrylate, a vinyl compound, a vinyloxy compound, propenyl ether, ethylene oxide (oxirane, oxetane) or vinyl ketone. Further preferred examples include a compound having at least one of acryloyloxy or a compound having at least one of methacryloyloxy. Still further preferred examples include a compound having acryloyloxy and methacryloyloxy.

Additional examples of other polymerizable compounds include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

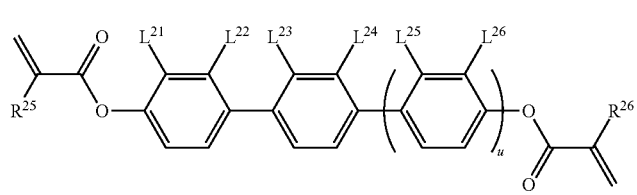
(M-1)
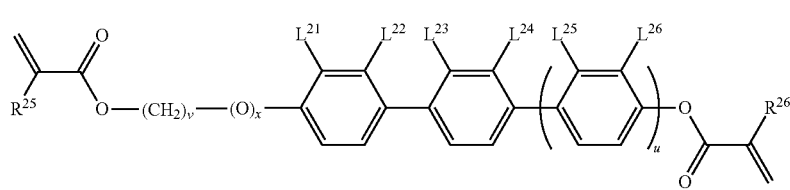
(M-2)
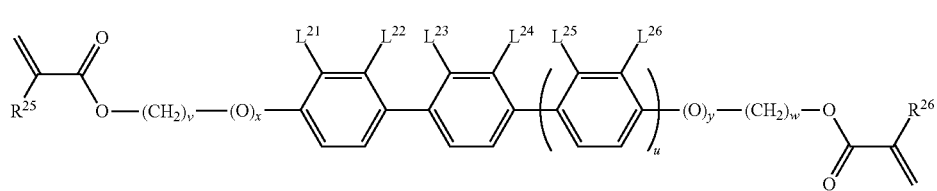
(M-3)
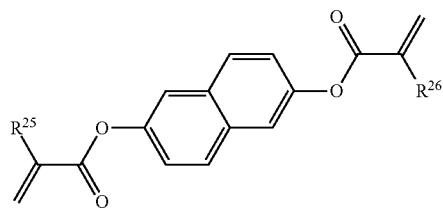
(M-4)
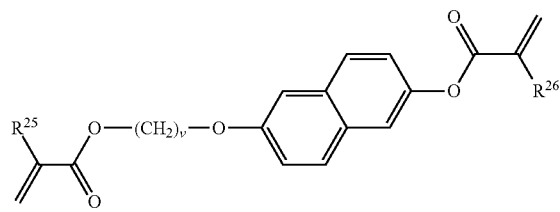
(M-5)
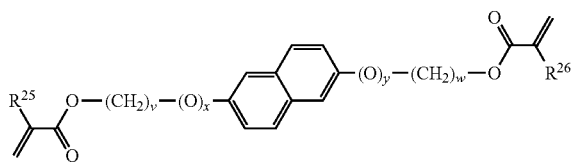
(M-6)
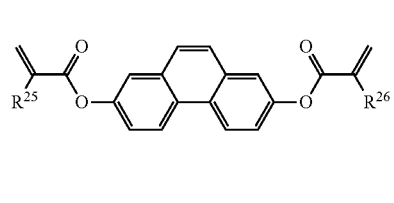
(M-7)
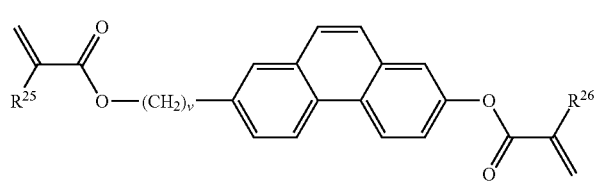
(M-8)
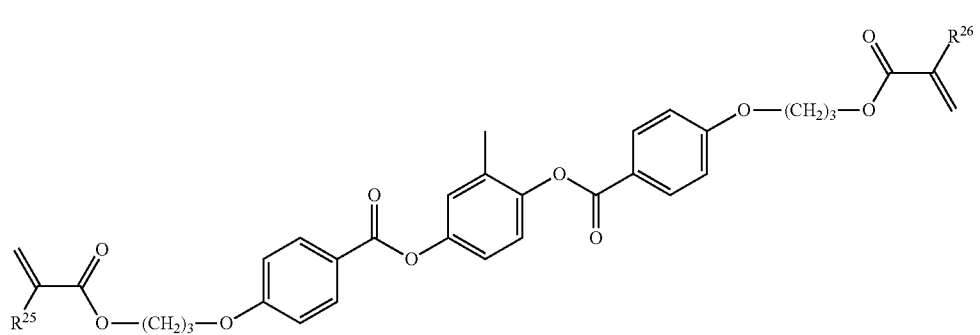
(M-9)

(M-10)

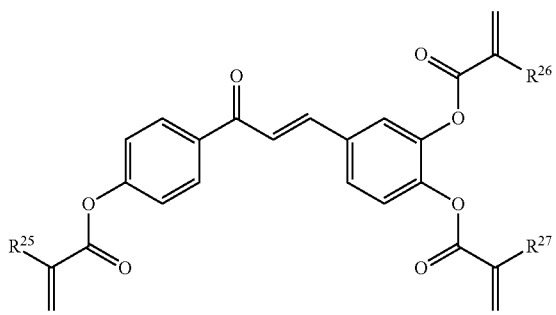

(M-11)

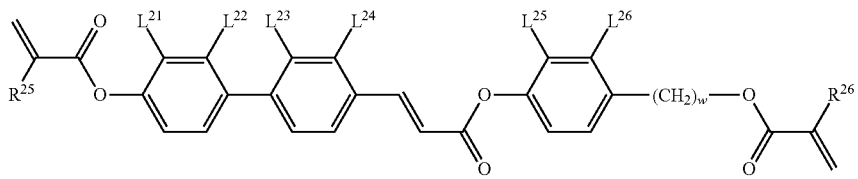

(M-12)

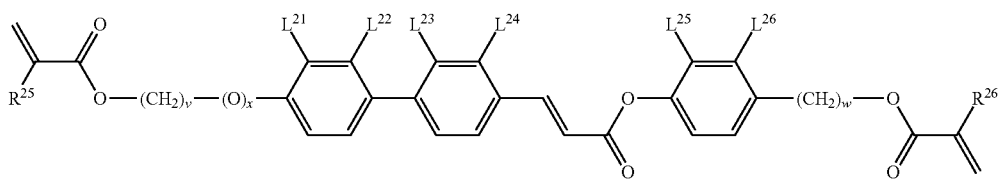

When the second component of the polymerizable composition is the polymerizable compound having the liquid crystal phase, an optical isotropic body is formed by allowing polymerization while controlling alignment of liquid crystal molecules. The optical isotropic body can be used for a phase difference film, a polarized light device, a circularly polarized light device, an elliptically polarized light device, an antireflection film, a selective reflection film, a color compensation film, a viewing angle compensation film, or the like. An additive such as a polymerization initiator may be added to the polymerizable composition for the purpose of adjusting physical properties of the optical isotropic body.

The polymerizable composition may also contain the liquid crystal composition as the second component. When a liquid crystal display device having a mode such as PS-TN, PS-IPS, PS-FFS, PSA-VA and PSA-OCB is targeted, the polymerizable composition contains compound (1) as component A, and preferably, further contains a compound selected from component B, C, D or E shown below. Component B includes compounds (2) to (4). Component C includes compound (5). Component D includes compounds (6) to (12). Component E includes compounds (13) to (15). Upon preparing such a polymerizable composition, component B, C, D or E is preferably selected in taking positive or negative dielectric anisotropy, magnitude of dielectric anisotropy, or the like into consideration. The polymerizable composition prepared by properly selecting the component has a high maximum temperature, a low minimum temperature, small viscosity, suitable (large or small) optical anisotropy, large positive or negative dielectric anisotropy and a suitable (large or small) elastic constant.

In the polymerizable composition containing the liquid crystal composition, an amount of addition of compound (1), namely, compound A is in the range from approximately 0.05% by weight to approximately 20% by weight based on the liquid crystal composition. A further preferred amount of addition is in the range from approximately 0.1% by weight to approximately 10% by weight. A further preferred amount of addition is in the range from approximately 0.2% by weight to approximately 1% by weight. At least one of other polymerizable compounds different from compound (1) may be further added thereto. In the above case, an amount of addition of compound (1) and any other polymerizable compound in total is preferably within the range described above. Physical properties of the polymer to be formed can be adjusted by properly selecting any other polymerizable compound. Examples of other polymerizable compounds include acrylate and methacrylate, as previously described. The examples also include compounds (M-1) to (M-12).

Component B is a compound having a halogen-containing or fluorine-containing group at a right terminal. Specific preferred examples of component B include compounds (2-1) to (2-16), compounds (3-1) to (3-113) and compounds (4-1) to (4-57).

(2-1)

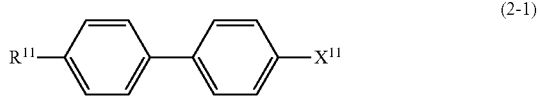

(2-2)

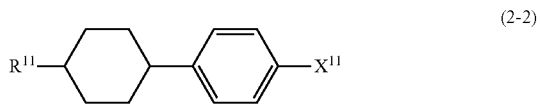

(2-3)

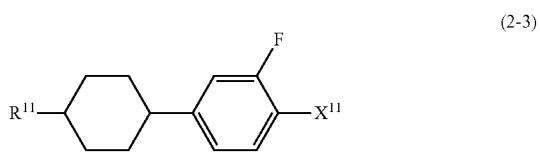

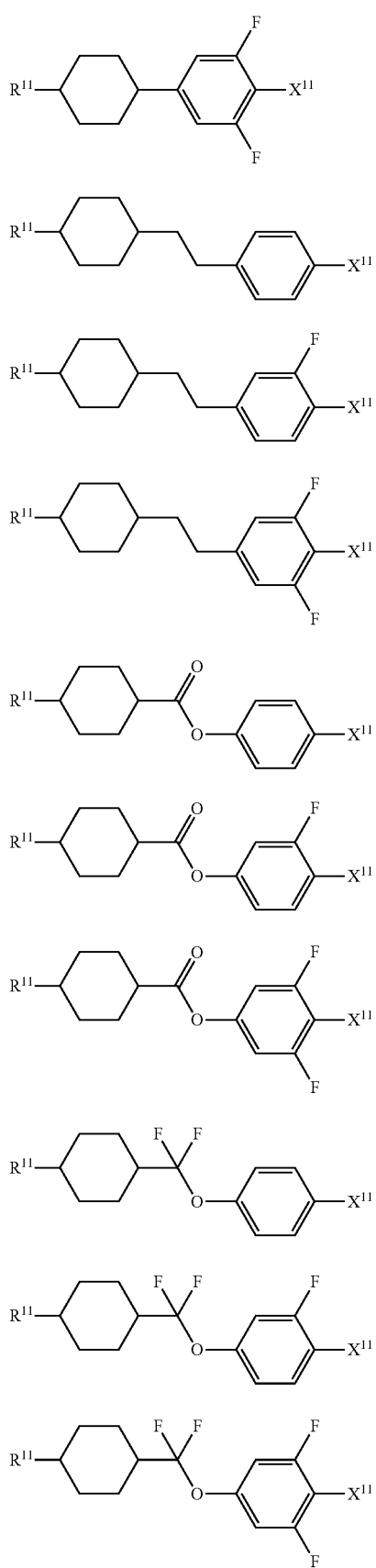
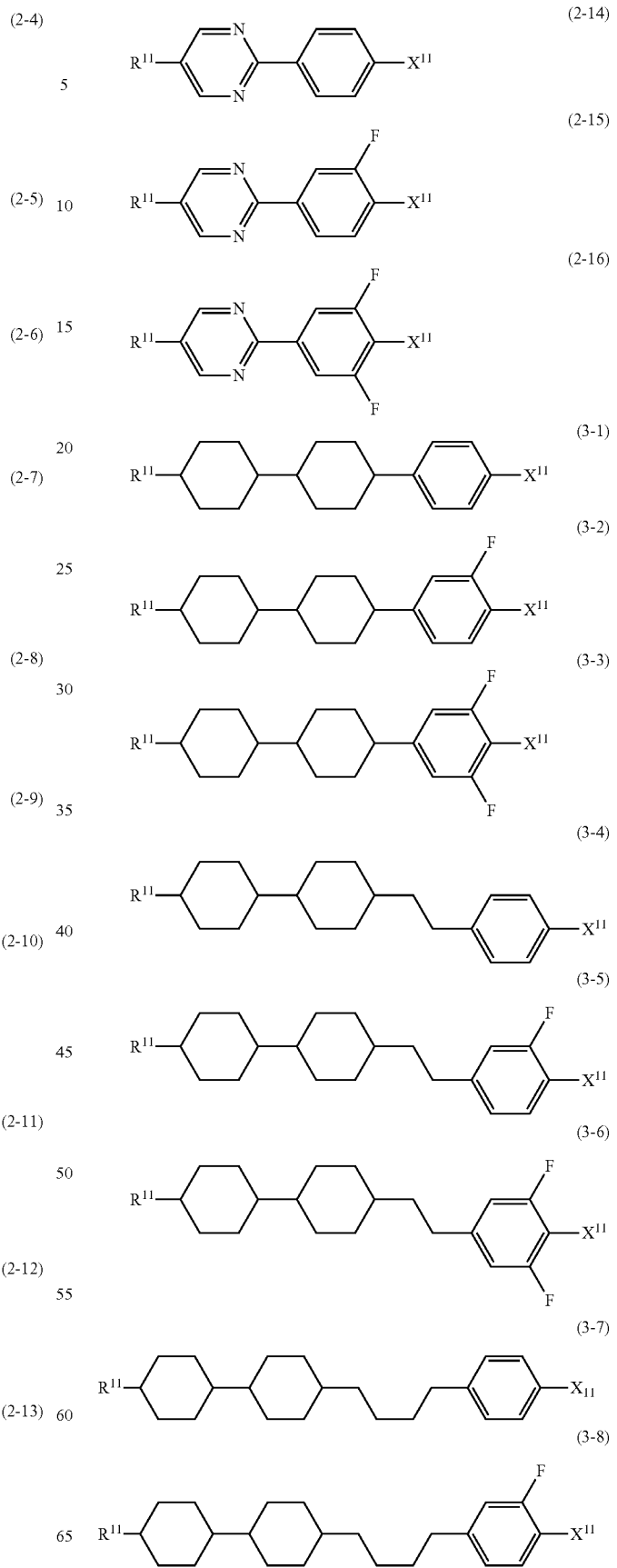

(3-9) 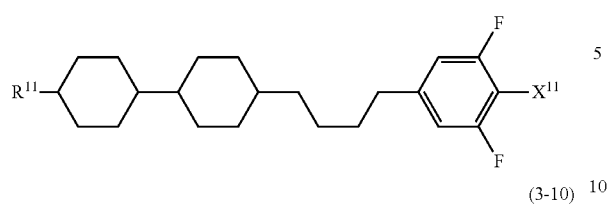
(3-10) 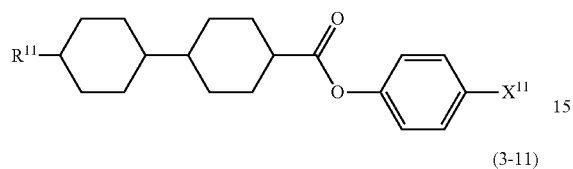
(3-11) 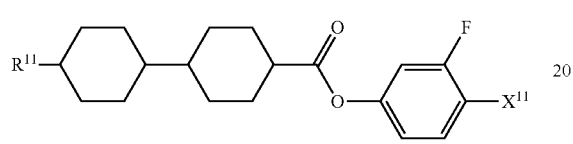
(3-12) 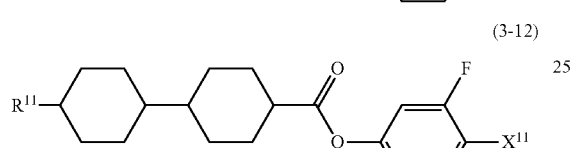
(3-13) 
(3-14) 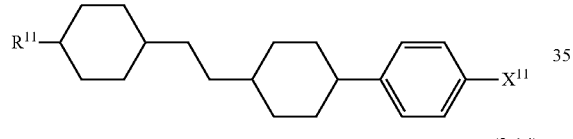
(3-15) 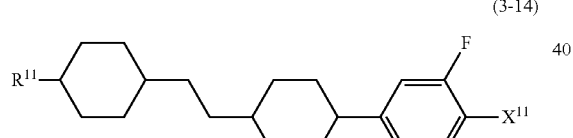
(3-16) 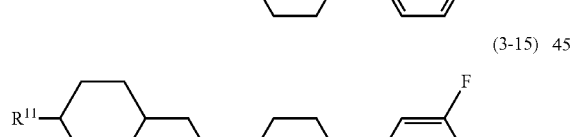
(3-17) 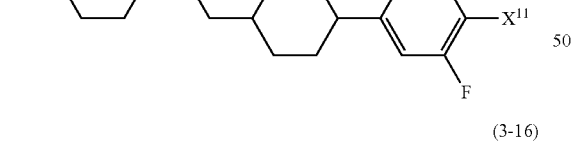
(3-18) 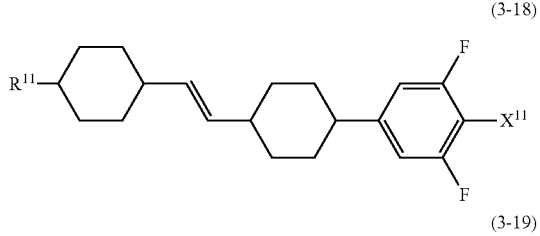
(3-19) 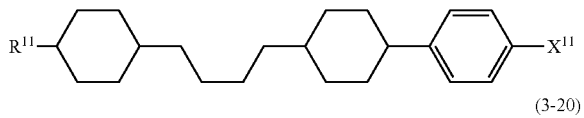
(3-20) 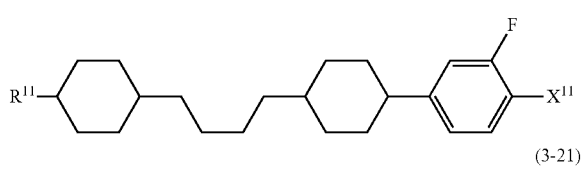
(3-21) 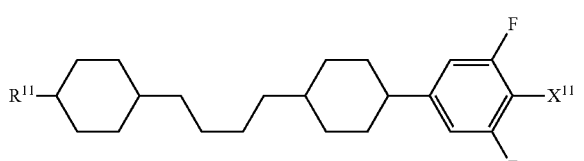
(3-22) 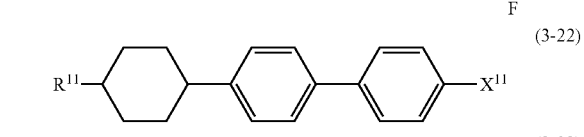
(3-23) 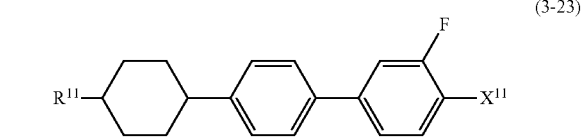
(3-24) 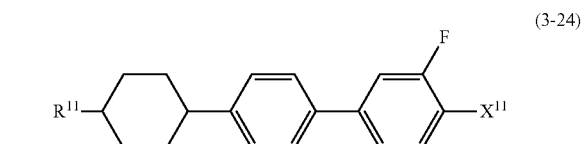
(3-25) 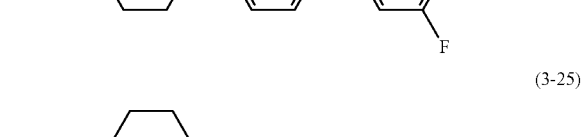
(3-26) 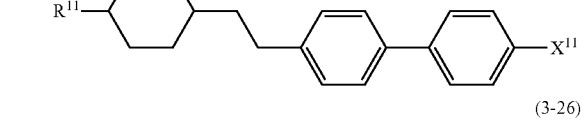
(3-27) 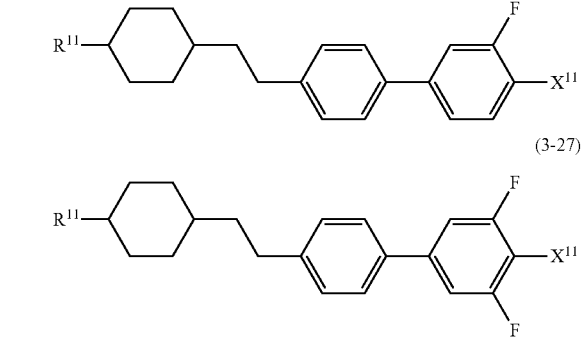

(3-28) 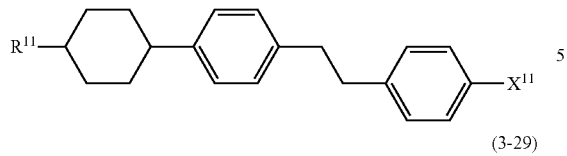
(3-29) 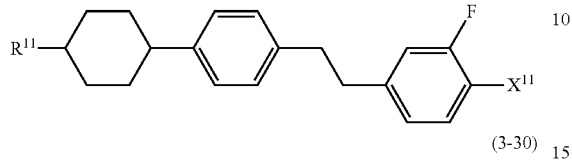
(3-30) 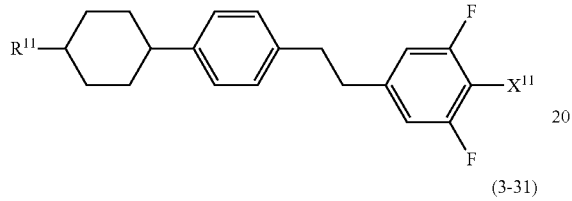
(3-31) 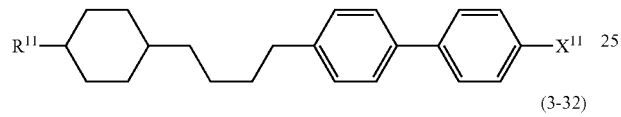
(3-32) 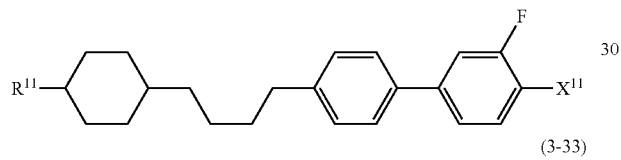
(3-33) 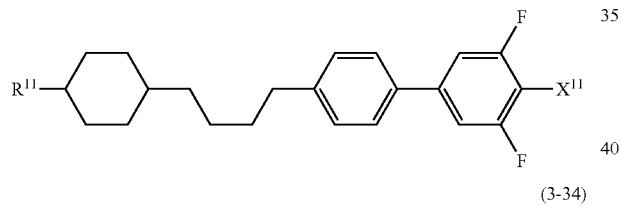
(3-34) 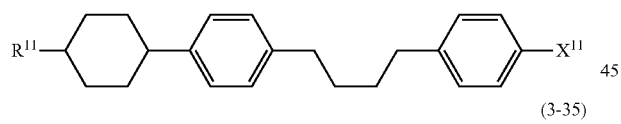
(3-35) 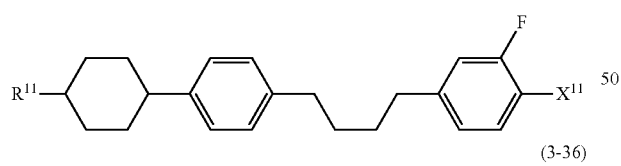
(3-36) 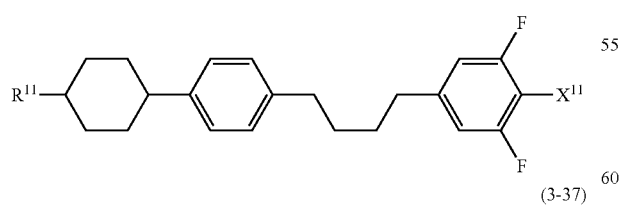
(3-37) 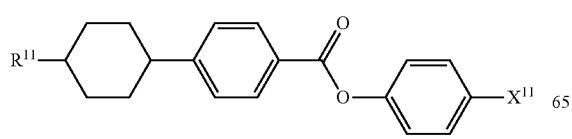
(3-38) 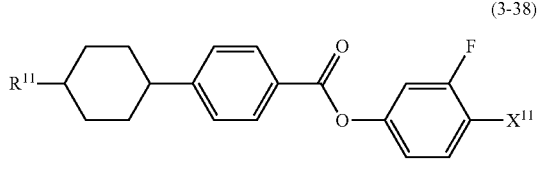
(3-39) 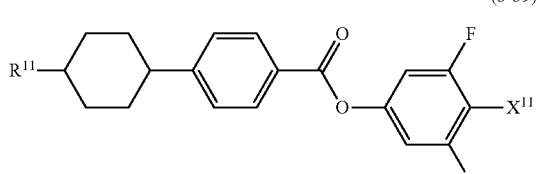
(3-40) 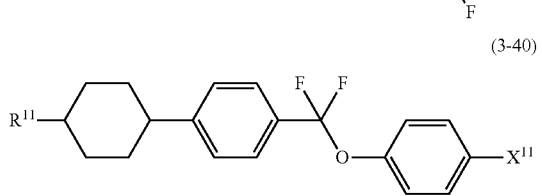
(3-41) 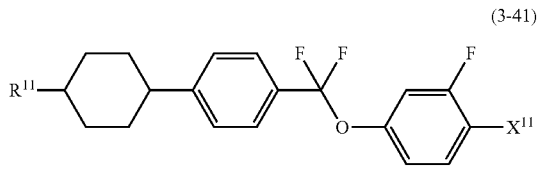
(3-42) 
(3-43) 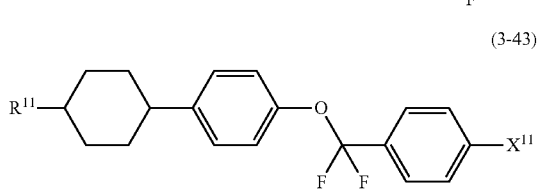
(3-44) 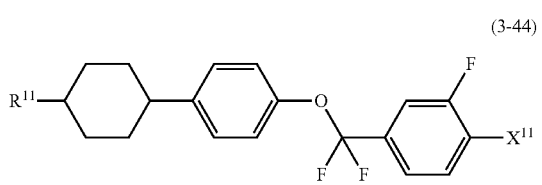
(3-45) 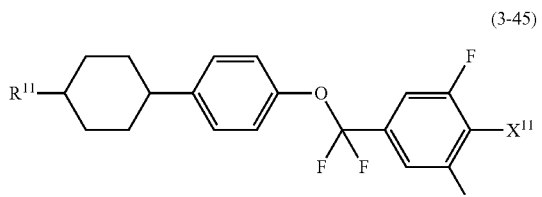
(3-46) 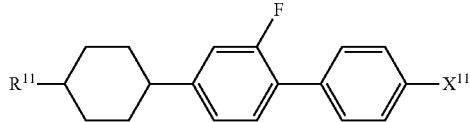

(3-47) 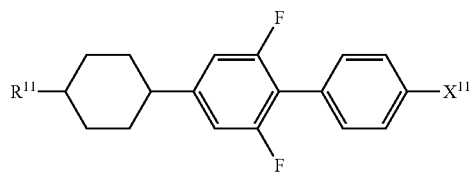
(3-48) 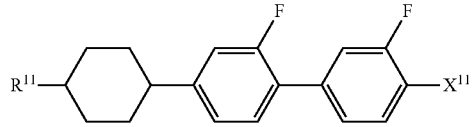
(3-49) 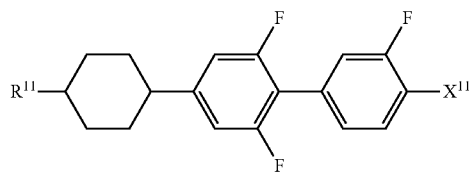
(3-50) 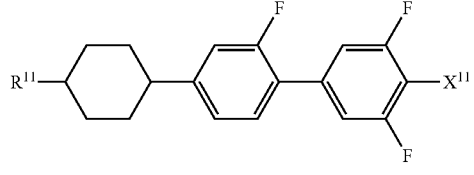
(3-51) 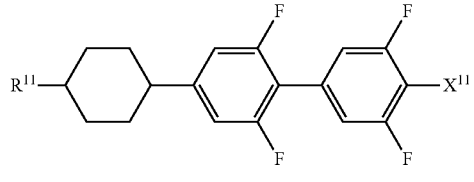
(3-52) 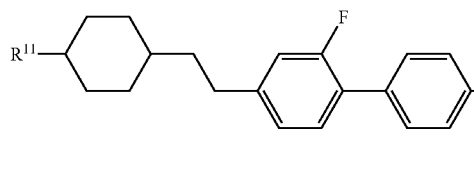
(3-53) 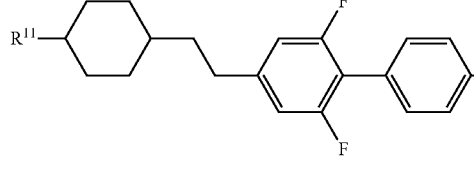
(3-54) 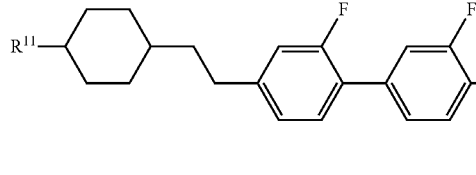
(3-55) 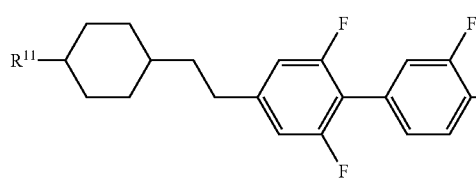
(3-56) 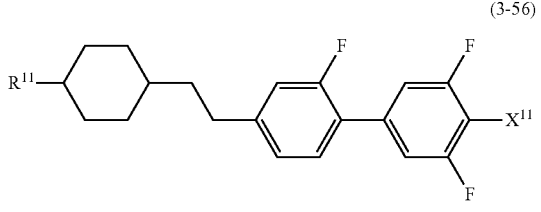
(3-57) 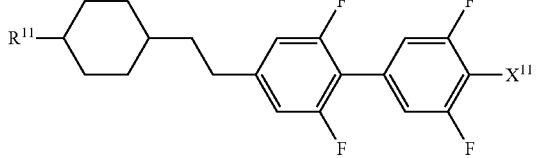
(3-58) 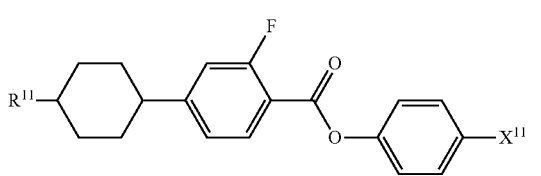
(3-59) 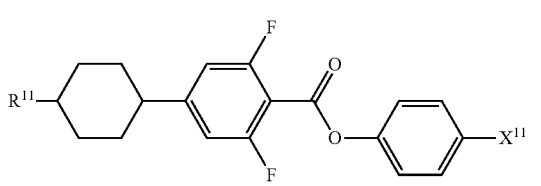
(3-60) 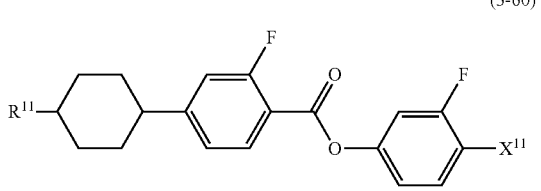
(3-61) 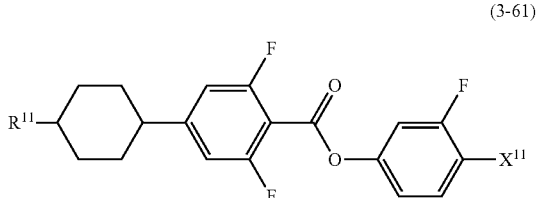
(3-62) 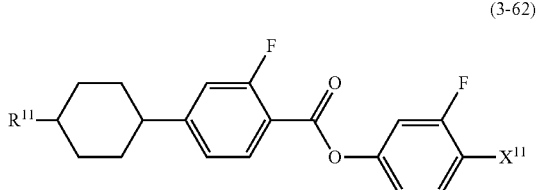

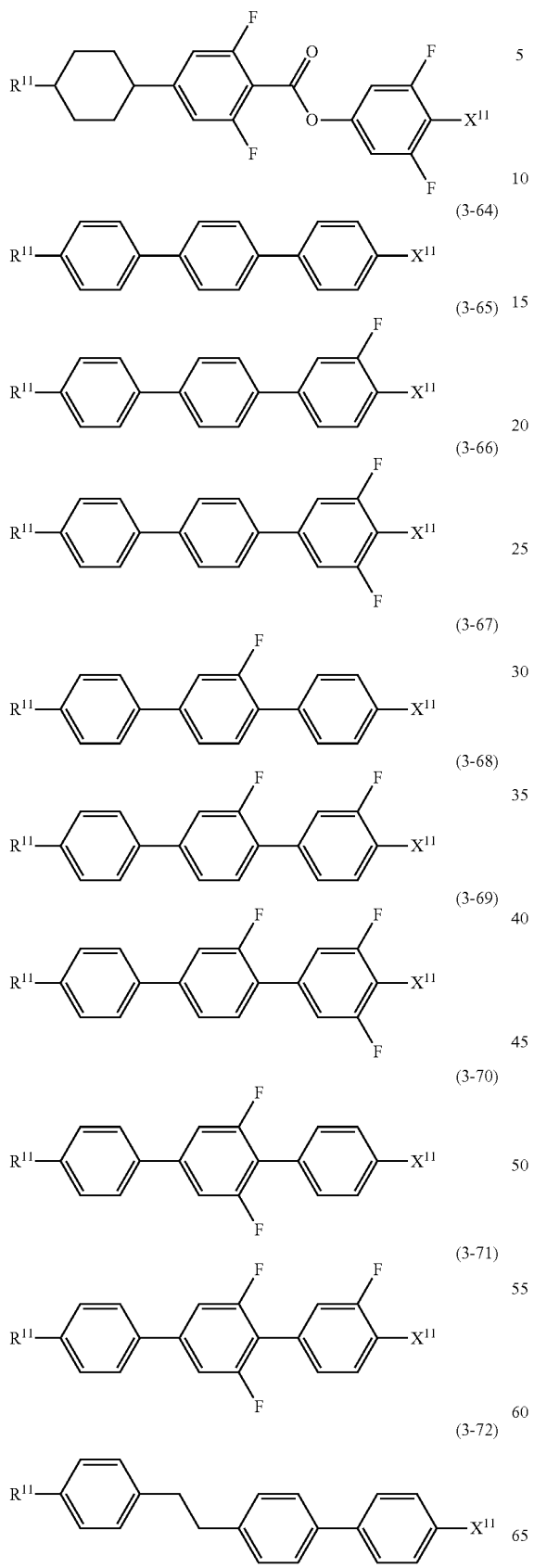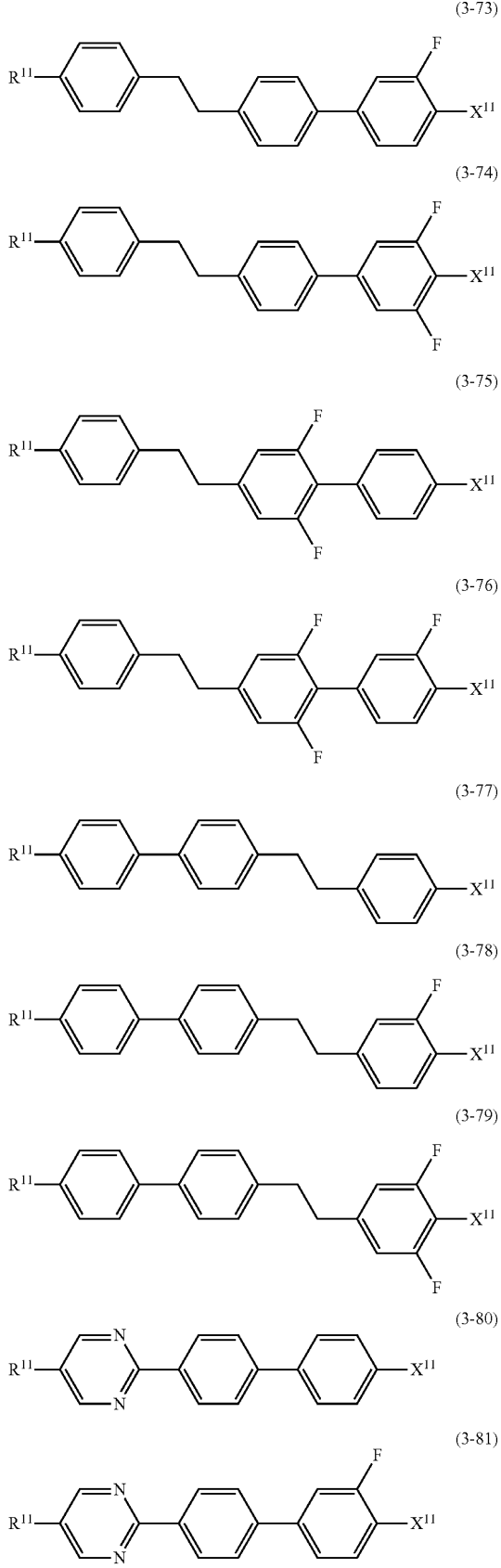

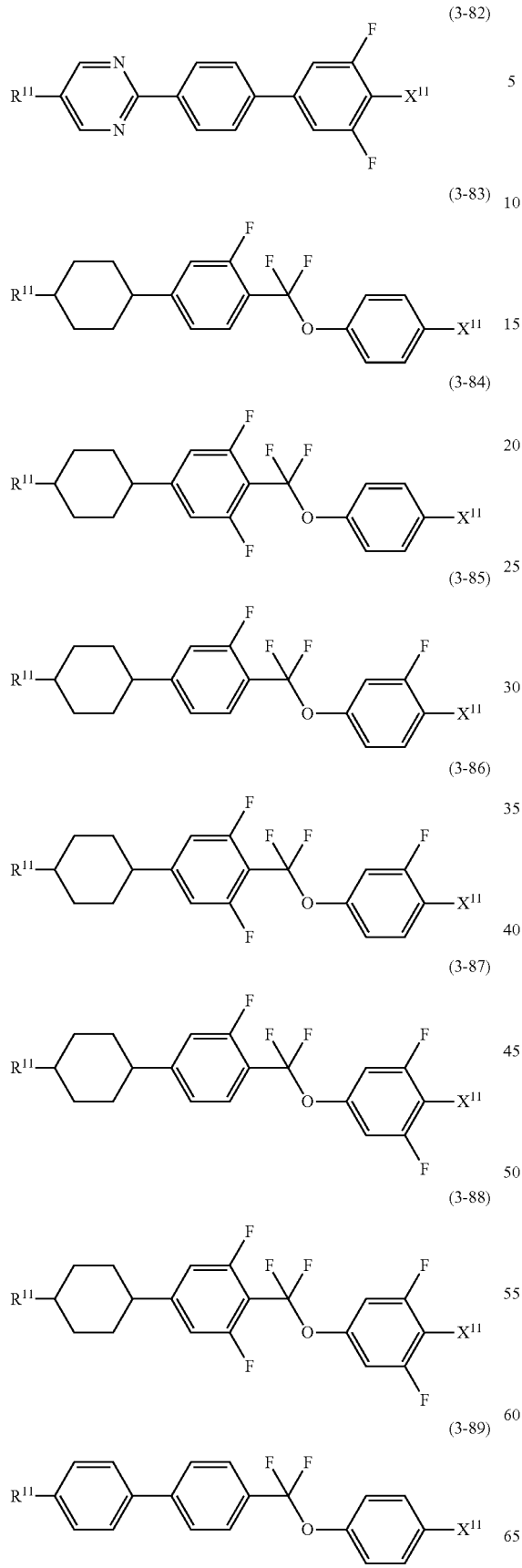
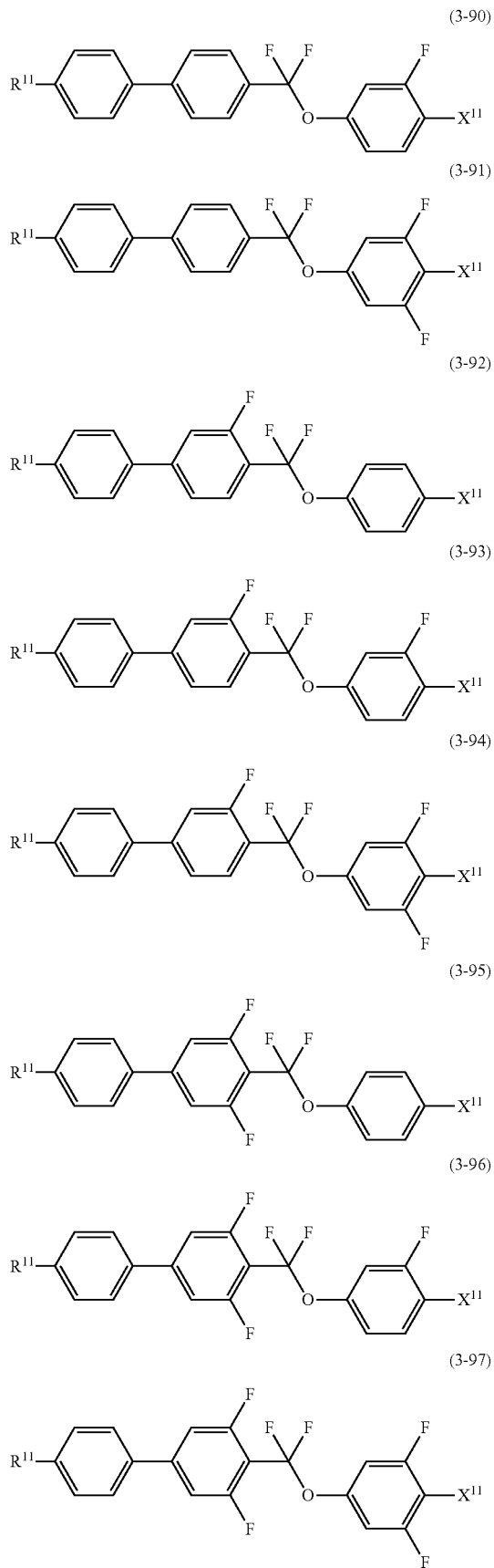

(3-98)
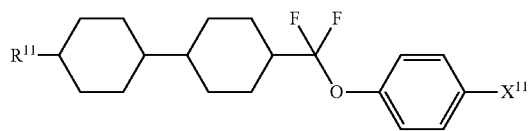
(3-99)
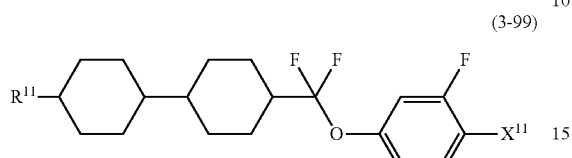
(3-100)
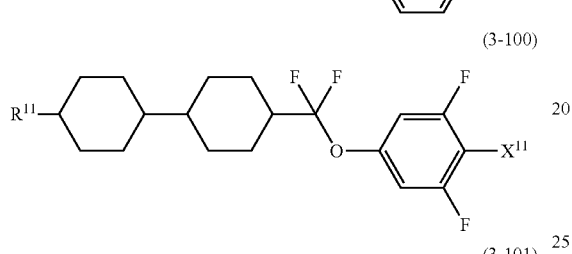
(3-101)
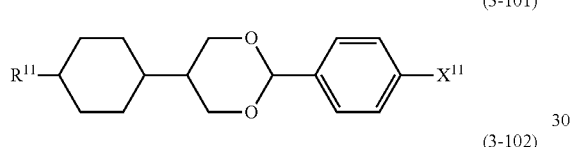
(3-102)
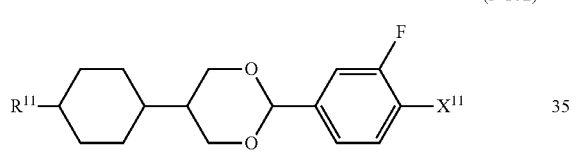
(3-103)
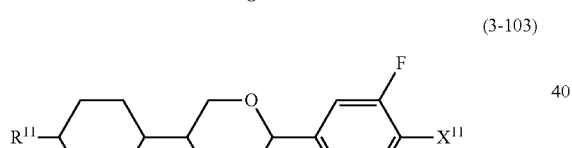
(3-104)
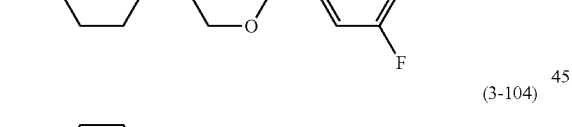
(3-105)
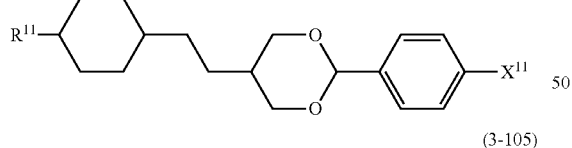
(3-106)
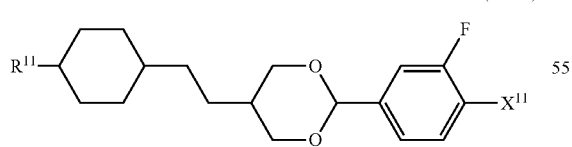
(3-107)
(3-108)
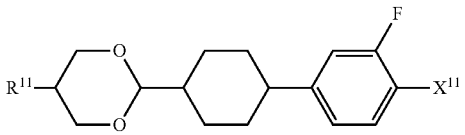
(3-109)
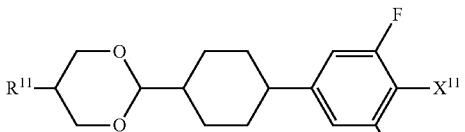
(3-110)
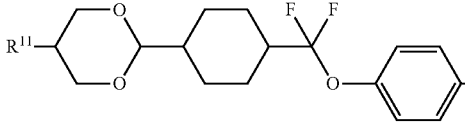
(3-111)
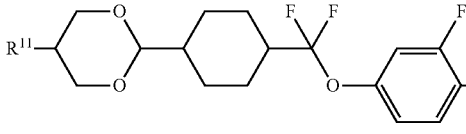
(3-112)
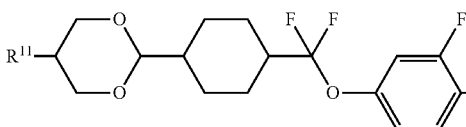
(3-113)
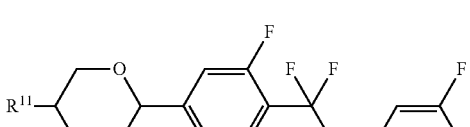
(4-1)
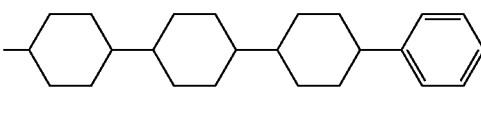
(4-2)
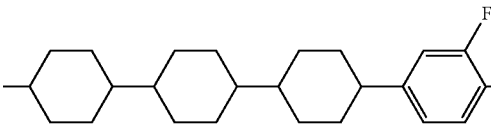

(4-3) 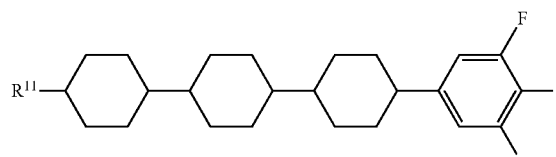
(4-4) 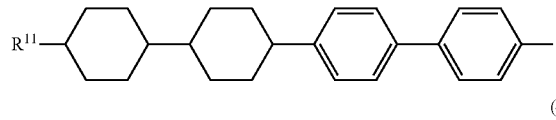
(4-5) 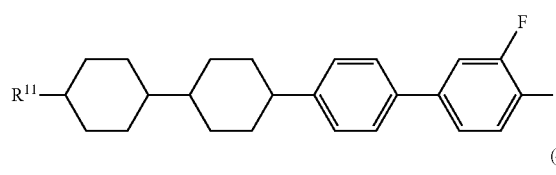
(4-6) 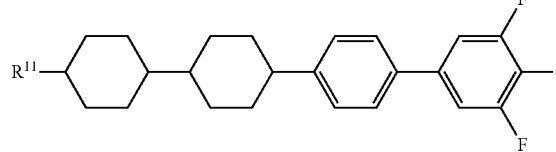
(4-7) 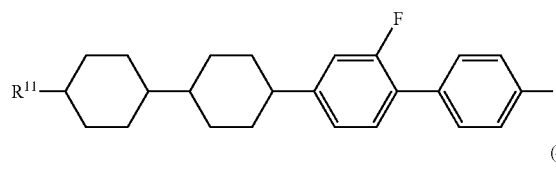
(4-8) 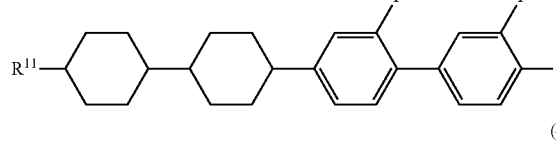
(4-9) 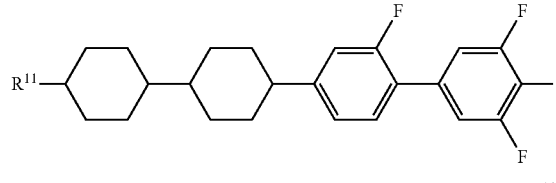
(4-10) 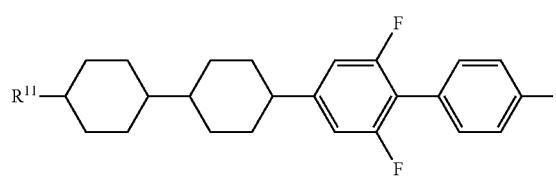
(4-11) 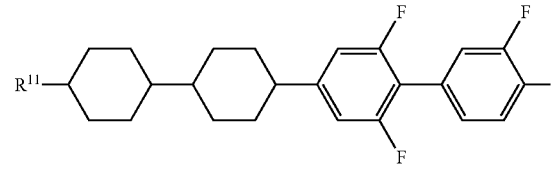
(4-12) 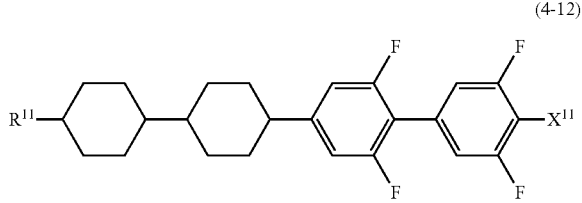
(4-13) 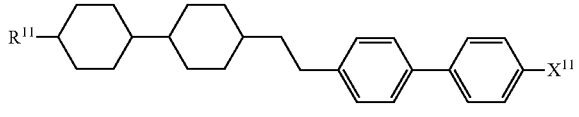
(4-14) 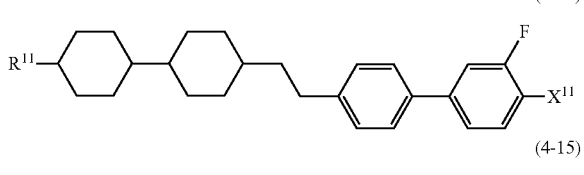
(4-15) 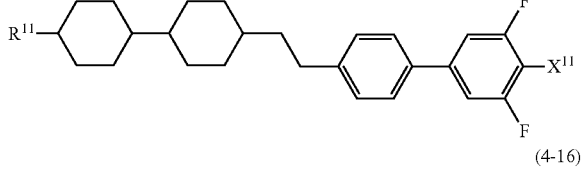
(4-16) 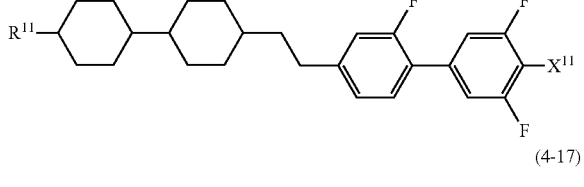
(4-17) 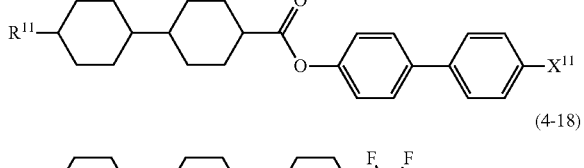
(4-18) 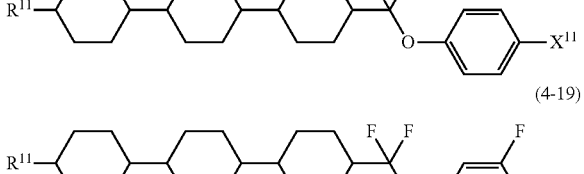
(4-19) 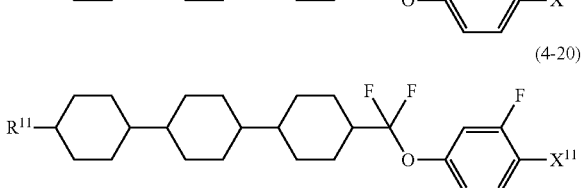
(4-20) 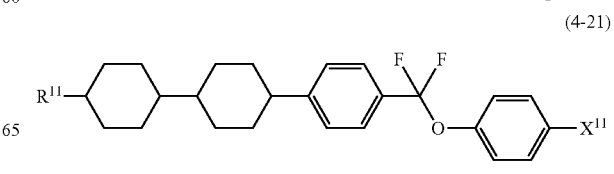
(4-21) 

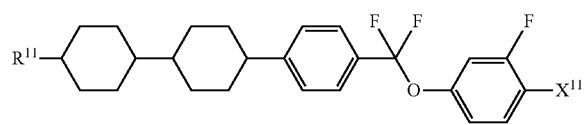
(4-22)
(4-30)
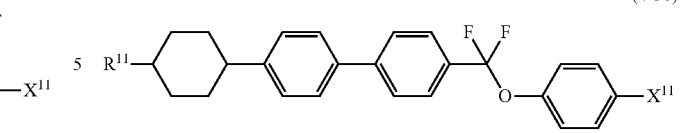
(4-23) (4-31)
(4-24) (4-32)
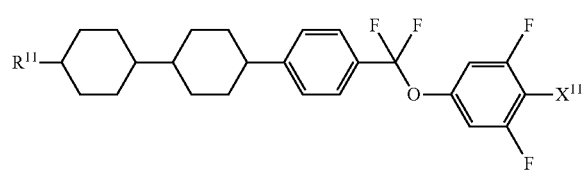
(4-25) (4-33)
(4-26) (4-34)
(4-27) (4-35)
(4-28) (4-36)
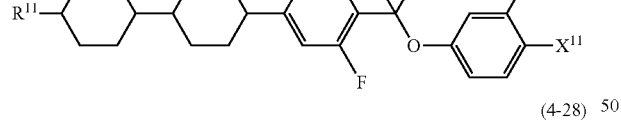
(4-29) (4-37)

(4-38) 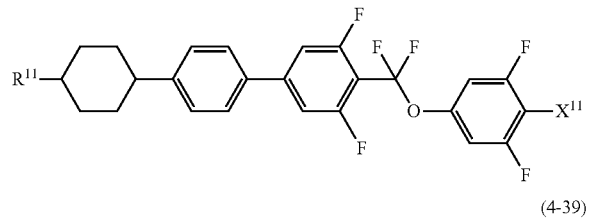
(4-39) 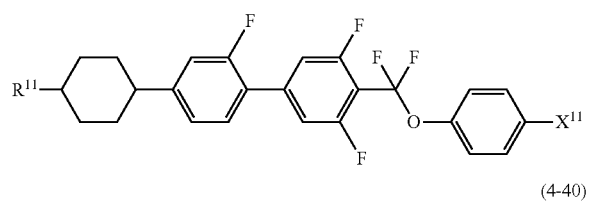
(4-40) 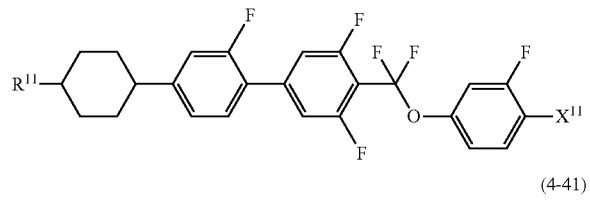
(4-41) 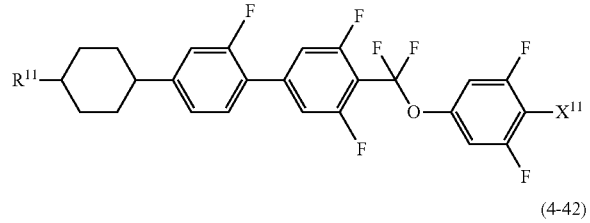
(4-42) 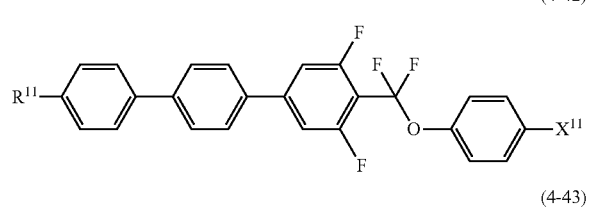
(4-43) 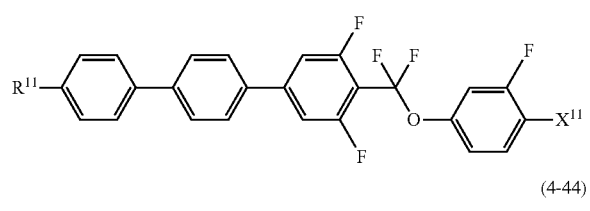
(4-44) 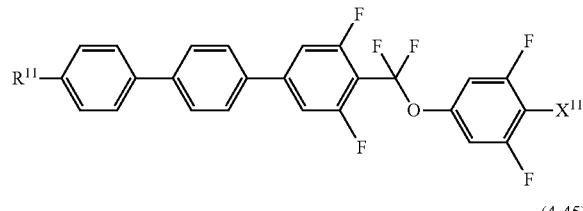
(4-45) 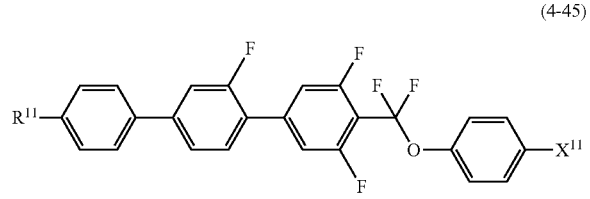
(4-46) 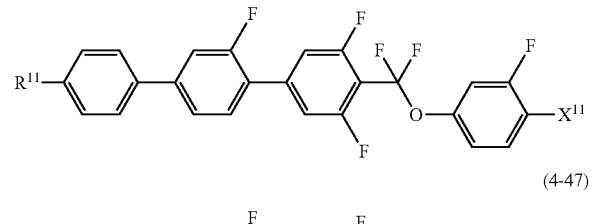
(4-47) 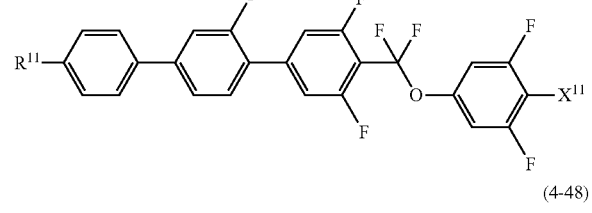
(4-48) 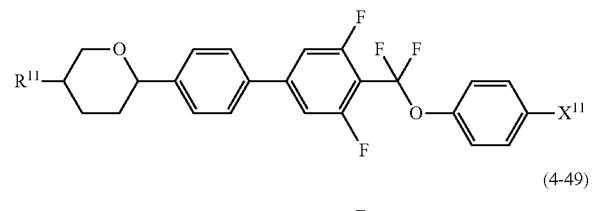
(4-49) 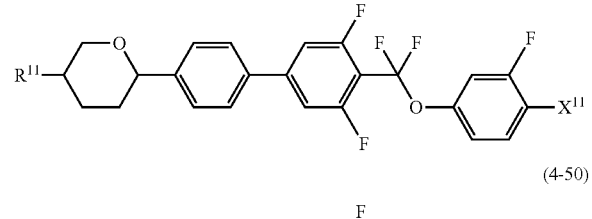
(4-50) 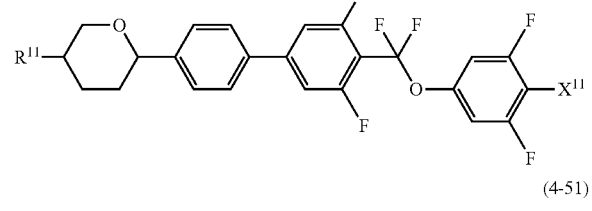
(4-51) 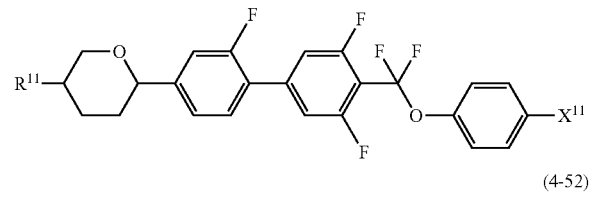
(4-52) 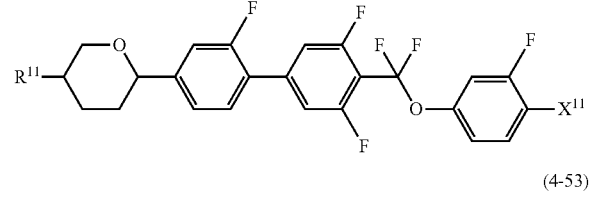
(4-53) 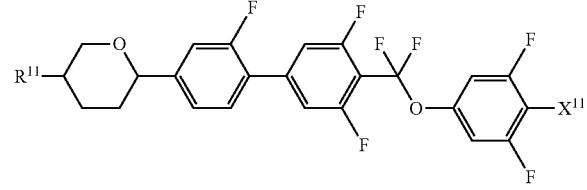

-continued (4-54)
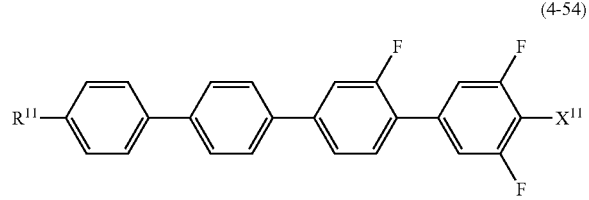

(4-55)
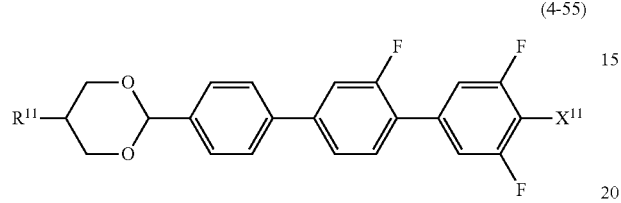

(4-56)
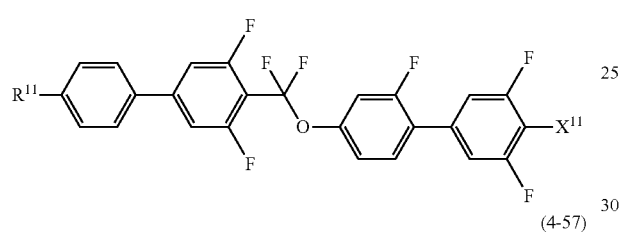

(4-57)
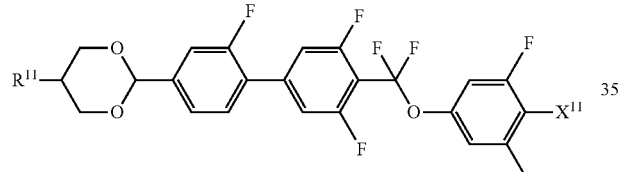

In the compounds (component B), $R^{11}$ and $X^{11}$ are defined in a manner identical with the definitions in item 10 described above.

Component B has positive dielectric anisotropy and superb stability to heat, light or the like, and therefore is used when preparing a composition for a mode such as PS-IPS, PS-FFS and PSA-OCB. A content of component B is suitably, based on the liquid crystal composition, in the range from approximately 1% by weight to approximately 99% by weight, preferably, in the range from approximately 10% by weight to approximately 97% by weight, and further preferably, in the range from approximately 40% by weight to approximately 95% by weight. Further addition of compounds (13) to (15) (component E) allows adjustment of viscosity of the composition. When component B is added to a composition having negative dielectric anisotropy, a content of component B is preferably in the range of approximately 30% by weight or less based on the liquid crystal composition. Addition of component B allows adjustment of an elastic constant of the composition and adjustment of a voltage-transmittance curve of a device.

Component C includes compound (5) in which a right-terminal group is —C≡N or —C≡C—C≡N. Specific preferred examples of component C include compounds (5-1) to (5-64).

(5-1)
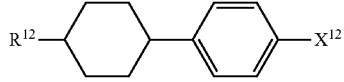

(5-2)
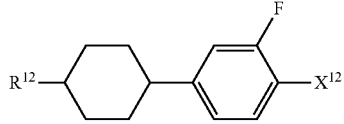

(5-3)
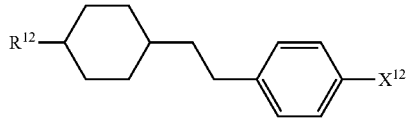

(5-4)
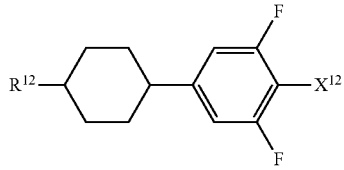

(5-5)
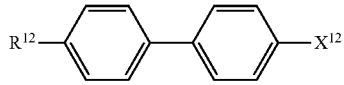

(5-6)
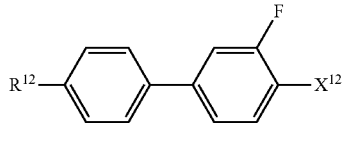

(5-7)
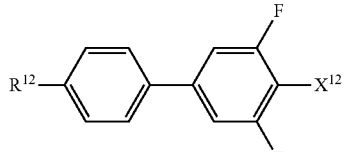

(5-8)
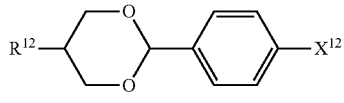

(5-9)
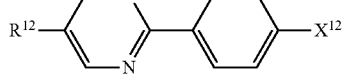

(5-10)
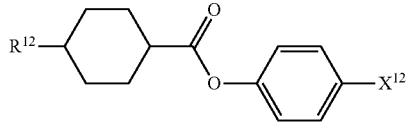

(5-11)
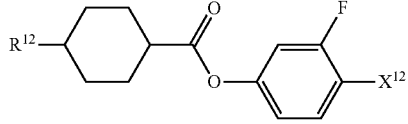

-continued
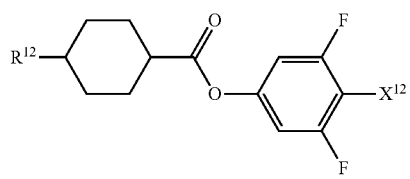  (5-12)
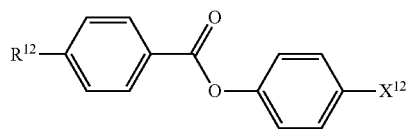  (5-13)
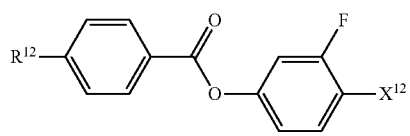  (5-14)
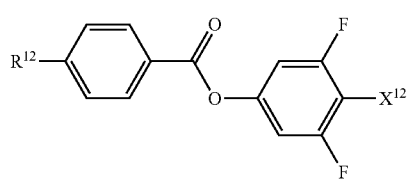  (5-15)
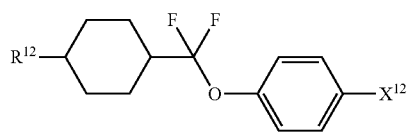  (5-16)
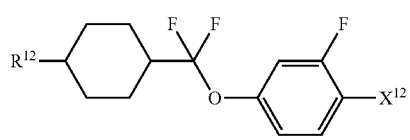  (5-17)
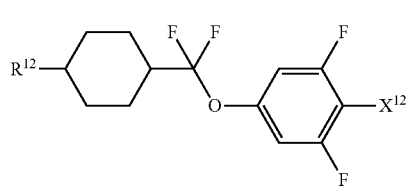  (5-18)
  (5-19)
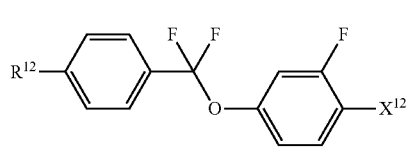  (5-20)
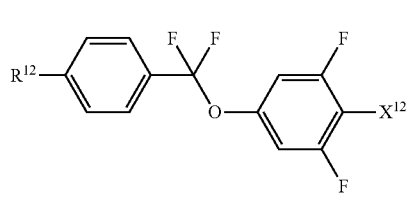  (5-21)
-continued
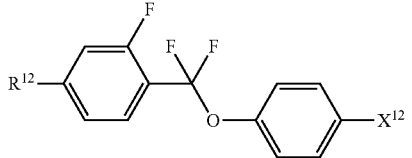  (5-22)
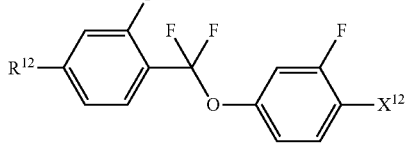  (5-23)
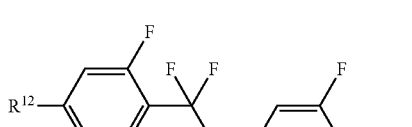  (5-24)
  (5-25)
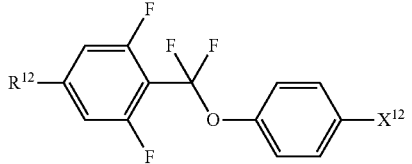  (5-26)
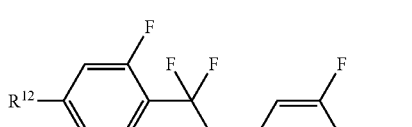  (5-27)
  (5-28)
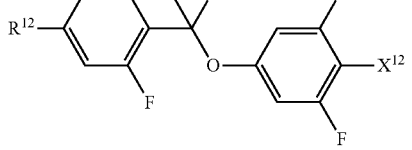  (5-29)
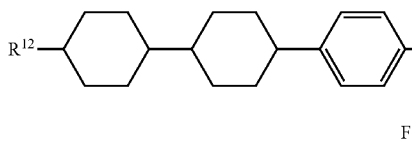  (5-30)

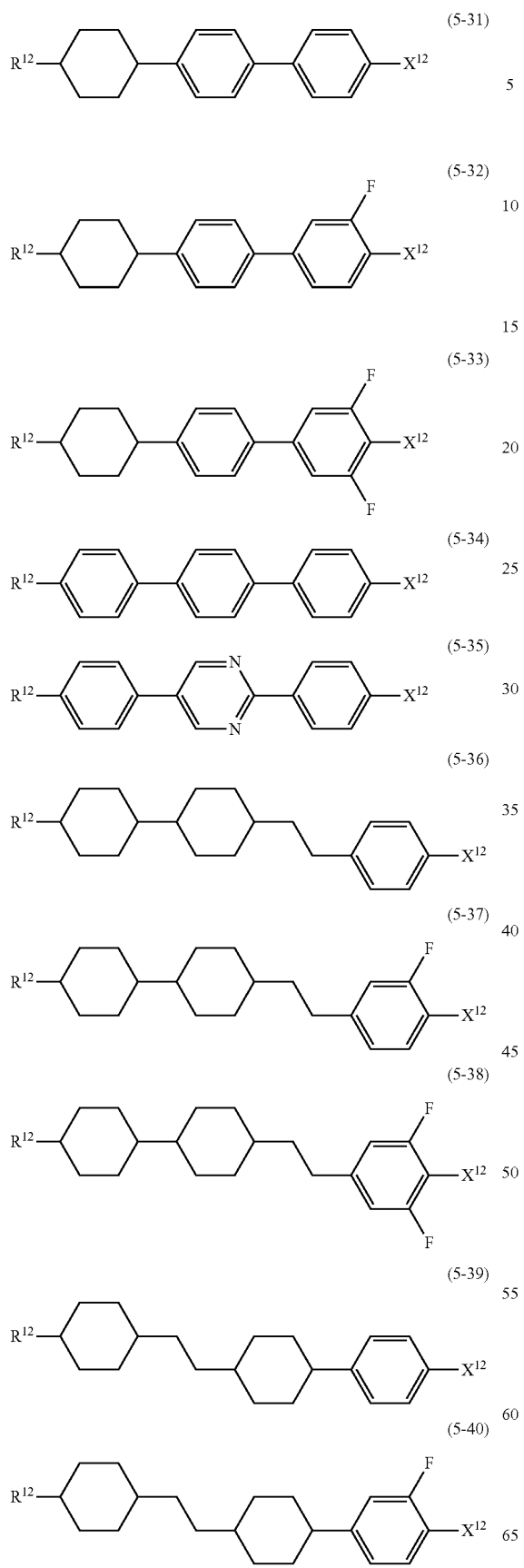
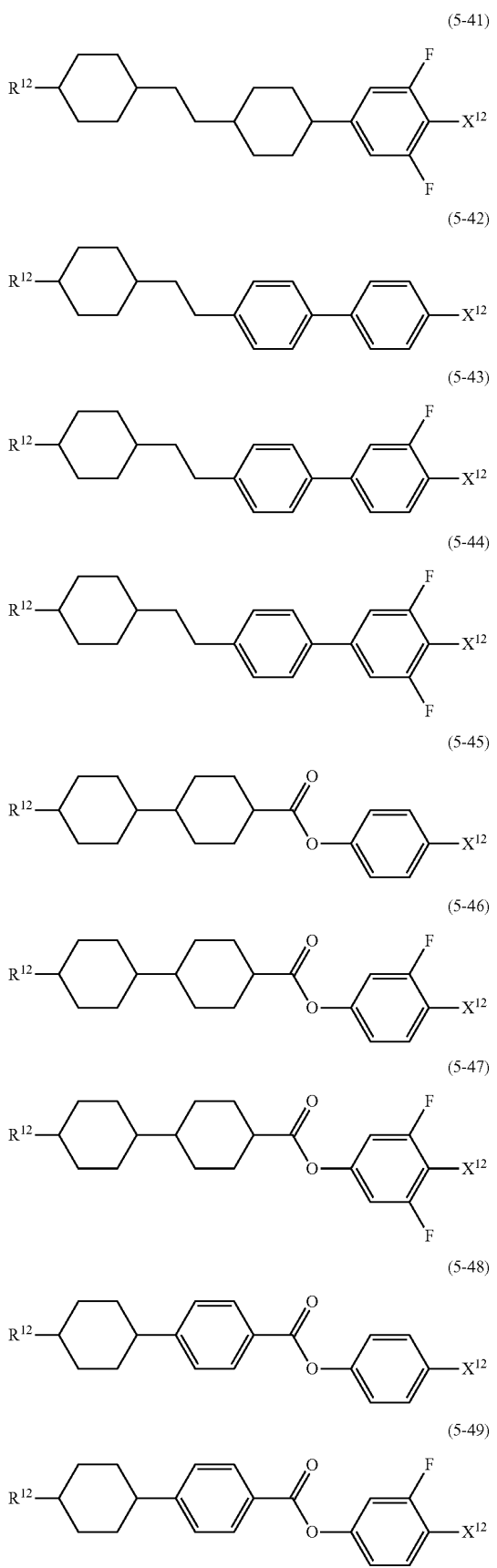

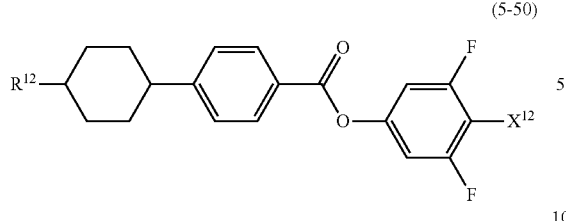
(5-50)

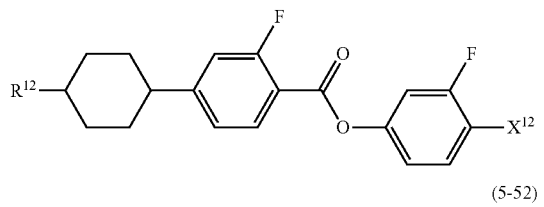
(5-51)

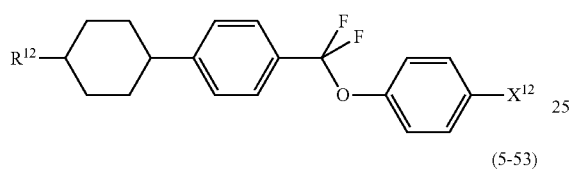
(5-52)

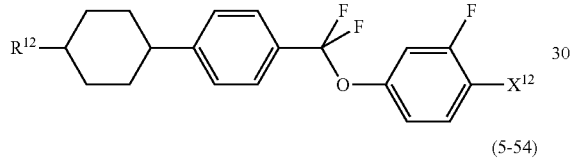
(5-53)

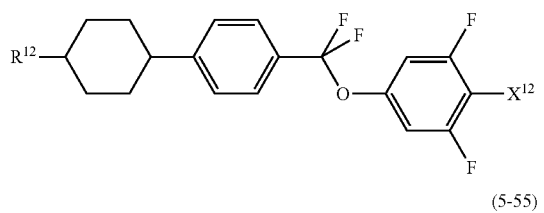
(5-54)

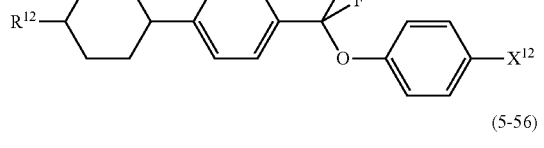
(5-55)

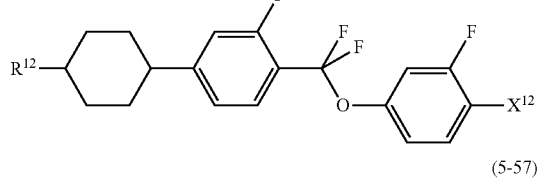
(5-56)

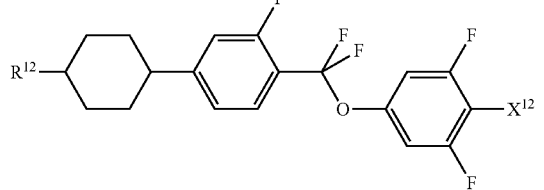
(5-57)

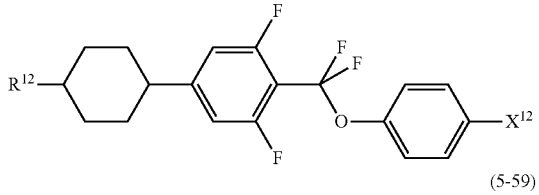
(5-58)

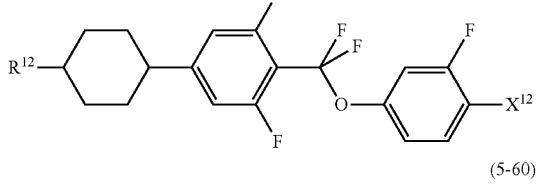
(5-59)

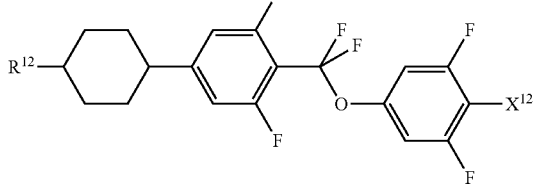
(5-60)

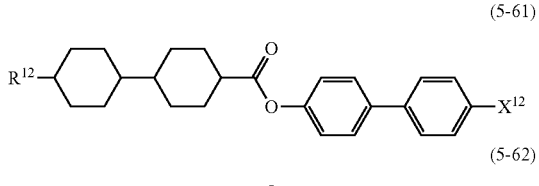
(5-61)

(5-62)

(5-63)

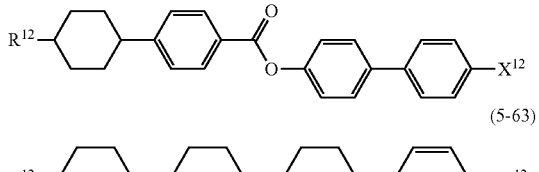

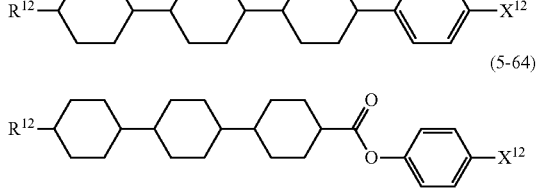
(5-64)

In the compounds (component C), $R^{12}$ and $X^{12}$ are defined in a manner identical with the definitions in item 11 described above.

Component C has a large value of positive dielectric anisotropy, and therefore is mainly used when preparing a composition for a mode such as PS-TN. Dielectric anisotropy of the composition can be increased by adding component C. Component C is effective in extending a temperature range of the liquid crystal phase, adjusting viscosity or adjusting optical anisotropy. Component C is also useful to adjustment of the voltage-transmittance curve of the device.

When preparing the composition for the mode such as PS-TN, a content of component C is suitably, based on the liquid crystal composition, in the range from approximately 1% by weight to approximately 99% by weight, preferably, in the range from approximately 10% by weight to approximately 97% by weight, and further preferably, in the range from approximately 40% by weight to approximately 95% by weight. Further addition of component E allows adjustment of the temperature range of the liquid crystal phase, the viscosity, the optical anisotropy, the dielectric anisotropy or the like. When component C is added to a composition having negative dielectric anisotropy, a content of component C is preferably in the range of approximately 30% by weight or less based on the liquid crystal composition. Addition of component C allows adjustment of the elastic constant of the composition and adjustment of the voltage-transmittance curve of the device.

Component D includes compounds (6) to (12). The compounds have a benzene ring lateral positions of which are replaced by two of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-11) to (10-11), compounds (11-1) to (11-3) and compounds (12-1) to (12-3).

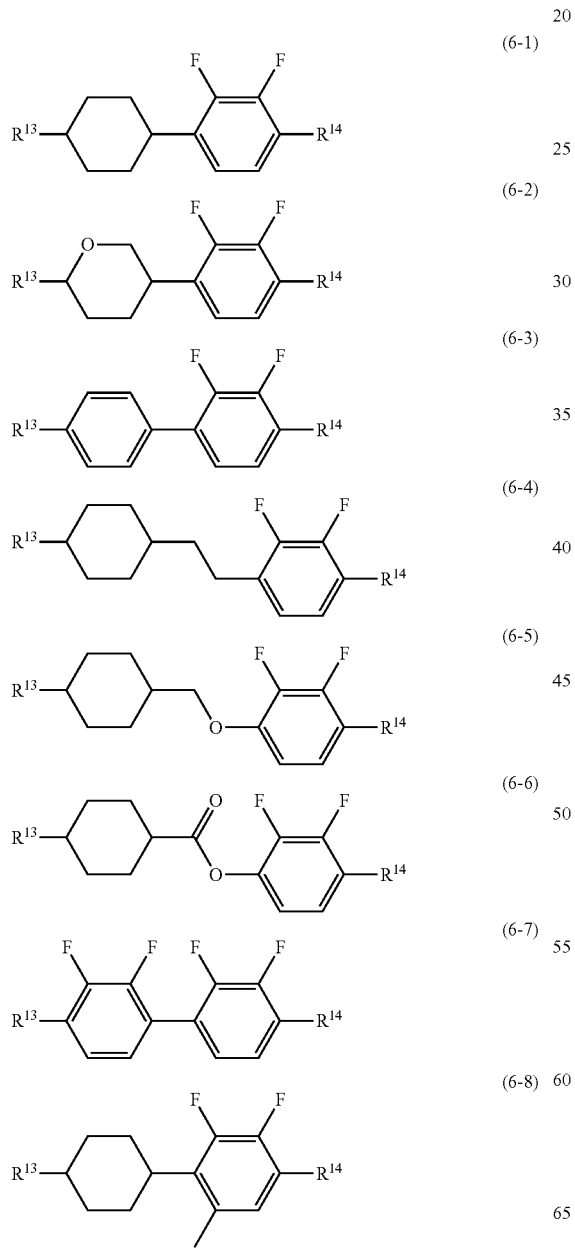

-continued

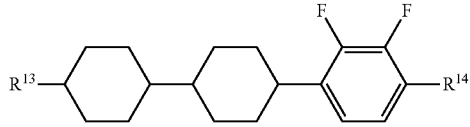
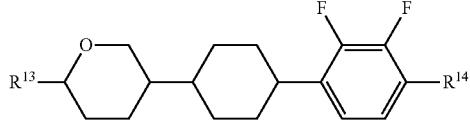
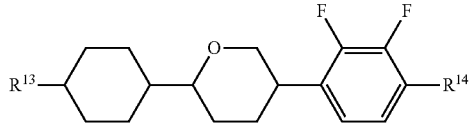
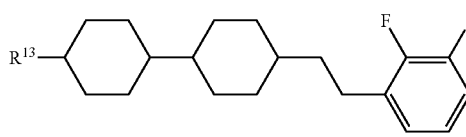
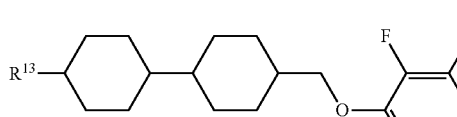
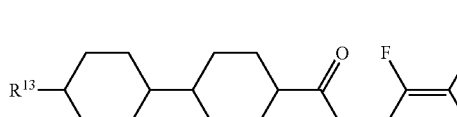
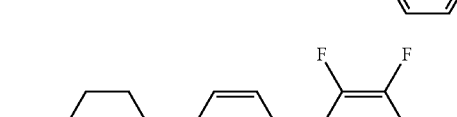
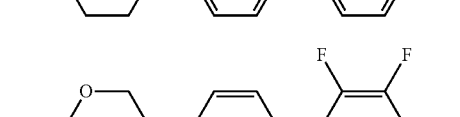
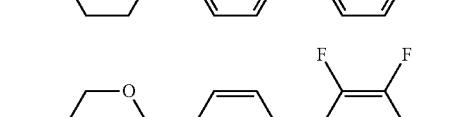
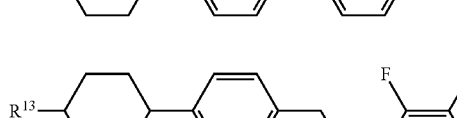

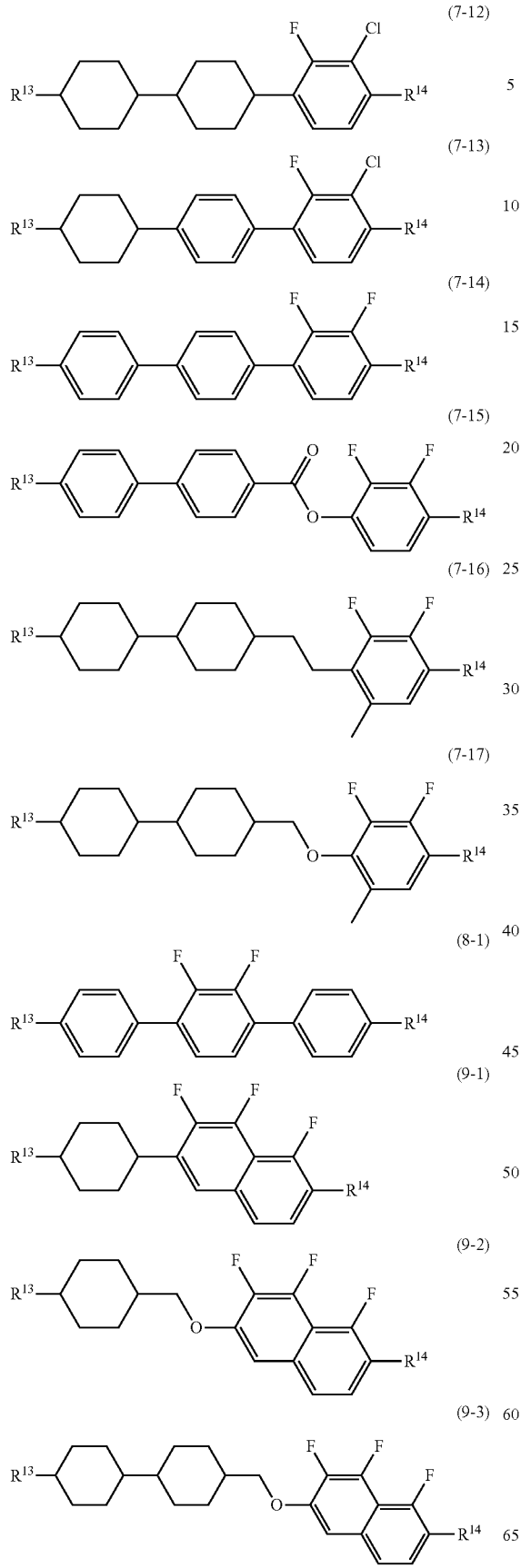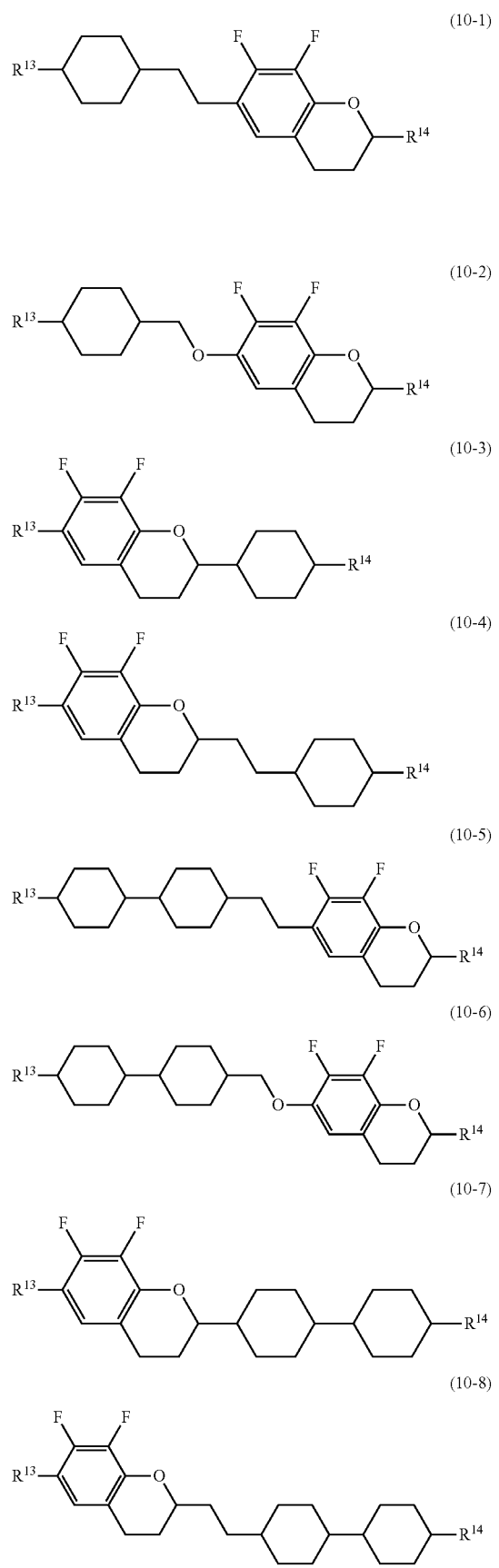

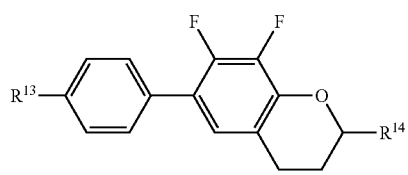
(10-9)

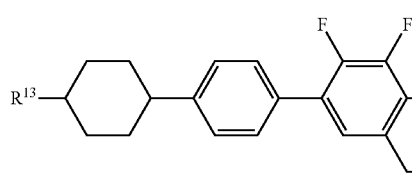
(10-10)

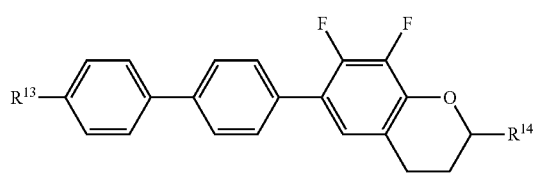
(10-11)

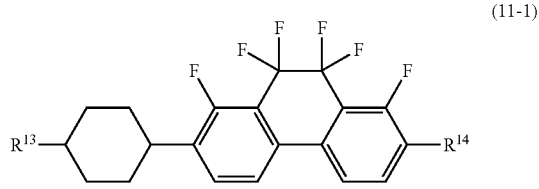
(11-1)

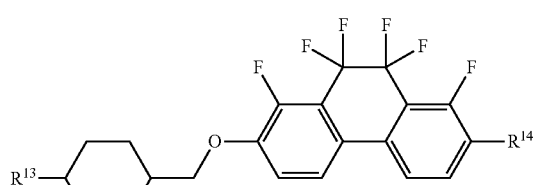
(11-2)

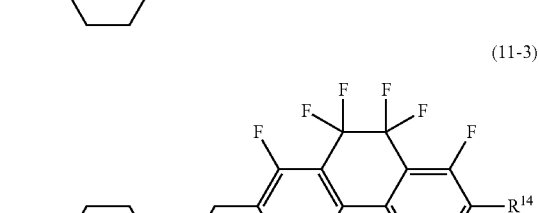
(11-3)

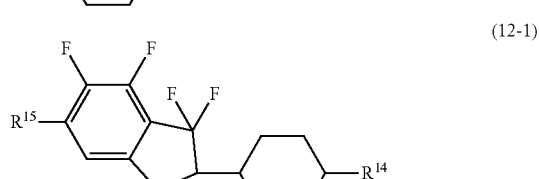
(12-1)

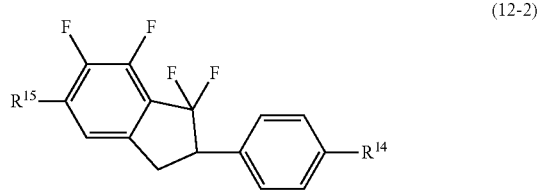
(12-2)

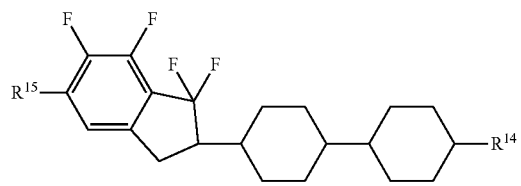
(12-3)

In the compounds (component D), $R^{13}$, $R^{14}$ and $R^{15}$ are defined in a manner identical with the definitions in item 12 described above.

Component D includes a compound having negative dielectric anisotropy. Component D is used when preparing a composition for a mode such as PS-IPS, PS-FFS and PSA-VA. If a content of component D is increased, dielectric anisotropy of the composition is negatively increased, but viscosity increases. Thus, the content is preferably decreased, as long as a required value of threshold voltage of a device is satisfied. Accordingly, in consideration of approximately 5 of an absolute value of dielectric anisotropy, the content is preferably in the range of approximately 40% by weight or more in order to allow sufficient voltage driving.

Among types of compound D, compound (6) is a bicyclic compound, and therefore effective mainly in adjusting the viscosity, the optical anisotropy or the dielectric anisotropy. Compound (7) and compound (8) each are a tricyclic compound, and therefore effective in increasing the maximum temperature, the optical anisotropy or the dielectric anisotropy. Compounds (9) to (12) each are effective in increasing the dielectric anisotropy.

When preparing a composition for a mode such as PS-IPS, PS-FFS and PSA-VA, a content of component D is preferably, based on the liquid crystal composition, in the range from approximately 40% by weight or more, and further preferably, in the range from approximately 40% by weight to approximately 95% by weight. Addition of component D allows adjustment of the elastic constant of the composition and adjustment of the voltage-transmittance curve of the device. When component D is added to a composition having positive dielectric anisotropy, a content of component D is preferably in the range of approximately 30% by weight or less based on the liquid crystal composition. Addition of component D allows adjustment of the elastic constant of the composition and adjustment of the voltage-transmittance curve of the device.

Component E includes a compound in which two terminal groups are alkyl or the like. Specific preferred examples of component E include compounds (13-1) to (13-11), compounds (14-1) to (14-19) and compounds (15-1) to (15-7).

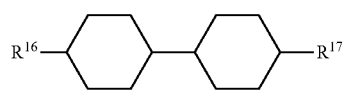
(13-1)

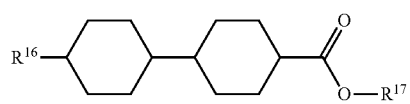
(13-2)

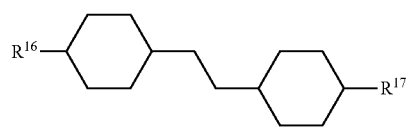
(13-3)
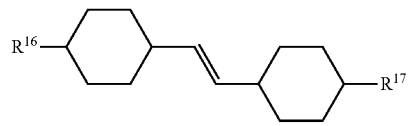
(13-4)
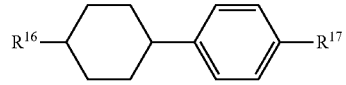
(13-5)
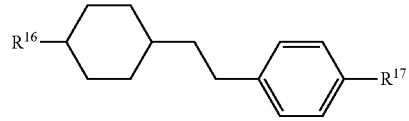
(13-6)
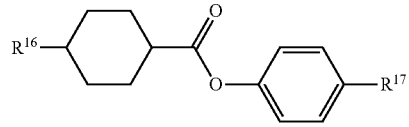
(13-7)
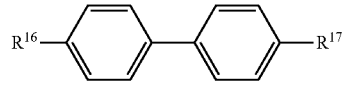
(13-8)
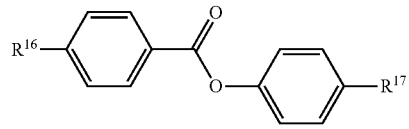
(13-9)
(13-10)
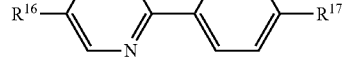
(13-11)
(14-1)
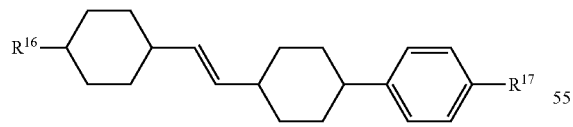
(14-2)
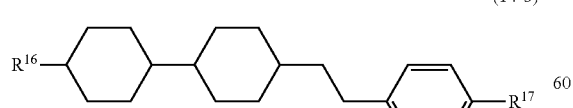
(14-3)
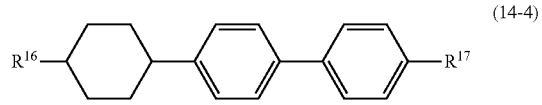
(14-4)
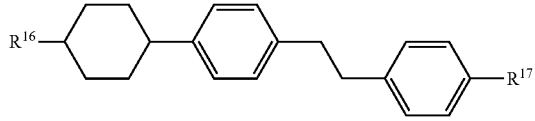
(14-5)
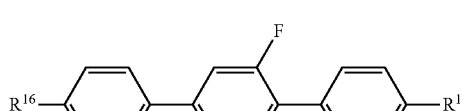
(14-6)
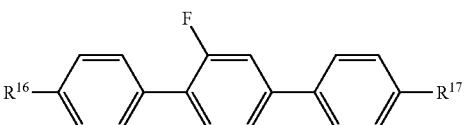
(14-7)
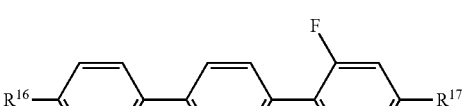
(14-8)
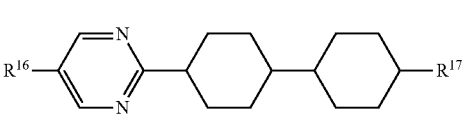
(14-9)
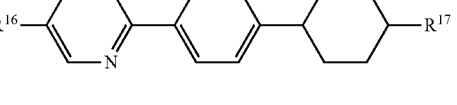
(14-10)
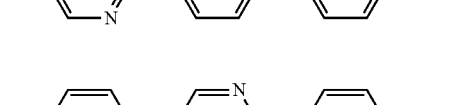
(14-11)
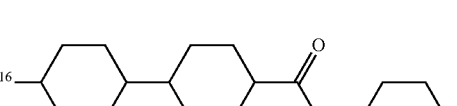
(14-12)
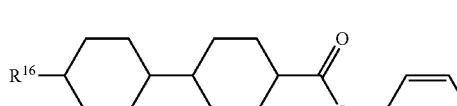
(14-13)
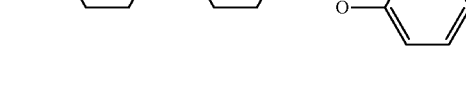
(14-14)

(14-15) 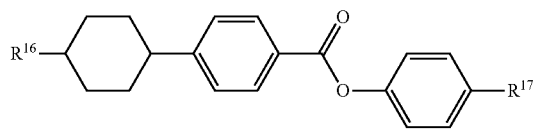

(14-16) 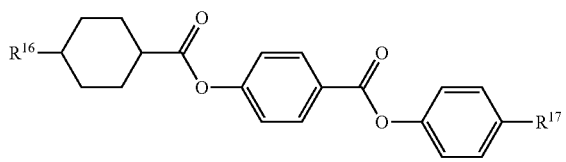

(14-17) 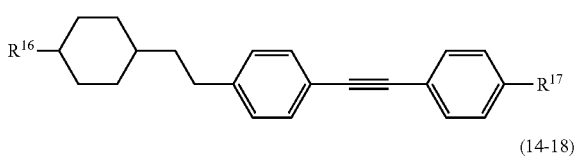

(14-18) 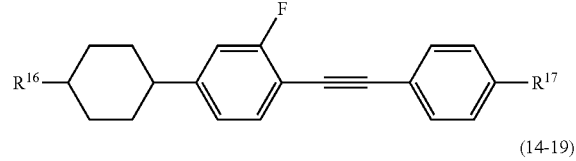

(14-19) 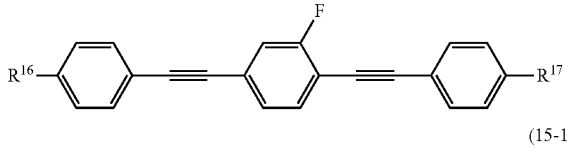

(15-1) 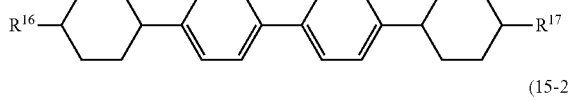

(15-2) 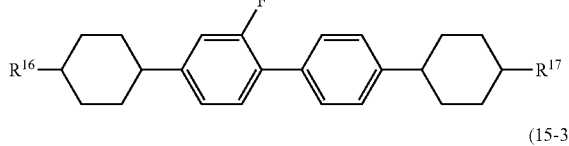

(15-3) 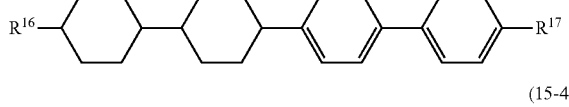

(15-4) 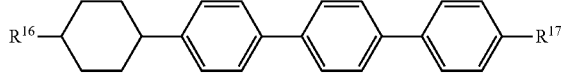

(15-5) 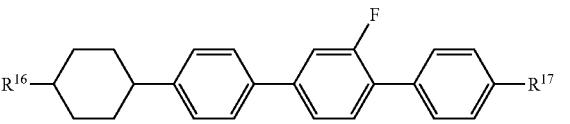

(15-6) 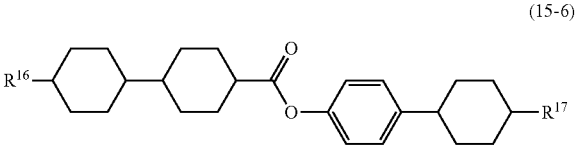

(15-7) 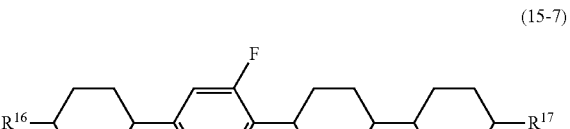

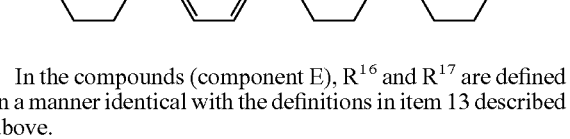

In the compounds (component E), $R^{16}$ and $R^{17}$ are defined in a manner identical with the definitions in item 13 described above.

Component E has a small absolute value of dielectric anisotropy, and therefore is close to neutrality. Compound (13) is effective mainly in adjusting the viscosity or the optical anisotropy. Compound (14) and compound (15) are effective in extending the temperature range of the nematic phase by increasing the maximum temperature, or effective in adjusting the optical anisotropy.

If the content of component E is increased, the viscosity of the composition decreases, but the dielectric anisotropy decreases. Thus, the content is preferably increased, as long as a required value of threshold voltage of the device is satisfied. Accordingly, when preparing a composition for a mode such as PS-IPS and PSA-VA, the content of component E is preferably, based on the composition, in the range of approximately 30% by weight or more, and further preferably, in the range of approximately 40% by weight or more.

The polymerizable composition is prepared according to a method for dissolving required components at temperature higher than room temperature, or the like. According to an application, an additive may be added to the composition. Examples of the additives include an optically active compound, an antioxidant, an ultraviolet light absorber and an antifoaming agent. Such additives are well known to those skilled in the art, and are described in literature.

The optically active compound is effective in inducing helical structure to provide liquid crystal molecules with a required twist angle, thereby preventing inverted twist. Addition of the optically active compound allows adjustment of a helical pitch. Two or more optically active compounds may be added thereto for the purpose of adjusting temperature dependence of the helical pitch. Specific preferred examples of the optically active compound include compounds (Op-1) to (Op-18) described below.

In compound (Op-18), ring J is 1,4-cyclohexylene or 1,4-phenylene, and $R^{28}$ is alkyl having 1 to 10 carbons.

(Op-1) 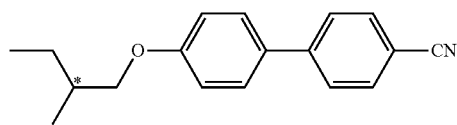

(Op-2) 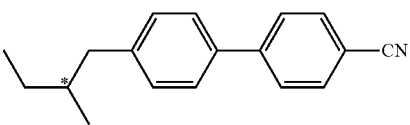

-continued
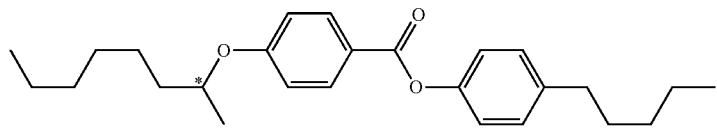
(Op-3)
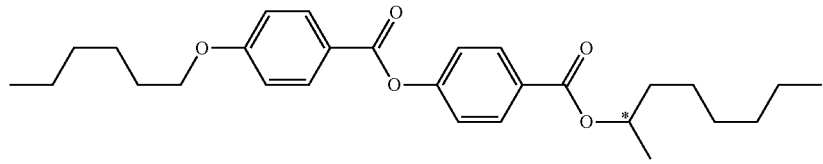
(Op-4)
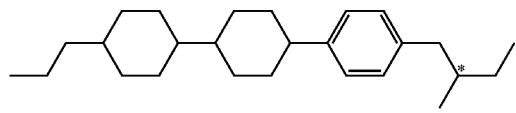
(Op-5)
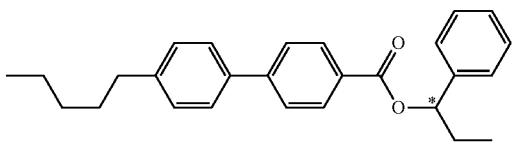
(Op-6)
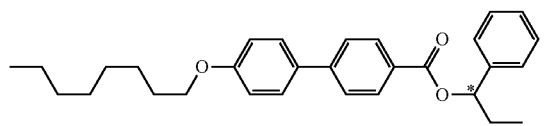
(Op-7)
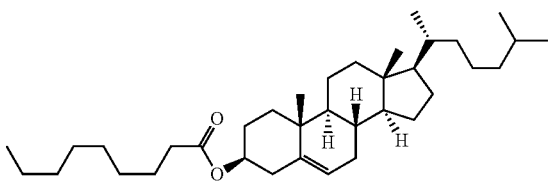
(Op-8)
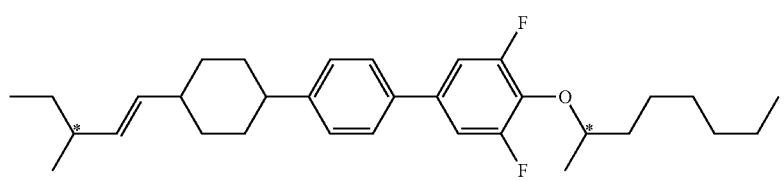
(Op-9)
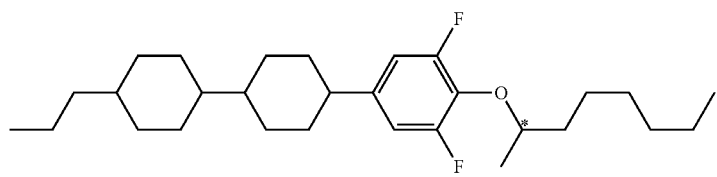
(Op-10)
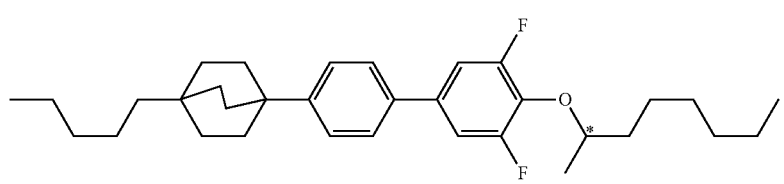
(Op-11)
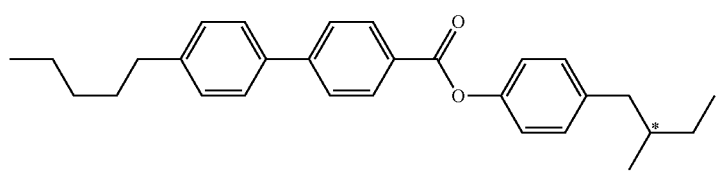
(Op-12)

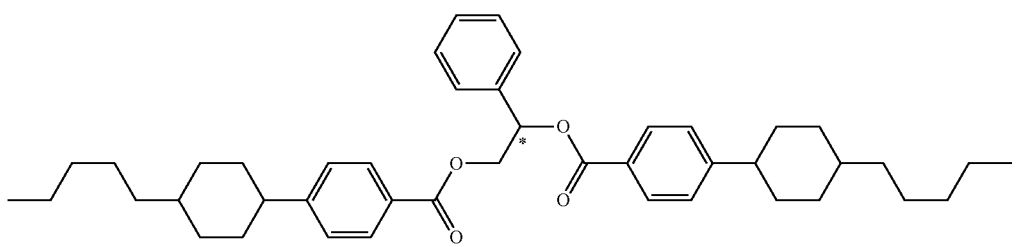
(Op-13)

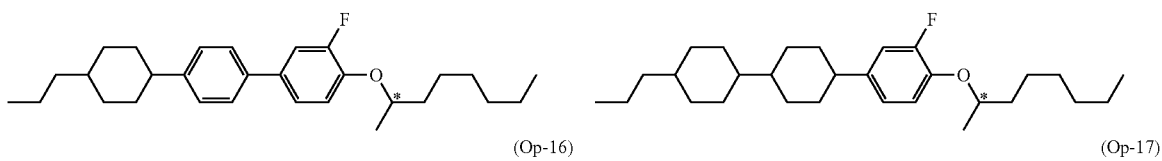
(Op-14) (Op-15)

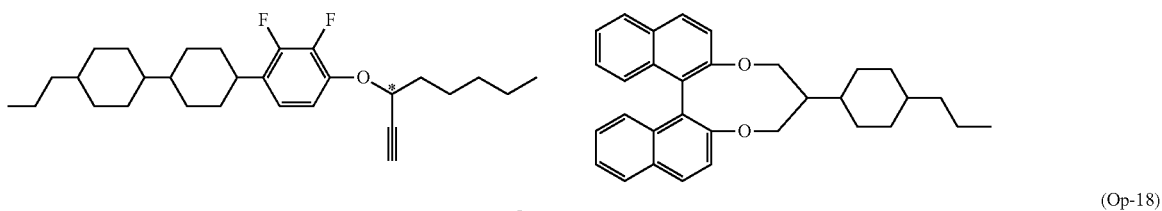
(Op-16) (Op-17)

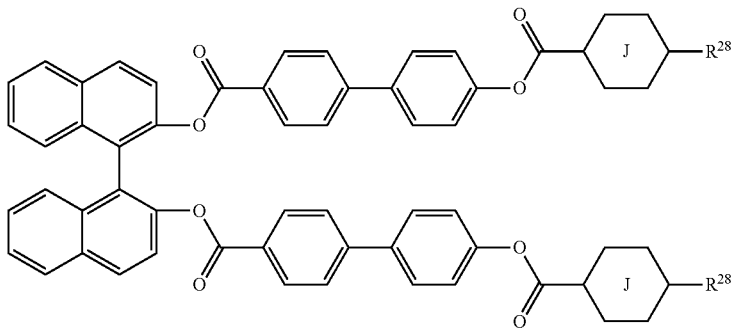
(Op-18)

The antioxidant is effective in order to maintain a large voltage holding ratio. Specific preferred examples of the antioxidants include compound (AO-1) and compound (AO-2) described below, IRGANOX 415, IRGANOX 565, IRGANOX 1010, IRGANOX 1035, IRGANOX 3114 and IRGANOX 1098 (trade name: BASF SE). The ultraviolet light absorber is effective in preventing a decrease in the maximum temperature. Preferred examples of the ultraviolet light absorbers include a benzophenone derivative, a benzoate derivative and a triazole derivative. Specific examples include compounds (AO-3) and (AO-4) described below, TINUVIN 329, TINUVIN P, TINUVIN 326, TINUVIN 234, TINUVIN 213, TINUVIN 400, TINUVIN 328 and TINUVIN 99-2 (trade name: BASF SE) or 1,4-diazabicyclo[2.2.2]octane (DABCO). A light stabilizer such as an amine having steric hindrance is also preferred in order to maintain a large voltage holding ratio. Specific preferred examples of the light stabilizers include compounds (AO-5) and (AO-6) described below, TINUVIN 144, TINUVIN 765 and TINUVIN 770DF (trade name: BASF SE). Moreover, a heat stabilizer is also effective in order to maintain a large voltage holding ratio, and specific preferred examples include IRGAFOS 168 (trade name: BASF SE). The antifoaming agent is effective in order to prevent foam formation. Preferred examples of the antifoaming agent include dimethyl silicone oil and methylphenyl silicone oil.

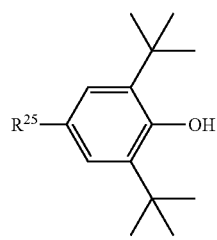
(AO-1)

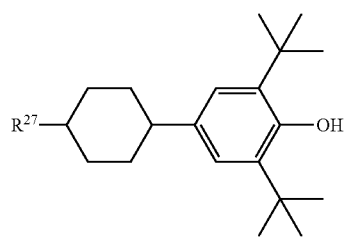
(AO-2)

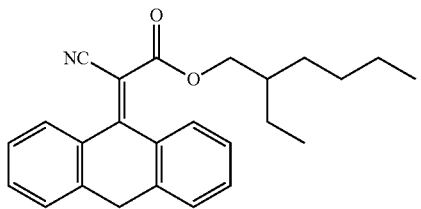

(AO-3)

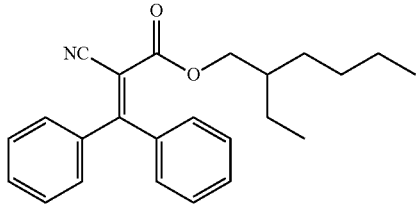

(AO-4)

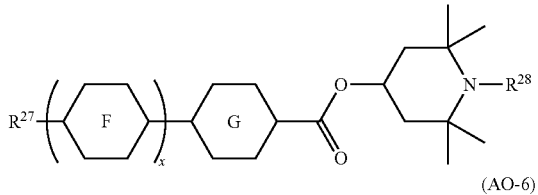

(AO-5)

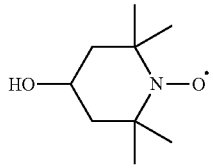

(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$, and R$^{26}$ is alkyl having 1 to 20 carbons, in compound (AO-2) and compound (AO-5), $R^{27}$ is alkyl having 1 to 20 carbons, and in compound (AO-5), ring F and ring G are 1,4-cyclohexylene or 1,4-phenylene, x is 0, 1 or 2, and $R^{28}$ is hydrogen, —CH$_3$ or O. (oxygen radical).

4. Liquid Crystal Composite

Compound (1) has high polymerization reactivity, a high conversion ratio and high solubility in the liquid crystal composition. A liquid crystal composite is formed by polymerizing the polymerizable composition containing compound (1) and the liquid crystal composition. Compound (1) forms the polymer in the liquid crystal composition by polymerization. The polymer is effective in generating pretilt in the liquid crystal molecules. The polymerization is preferably performed at temperature at which the polymerizable composition exhibits the liquid crystal phase. The polymerization progresses by heat, light or the like. A preferred reaction includes photopolymerization. The photopolymerization is preferably performed at 100° C. or lower in order to prevent simultaneous occurrence of thermopolymerization. The polymerization may be allowed in a state in which an electric field or a magnetic field is applied.

The polymerization reactivity and the conversion ratio of compound (1) can be adjusted. Compound (1) is suitable for radical polymerization. Compound (1) can be rapidly polymerized by adding the polymerization initiator. An amount of remaining compound (1) can be reduced by optimizing reaction temperature. Examples of a photoradical polymerization initiator include TPO, and 1173 or 4265 from Darocur series of Ciba Specialty Chemicals Inc., and 184, 369, 500, 651, 784, 819, 907, 1300, 1700, 1800, 1850 or 2959 from Irgacure series.

Additional examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

The polymerization can be performed by adding the photoradical polymerization initiator to the polymerizable composition, and then irradiating the resulting mixture with ultraviolet light in a state in which the electric field is applied. However, an unreacted polymerization initiator or a decomposition product of the polymerization initiator might cause poor display to the device, such as image sticking. In order to prevent such a poor display, photopolymerization may be performed without adding the polymerization initiator. A preferred wavelength of irradiating light is in the range from approximately 150 nanometers to approximately 500 nanometers. A further preferred wavelength is in the range from approximately 250 nanometers to approximately 450 nanometers, and a most preferred wavelength is in the range from approximately 300 nanometers to approximately 400 nanometers.

5. Liquid Crystal Display Device

An effect of the polymer in the liquid crystal display device is interpreted as described below. The polymerizable composition is a mixture of the liquid crystal compound, the polymerizable compound and so forth. Application of the electric field to the composition causes alignment of the liquid crystal molecules in the direction of the electric field. The polymerizable compound is also aligned according to the alignment. The polymerizable compound is polymerized by irradiating the composition with ultraviolet light, while maintaining the alignment, to form three-dimensional network structure. Even when the electric field is removed, the alignment of the polymer is maintained. The liquid crystal molecules are stabilized in a state of being aligned in the direction of the electric field by the effect of the polymer. Accordingly, response time of the device is to be shortened.

The polymerizable composition is preferably polymerized in the display device. One example is as described below. A display device having two glass substrates provided with transparent electrodes and an alignment film is arranged. A polymerizable composition containing compound (1), a liquid crystal composition, an additive and so forth as a component is prepared. The composition is injected into the display device. The display device is irradiated with ultraviolet light while applying the electric field to polymerize compound (1). A liquid crystal composite is formed by the polymerization. A liquid crystal display device having the liquid crystal composite can be easily produced by the method. Rubbing treatment to the alignment film may be omitted in the method. In addition, a method for stabilizing the liquid crystal molecules in a state without the electric field may be adopted.

When the amount of addition of the polymer is the range from approximately 0.1% by weight to approximately 2% by weight based on the liquid crystal composition, a liquid crystal display device having a PSA mode is prepared. The device having the PSA mode can be driven by a driving mode such as active matrix (AM) and passive matrix (PM). Such a device can be applied to any mode, a reflective mode, a transmissive mode and a transflective mode. An increase in the amount of addition of the polymer also allows preparation of a device having a polymer dispersed mode.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples. The invention is not restricted by the Examples.

1. Example of Compound (1)

Compound (1) was synthesized by procedures presented in Example 1 or the like. The compound synthesized was identified by a method such as an NMR analysis. Physical properties of the compound were measured by the method described below.
NMR Analysis As a measuring apparatus, DRX-500 (made by Bruker BioSpin Corporation) was used. In measurement of $^1$H-NMR, a sample was dissolved in a deuterated solvent such as $CDCl_3$, and measurement was carried out under the conditions of room temperature, 500 MHz and 16 times of accumulation. Tetramethylsilane was used as an internal standard. In measurement of $^{19}$F-NMR, $CFCl_3$ was used as an internal standard, and measurement was carried out under the conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and being broad, respectively.
HPLC Analysis As a measuring apparatus, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector and a CORONA detector or the like was appropriately used. When the UV detector was used, a detection wavelength was set at 254 nanometers. A sample was dissolved in acetonitrile to prepare a solution having 0.1% by weight, and 1 microliter of the solution obtained was introduced into a sample injector. As a recorder, C-R7Aplus made by Shimadzu Corporation was used.
Ultraviolet-Visible Spectrophotometry As a measuring apparatus, PharmaSpec UV-1700 made by Shimadzu Corporation was used. A detection wavelength was adjusted in the range from 190 nanometers to 700 nanometers. A sample was dissolved in acetonitrile and prepared to be a solution having 0.01 millimole per liter, and measurement was carried out by putting the solution in a quartz cell (optical path length 1 cm).
Sample for Measurement When measuring phase structure and transition temperature (a clearing point, a melting point, polymerization starting temperature, or the like), a compound itself was used as a sample. When measuring physical properties such as a maximum temperature of a nematic phase, viscosity, optical anisotropy and dielectric anisotropy, a mixture of a compound and a base liquid crystal was used as a sample.
Measurement Method Physical properties were measured by the method described below. Most of the measurement methods are applied as described in the Standard of the Japan Electronics and Information Technology Industries Association (hereinafter, abbreviated as JEITA) JEITA (JEITA ED-2521B) discussed and established by JEITA, or modified thereon. No thin film transistor (TFT) was attached to a TN device used for measurement.
(1) Phase Structure A sample was placed on a hot plate in a melting point apparatus equipped with a polarizing microscope (FP-52 Hot Stage made by Mettler-Toledo International Inc.), a state of phase and a change thereof were observed by the polarizing microscope while heating the sample at a rate of 3° C. per minute, and a type of phase was specified.
(2) Transition Temperature (° C.)

Measurement was carried out using a differential scanning calorimeter, Diamond DSC System, made by PerkinElmer, Inc., or a high-sensitivity differential scanning calorimeter, X-DSC7000, made by SII NanoTechnology Inc. A sample was heated and then cooled at a rate of 3° C. per minute, and a starting point of an endothermic peak or an exothermic peak caused by a phase change of the sample was determined by extrapolation, and thus a transition temperature was determined Temperature at which a compound transits from a solid to a liquid crystal phase such as a smectic phase and a nematic phase may be occasionally abbreviated as "minimum temperature of the liquid crystal phase." Temperature at which a compound transits from the liquid crystal phase to a liquid may be occasionally abbreviated as "clearing point." A melting point and a polymerization starting temperature were also measured using the apparatus.

The crystal was expressed as C. When kinds of the crystals were further distinguishable, each of the crystals was expressed as $C_1$ or $C_2$. The smectic phase was expressed as S and the nematic phase as N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. The transition temperature was expressed, for example, as "C 50.0 N 100.0 I." The expression shows that a transition temperature from the crystal to the nematic phase is 50.0° C., and a transition temperature from the nematic phase to the liquid is 100.0° C.
(3) Maximum Temperature of a Nematic Phase ($T_{NI}$ or NI; ° C.)

A sample was placed on a hot plate of a melting point apparatus equipped with a polarizing microscope, and heated at a rate of 1° C. per minute. Temperature when part of the sample changed from the nematic phase to the isotropic liquid was measured. When the sample was a mixture of the compound and the base liquid crystal, the maximum temperature was expressed using a symbol of $T_{NI}$. When the sample was a mixture of the compound and component B, C, D or E, the maximum temperature was expressed using a symbol of NI.
(4) Minimum Temperature of a Nematic Phase ($T_c$; ° C.)

Samples each having a nematic phase were kept in freezers at 0° C., −10° C., −20° C., −30° C. and −40° C. for 10 days, and then liquid crystal phases were observed. For example, when a sample maintained the nematic phase at −20° C. and changed to a crystal or a smectic phase at −30° C., $T_c$ was expressed as $T_c \leq -20°$ C.

(5) Viscosity (Bulk Viscosity; η; Measured at 20° C.; mPa·s)

Viscosity was measured using a cone-plate (E type) rotational viscometer, made by Tokyo Keiki Inc.

(6) Optical Anisotropy (Refractive Index Anisotropy; Measured at 25° C.; Δn)

Measurement was carried out by an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥–n⊥.

(7) Specific Resistance (ρ; Measured at 25° C.; Ωcm)

Into a container provided with electrodes, 1.0 mL of sample was injected. Direct current voltage (10 V) was applied to the container, and a direct current after 10 seconds was measured. The specific resistance was calculated from an expression described below.

(Specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the device and the device was charged. A decaying voltage was measured for 16.7 milliseconds with a high-speed voltmeter, and area A between a voltage curve and a horizontal axis in a unit cycle was determined Area B is an area without decay. A voltage holding ratio is a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The results obtained were presented using a symbol of VHR-2.

Methods for measuring physical properties may be occasionally different between a sample having positive dielectric anisotropy and a sample having negative dielectric anisotropy. Then, measurement methods when dielectric anisotropy is positive are presented in (10-1) to (14-1). When the dielectric anisotropy is negative, the methods are presented in (10-2) to (14-2).

(10-1) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. Voltage was stepwise applied to the device in the range from 16 V to 19.5 V at an increment of 0.5 V. After a period of 0.2 second with no voltage application, application was repeated under conditions of only one of rectangular waves (rectangular pulse; 0.2 second) and no application (2 seconds). A peak current and a peak time of a transient current generated by the application were measured. A value of rotational viscosity was obtained from the measured values according to calculating equation (8) on page 40 of the paper by Imai et al. A value of dielectric anisotropy necessary for the calculation was determined by using the device used for measuring the rotational viscosity according to the method as described below.

(11-1) Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in the major axis direction of liquid crystal molecules was measured. Sine waves (0.5 V, 1 kHz) were applied to the device, and after 2 seconds, a dielectric constant (∈⊥) in the minor axis direction of the liquid crystal molecules was measured. A value of dielectric anisotropy was calculated from an equation: Δ∈=∈∥–∈⊥.

(12-1) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge from 0 V to 20 V was applied to the device, and electrostatic capacity and applied voltage were measured. Measured values of the electrostatic capacity (C) and the applied voltage (V) were fitted to equation (2.98) and equation (2.101) on page 75 of "Liquid Crystal Device Handbook" (Ekisho Debaisu Handobukku in Japanese) (The Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171 of the same Handbook. An elastic constant K is expressed using a mean value of the thus determined $K_{11}$, $K_{22}$ and $K_{33}$.

(13-1) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. Voltage (32 Hz, rectangular waves) to be applied to the device was stepwise increased from 0 V to 10 V at an increment of 0.02 V. On the occasion, the device was irradiated with light from a direction perpendicular to the device, and the amount of light transmitted through the device was measured. A voltage-transmittance curve was prepared, in which the maximum amount of light corresponds to 100% transmittance and the minimum amount of light corresponds to 0% transmittance. A threshold voltage is a voltage at 90% transmittance.

(14-1) Response Time (τ; Measured at 25° C.; Ms)

An LCD-5100 luminance meter made by Otsuka Electronics Co., Ltd. was used for measurement. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5 v, 0.5 second) were applied to the device. On the occasion, the device was irradiated with light from a direction perpendicular to the device, and the amount of light transmitted through the device was measured. A maximum amount of light corresponds to 100% transmittance, and a minimum amount of light corresponds to 0% transmittance. A rise time (τr: rise time; millisecond) is a period of time required for the change in transmittance from 90% to 10%. A fall time (τf: fall time; millisecond) is a period of time required for the change in transmittance from 10% to 90%. The response time was expressed by a sum of the rise time and the fall time thus obtained.

(10-2) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a VA device in which a distance (cell gap) between two glass substrates was 20 micrometers. Voltage was stepwise applied to the device in the range from 30 V to 50 V at an increment of 1 V. After a period of 0.2 second with no voltage application, application was repeated under conditions of only one of rectangular waves (rectangular pulse; 0.2 second) and no application (2 seconds). A peak current and a peak time of a transient current generated by the application were measured. A value of rotational viscosity was obtained from the measured values according to calculating equation (8) on page 40 of the paper by Imai et al. As a value of dielectric anisotropy necessary for the calculation, a value measured in the section of dielectric anisotropy described below was used.

(11-2) Dielectric Anisotropy (Δ∈; Measured at 25° C.)

A value of dielectric anisotropy was calculated from an equation: Δ∈=∈||−∈⊥. A dielectric constant (∈|| and ∈⊥) was measured as described below.

(1) Measurement of dielectric constant (∈||): An ethanol (20 mL) solution of octadecyl triethoxysilane (0.16 mL) was applied to a well-cleaned glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈||) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(12-2) Elastic Constant ($K_{11}$ and $K_{33}$; Measured at 25° C.; pN)

Elastic Constant Measurement System Model EC-1 made by TOY(O)Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(13-2) Threshold Voltage (Vth; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) applied to the device was increased stepwise from 0 V to 20 V at an increment of 0.02 V. On the occasion, the device was irradiated with light from a direction perpendicular to the device, and an amount of light transmitted through the device was measured.

A voltage-transmittance curve was prepared, in which the maximum value of the amount of light corresponded to 100% transmittance and the minimum value of the amount of light corresponded to 0% transmittance. A threshold voltage was expressed by a voltage at 10% transmittance.

(14-2) Response Time (τ; Measured at 25° C.; Ms)

An LCD-5100 luminance meter made by Otsuka Electronics Co., Ltd. was used for measurement. A light source was a halogen lamp. A low-pass filter was set to 5 kHz. A sample was put in a normally black mode PVA device in which a distance (cell gap) between two glass substrates was 3.2 micrometers and a rubbing direction was anti-parallel, and the device was sealed using an ultraviolet-curable adhesive. A voltage having a degree a little over a threshold voltage was applied to the device for 1 minute, and then the device was irradiated with ultraviolet light having 23.5 mW/cm² for 8 minutes while applying a voltage of 5.6 V. Rectangular waves (60 Hz, 10 V, 0.5 second) were applied to the device. On the occasion, the device was irradiated with light from a direction perpendicular to the device, and the amount of light transmitted through the device was measured. A maximum amount of light corresponds to 100% transmittance, and a minimum amount of light corresponds to 0% transmittance. A response time was expressed by a period of time required for the change in transmittance from 90% to 10% (fall time; millisecond).

Example 1

Synthesis of Compound (No. 1): furan-2,5-diylbis(4,1-phenylene)bis(2-methylacrylate)

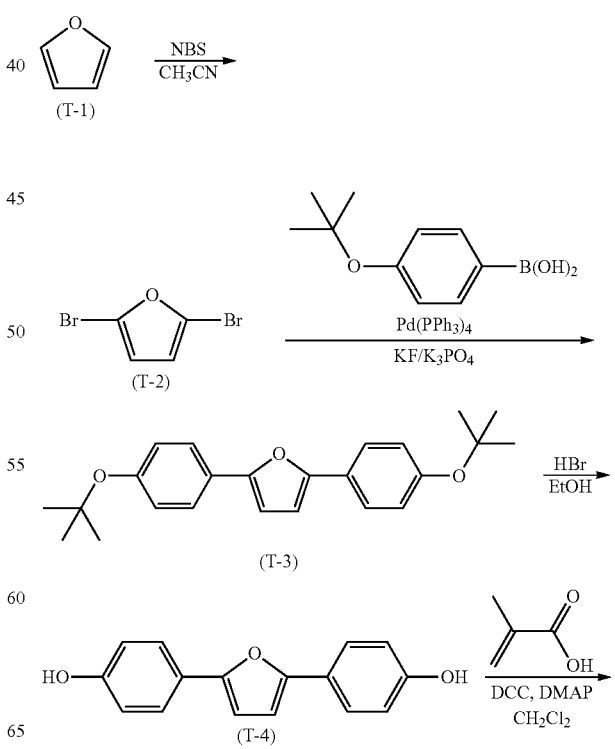

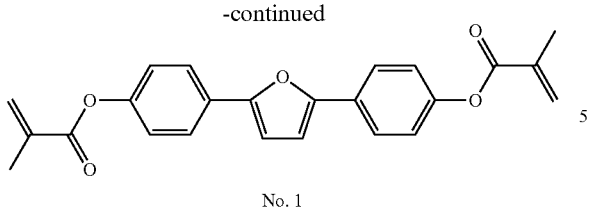

No. 1

First Step:

To an acetonitrile (100 mL) solution of furan (T-1) (15.0 g, 0.22 mol), an acetonitrile (300 mL) solution of N-bromosuccinimide (NBS) (82.0 g, 0.461 mol) was added dropwise at 25° C., and the resulting mixture was stirred at 25° C. for 3 hours. The resulting reaction mixture was concentrated under reduced pressure, and then dichloromethane (200 mL) was added thereto, and filtrated. The resulting filtrate was washed with water (150 mL), dried over anhydrous magnesium sulfate, and concentrated under reduced pressure. The resulting residue was purified by column chromatography (eluted by hexane) to give compound (T-2) (16.0 g, 0.071 mol, 32.2%).

Second Step:

A mixture of compound (T-2) (10.0 g, 0.043 mol), 4-t-butoxyphenylboronic acid (17.0 g, 0.088 mol, Pd(PPh$_3$)$_4$ (1.0 g), potassium fluoride (10.0 g, 0.172 mol), K$_3$PO$_4$ (19.0 g, 0.090 mol) and ethanol (300 mL) was refluxed for 2 hours. The resulting reaction mixture was cooled to 40° C., and then filtrated, and the resulting filtrate was concentrated under reduced pressure. The resulting residue was purified by column chromatography (hexane:ethyl acetate=5:1 (volume ratio)), and recrystallized from ethanol to give compound (T-3) (9.0 g, 0.0247 mol, 55.8%).

Third Step:

A mixture of compound (T-3) (9.0 g, 0.0247 mol), ethanol (200 mL) and 40% HBr (50.0 g, 0.247 mol) was stirred overnight. Water (200 mL) was added to the reaction mixture, and the resulting mixture was neutralized by an aqueous solution of sodium hydroxide. Ethanol was distilled off under reduced pressure, and then filtration was made. The resulting residue on a filter paper was washed with water (100 mL) and hexane (100 mL) to give compound (T-4) (6.0 g, 0.0238 mol, 96.3%).

Fourth Step:

Compound (T-4) (5.5 g, 0.022 mol), methacrylic acid (4.5 g, 0.052 mol), N,N-dimethyl-4-aminopyridine (DMAP) (0.3 g, 0.002 mol) and BHT (0.2 g) were dissolved into methylene chloride (150 mL), and the resulting mixture was ice-cooled. A methylene chloride (50 mL) solution of dicyclohexylcarbodiimide (DCC) (11.0 g, 0.053 mol) was added dropwise to the solution over 2 hours. The resulting mixture was stiffed at room temperature for 3 hours. The resulting reaction mixture was quenched with water, and filtrated. The resulting residue on a filter paper was washed with methylene chloride (50 mL×2), and the resulting filtrate was concentrated under reduced pressure. The resulting residue was purified by column chromatography (hexane:ethyl acetate=15:1 (volume ratio)) to give compound (No. 1): furan-2,5-diylbis(4,1-phenylene)bis(2-methylacrylate) (4.5 g, 0.012 mol, 53.1%).

$^1$H-NMR (δ ppm; CDCl$_3$): 7.78 (d, J=4.4 Hz, 2H×2), 7.21 (d, J=4.4 Hz, 2H×2), 6.74 (s, 2H), 6.40 (s, 1H×2), 5.80 (t, J=1.5 Hz, 1H×2), 2.11 (s, 3H×2).

Physical properties of compound (No. 1) were as described below. Melting point: 158° C., polymerization starting temperature: 193° C.

Example 2

Synthesis of Compound (No. 228): (1,3,4-oxadiazole-2,5-diyl)bis(4,1-phenylene)bis(2-methylacrylate)

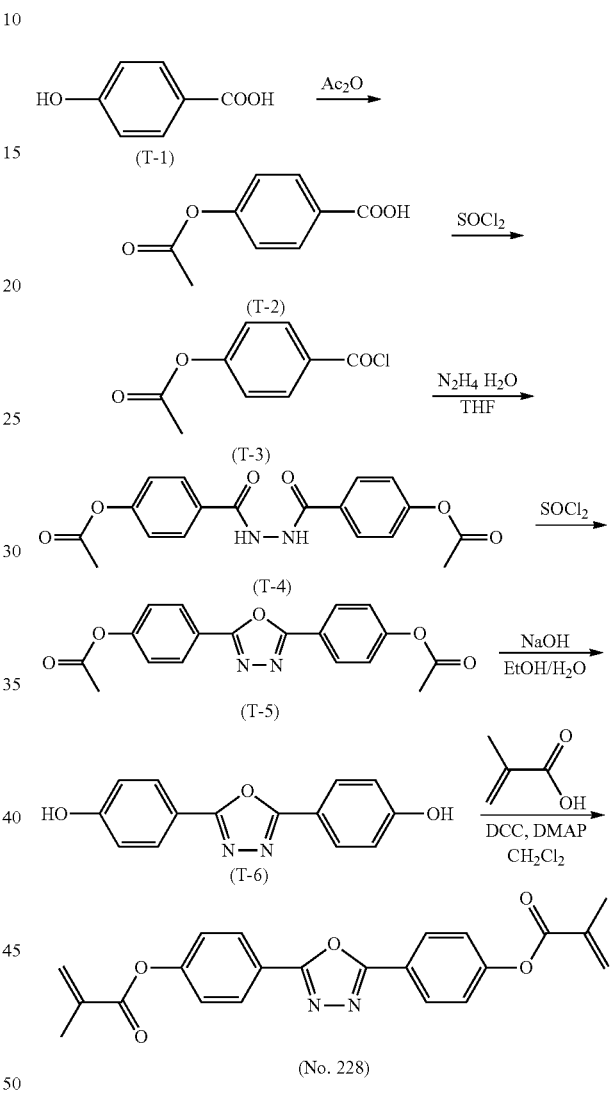

First Step:

Compound (T-1) (60.0 g, 0.434 mol) and sulfuric acid (0.8 mL) were dissolved into acetic anhydride (250 mL), and the resulting mixture was stirred at 25° C. for 12 hours. Water (600 mL) was added, and then the resulting mixture was filtrated. The resulting residue on a filter paper was washed with water (500 mL), and then dried to give compound (T-2) (65.2 g, 0.362 mol, 83.3%).

Second Step:

A mixture of compound (T-2) (55.0 g, 0.305 mol), DMF (0.1 mL) and SOCl$_2$ (250 mL) was refluxed for 4 hours. SOCl$_2$ was distilled off to give compound (T-3). To a THF (400 mL) solution of compound (T-3), 85% hydrazine monohydrate (9.0 g, 0.153 mol) was added dropwise over 1 hour at 0° C. After completion of dropwise addition, the resulting mixture was stirred at room temperature for 10 hours, and filtrated. The resulting residue on a filter paper was washed with methylene chloride (100 mL) to give compound (T-4) (25.0 g, 0.070 mol, 46.0%).
Third Step:

Compound (T-4) (25.0 g, 0.070 mol) and $SOCl_2$ (150 mL) were refluxed for 9 hours. $SOCl_2$ was distilled off, and then water (10 mL) and THF (200 mL) were added thereto, and the resulting mixture was filtrated. The resulting residue on a filter paper was washed with ethanol (50 mL), and dried to give compound (T-5) (14.0 g). The compound was suspended into ethanol (100 mL), a 10% sodium hydroxide aqueous solution (74 g) was added thereto, and then the resulting mixture was stirred at 25 to 30° C. for 2 hours. Ethanol was distilled off, and then the resulting mixture was neutralized with hydrochloric acid. After filtration, the resulting residue was dried to give compound (T-6) (8.0 g, 0.031 mol, 44.9%).
Fourth Step:

Compound (T-6) (8.0 g, 0.031 mol), methacrylic acid (6.0 g, 0.070 mol), N,N-dimethyl-4-aminopyridine (DMAP) (0.43 g, 0.004 mol) and BHT (0.2 g) were dissolved into methylene chloride (150 mL), and the resulting mixture was ice-cooled. A methylene chloride (50 mL) solution of dicyclohexylcarbodiimide (DCC) (16.0 g, 0.078 mol) was added dropwise to the solution over 2 hours, and then the resulting mixture was stirred at room temperature for 3 hours. The reaction mixture was quenched with water, and filtrated. The resulting residue on a filter paper was washed with methylene chloride (50 mL×2), and the resulting filtrate was concentrated under reduced pressure. The resulting residue was purified by column chromatography (hexane:ethyl acetate=15:1 (volume ratio)) to give compound (No. 228): (1,3,4-oxadiazole-2,5-diyl)bis(4,1-phenylene)bis(2-methylacrylate) (8.0 g, 0.020 mol, 65.1%).

$^1$H-NMR (δ ppm; $CDCl_3$): 8.19 (d, J=4.4 Hz, 2H×2), 7.33 (d, J=4.4 Hz, 2H×2), 6.40 (s, 1H×2), 5.82 (t, J=1.2 Hz, 1H×2), 2.09 (s, 3H×2).

Physical properties of compound (No. 228) were as described below. Melting point: 159.0° C., polymerization starting temperature: 162° C.

Compound (No. 1) to compound (No. 243) shown below can be prepared with reference to the experiment operations described in Example 1 and Example 2 and "2. synthesis method."

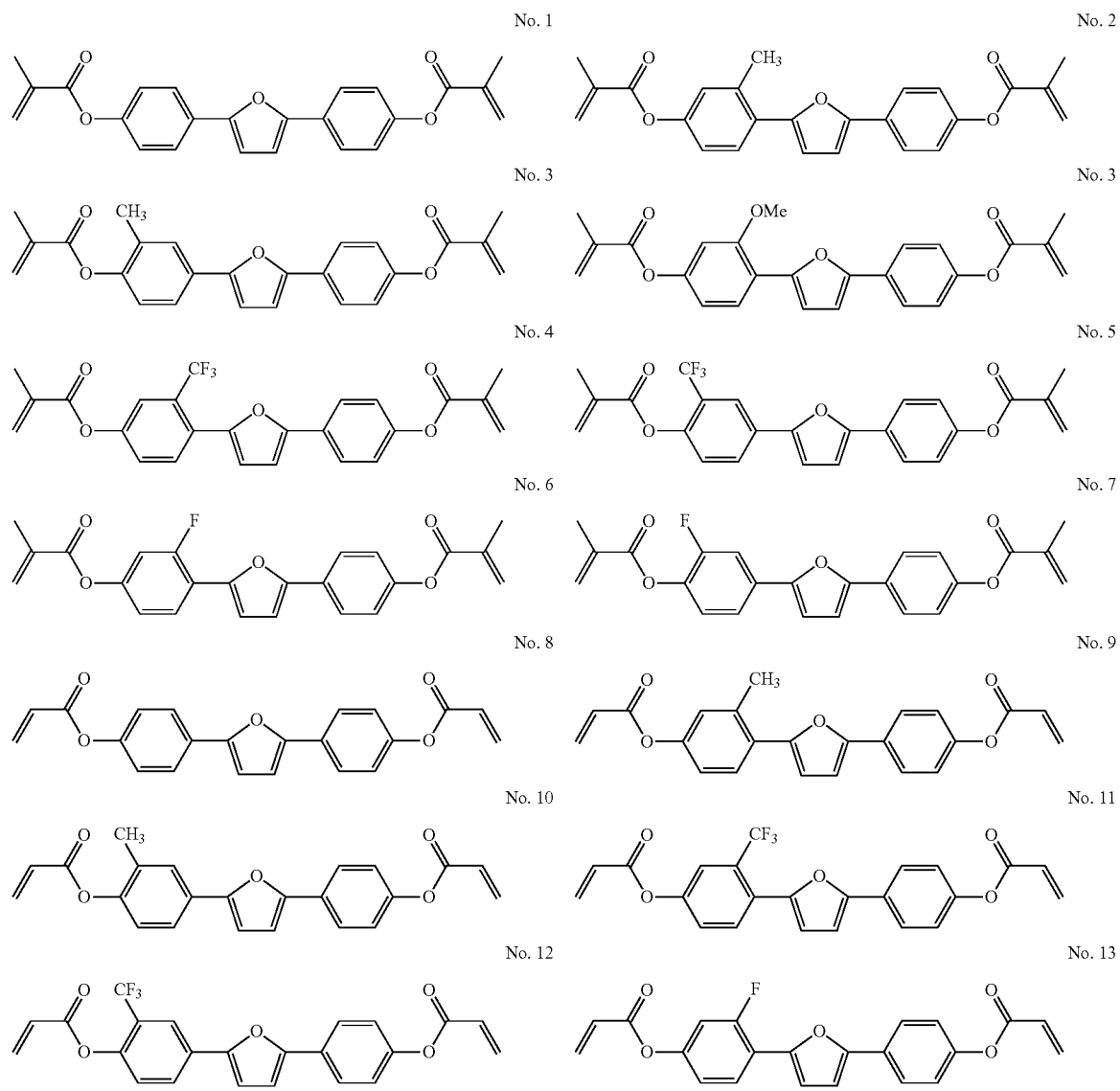

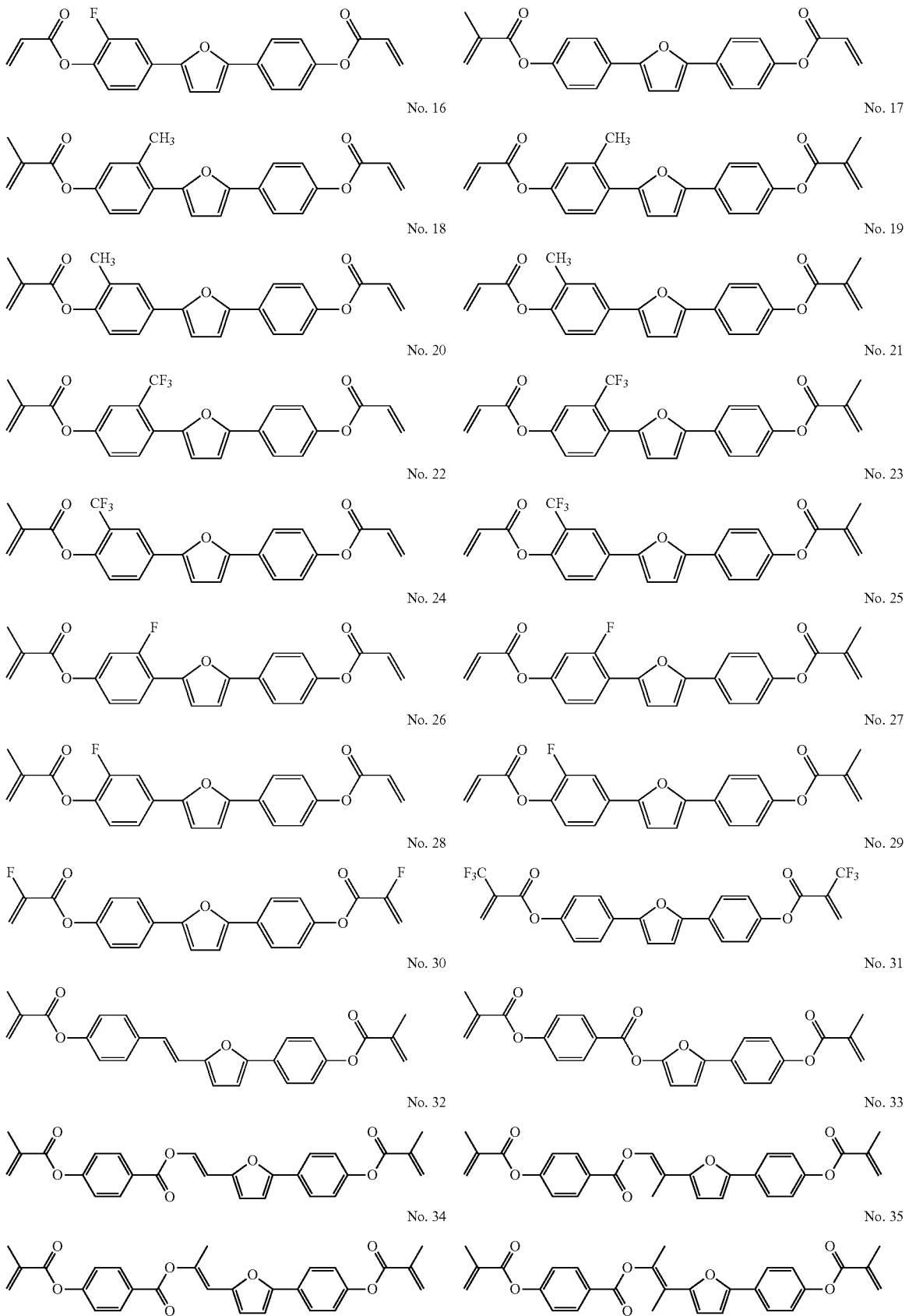

-continued
No. 36
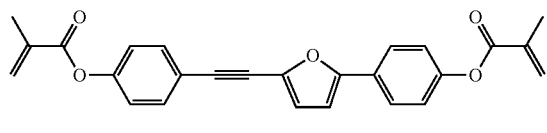
No. 37
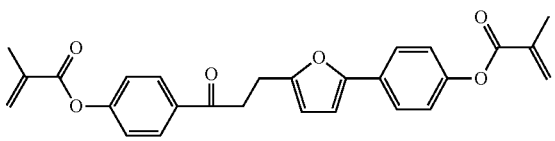
No. 38
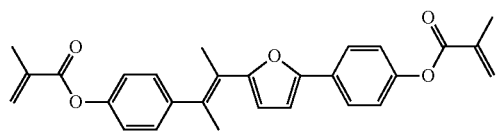
No. 39
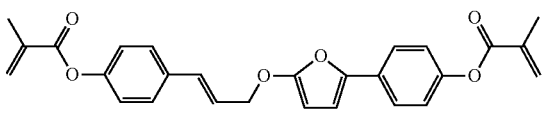
No. 40
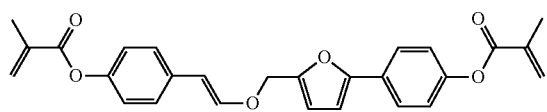
No. 41
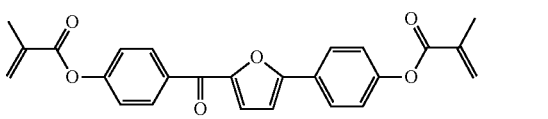
No. 42
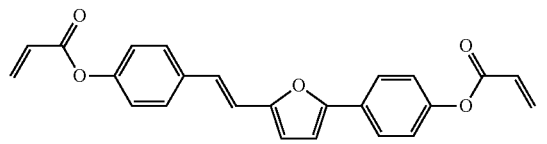
No. 43
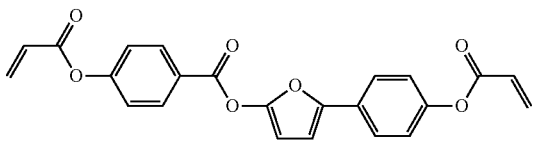
No. 44
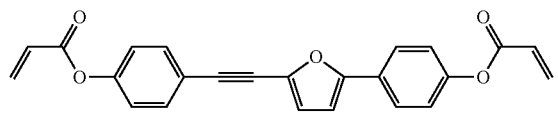
No. 45
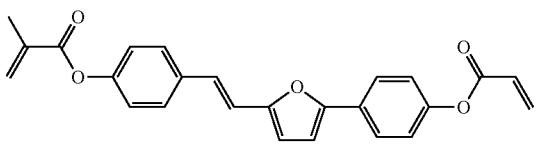
No. 46
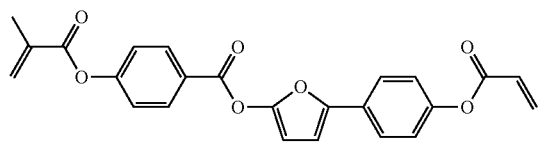
No. 47
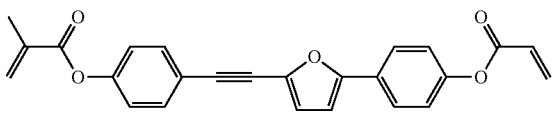
No. 48
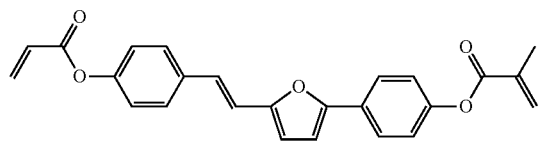
No. 49
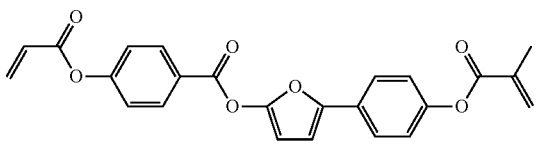
No. 50
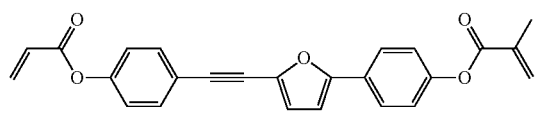
No. 51
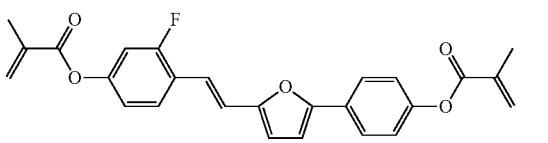
No. 52
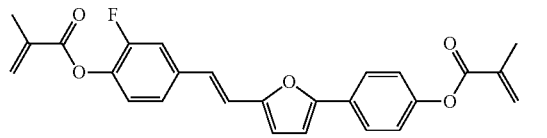
No. 53
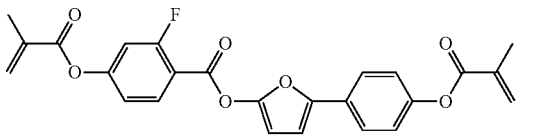

-continued
No. 54
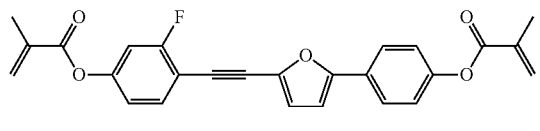
No. 55
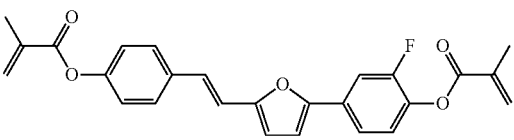
No. 56
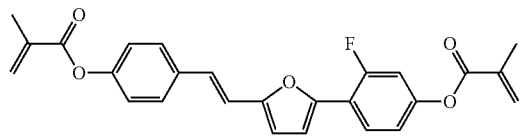
No. 57
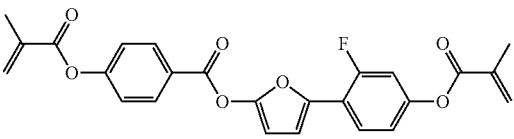
No. 58
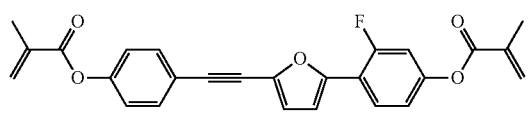
No. 59
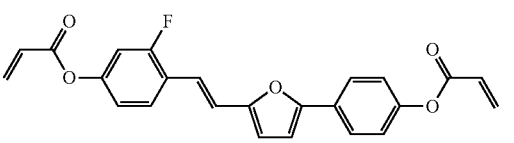
No. 60
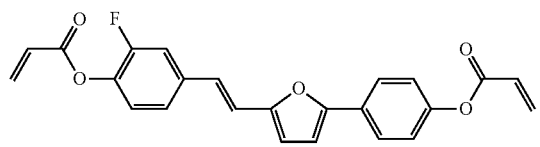
No. 61
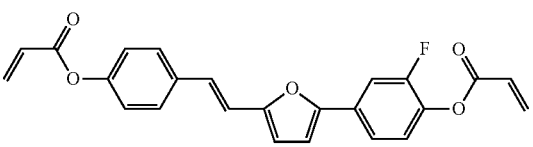
No. 62
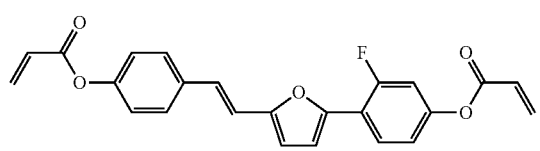
No. 63
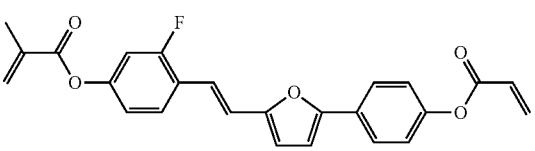
No. 64
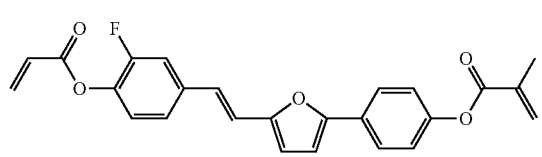
No. 65
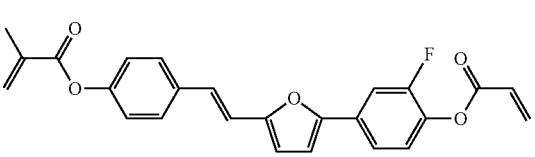
No. 66
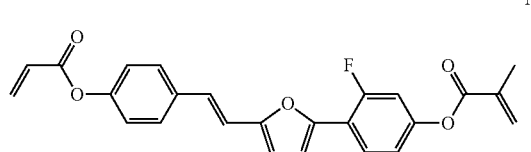
No. 67
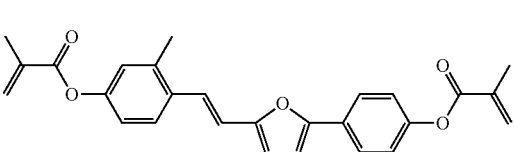
No. 68
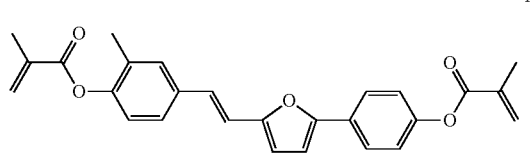
No. 69
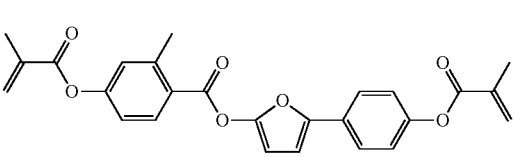
No. 70
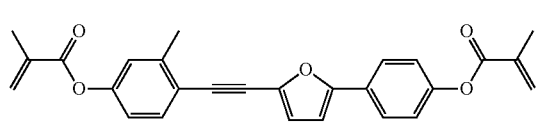
No. 71
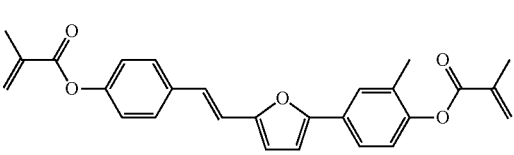

No. 72
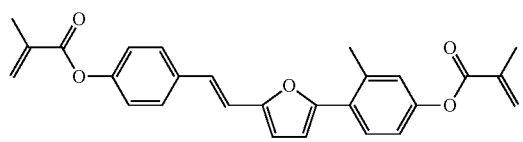
No. 73
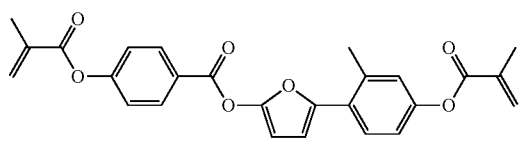
No. 74
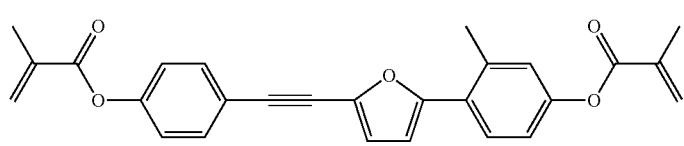
No. 75
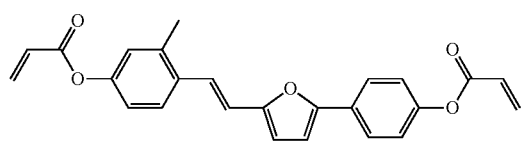
No. 76
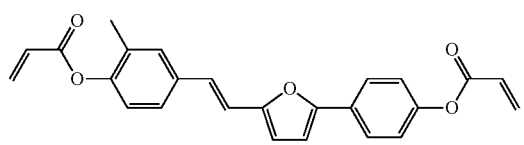
No. 77
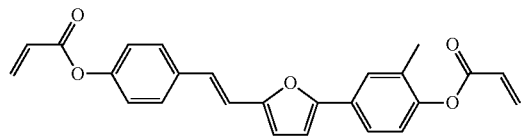
No. 78
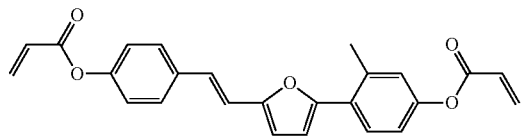
No. 79
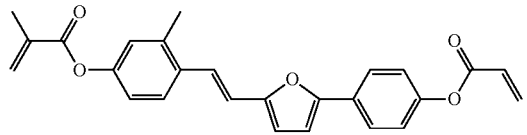
No. 80
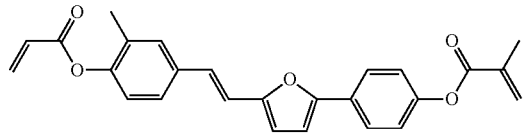
No. 81
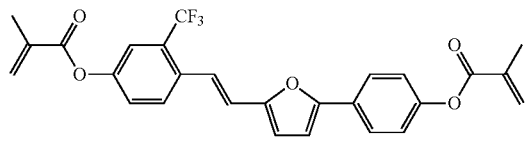
No. 82
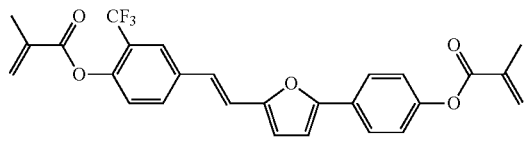
No. 83
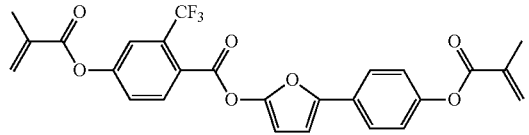
No. 84
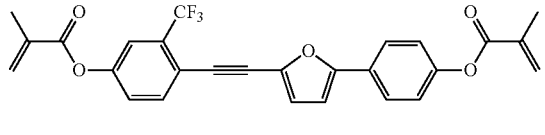
No. 85
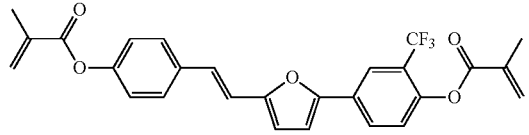
No. 86
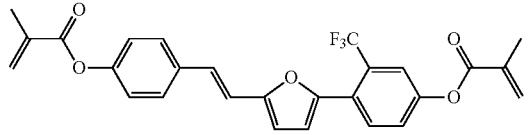

-continued
No. 89
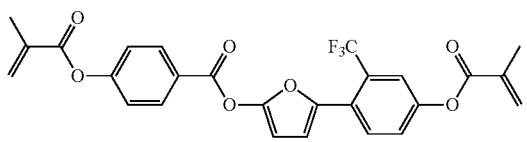
No. 90
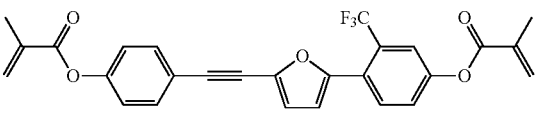
No. 91
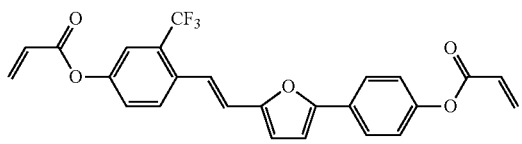
No. 92
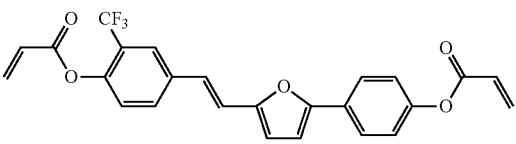
No. 93
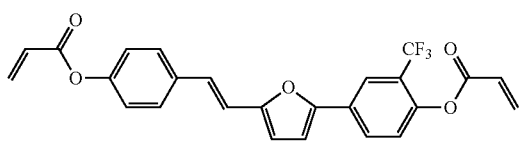
No. 94
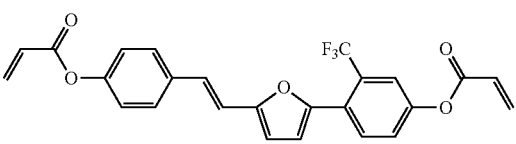
No. 95
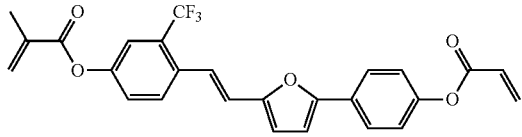
No. 96
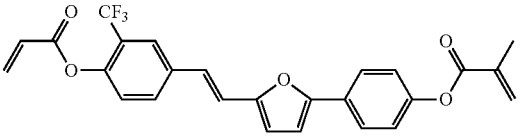
No. 97
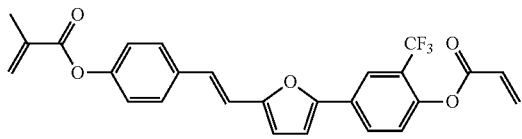
No. 98
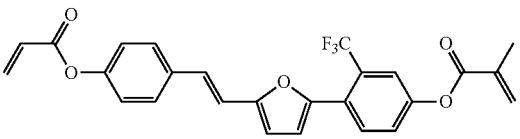
No. 99
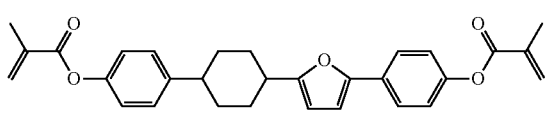
No. 100
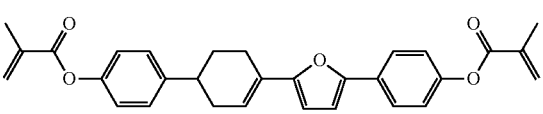
No. 101
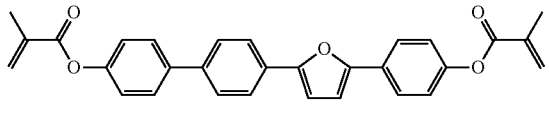
No. 102
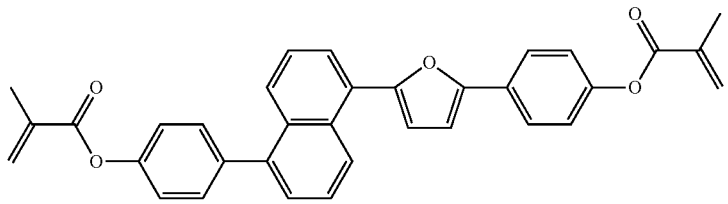
No. 103
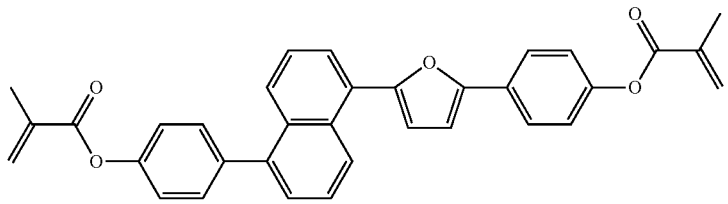
No. 104
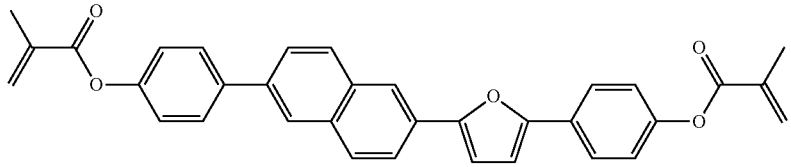

-continued
No. 105
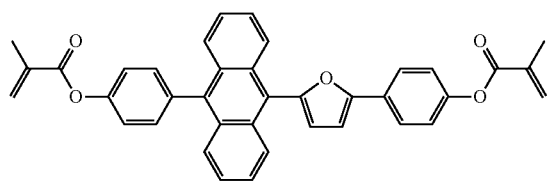
No. 106
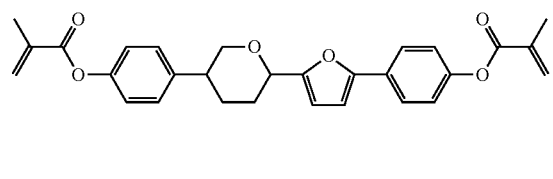
No. 107
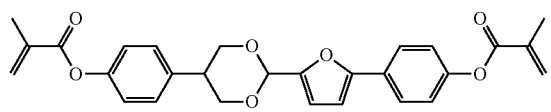
No. 108
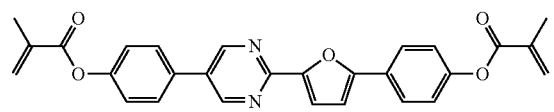
No. 109
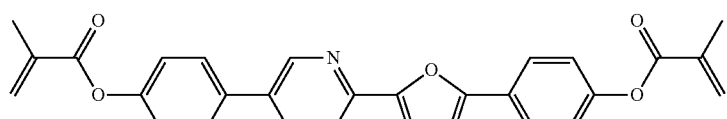
No. 110
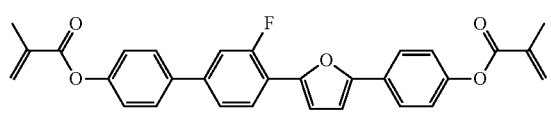
No. 111
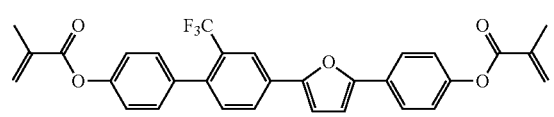
No. 112
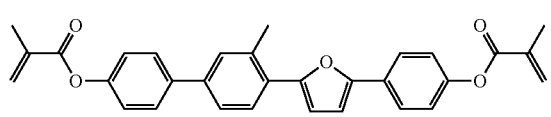
No. 113
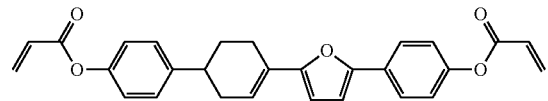
No. 114
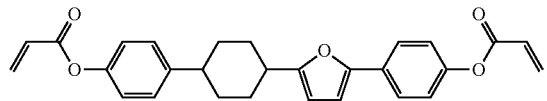
No. 115
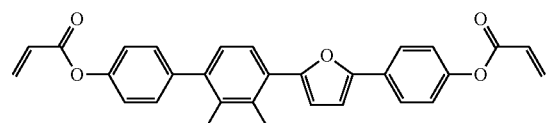
No. 116
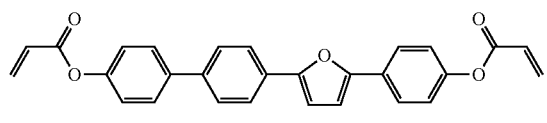
No. 117
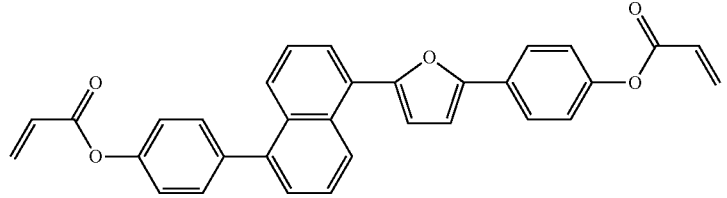
No. 118
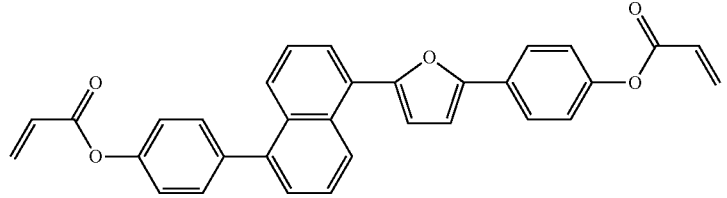
No. 119
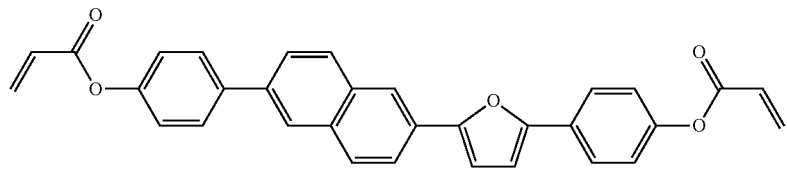

-continued
No. 120
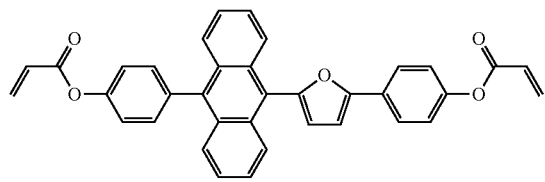
No. 121
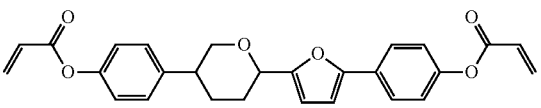
No. 122
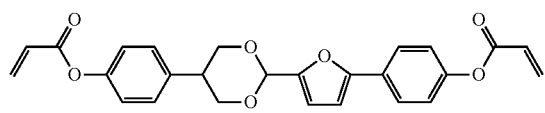
No. 123
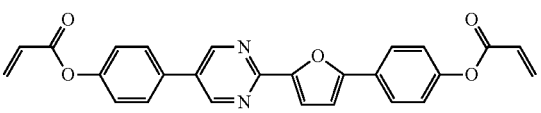
No. 124
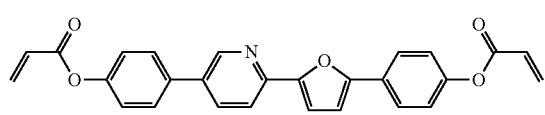
No. 125
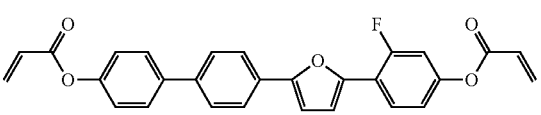
No. 126
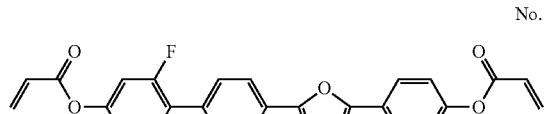
No. 127
No. 128
No. 129
No. 130
No. 131
No. 132
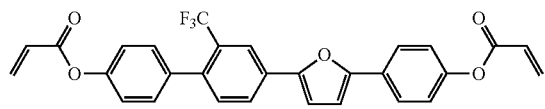
No. 133
No. 134
No. 135
No. 136
No. 137

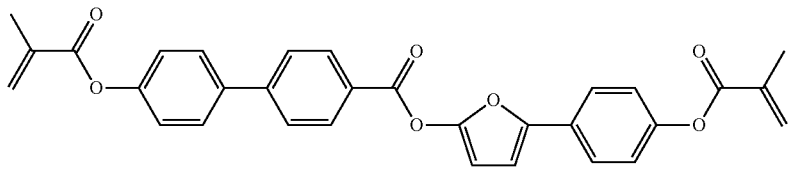
No. 138
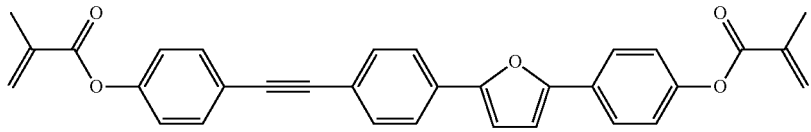
No. 139
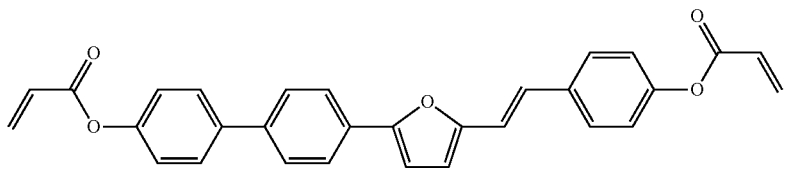
No. 140
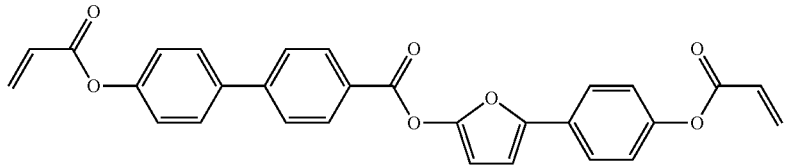
No. 141
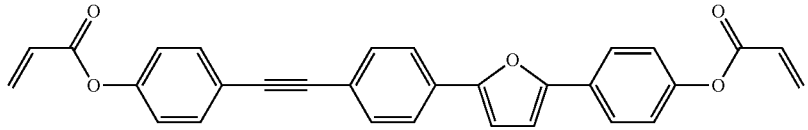
No. 142
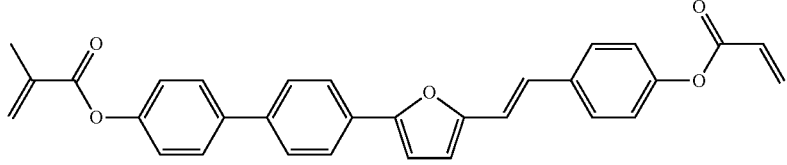
No. 143
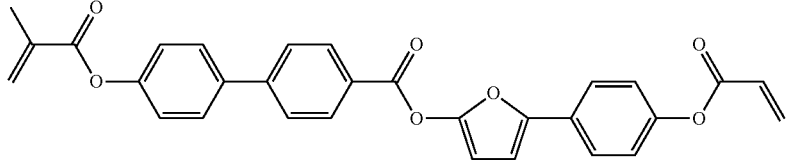
No. 144
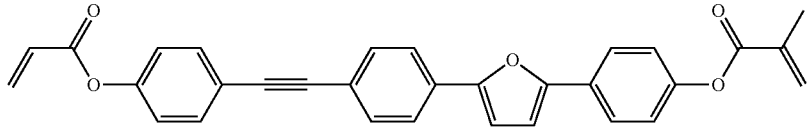
No. 145
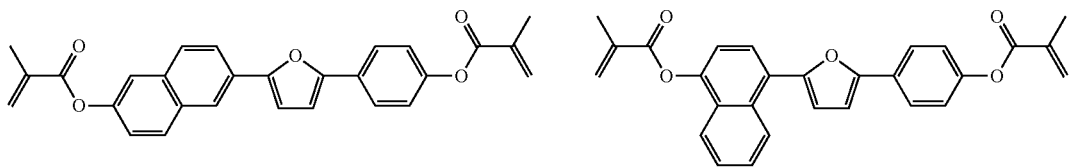
No. 146                                     No. 147

-continued
No. 148
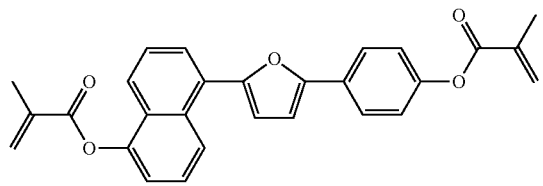
No. 149
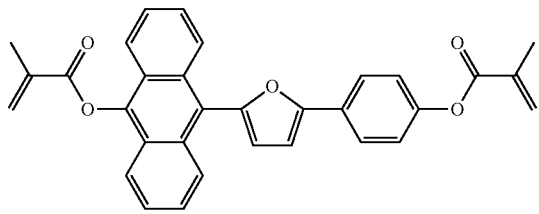
No. 150
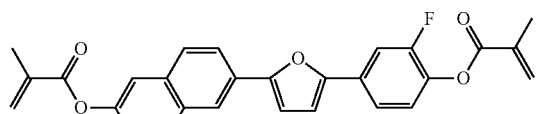
No. 151
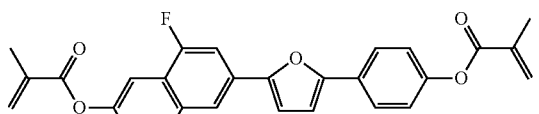
No. 152
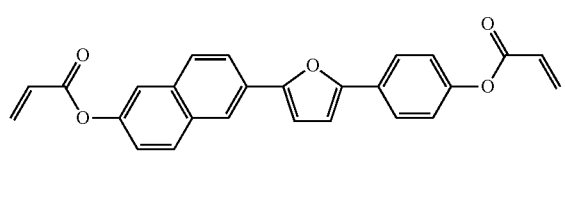
No. 153
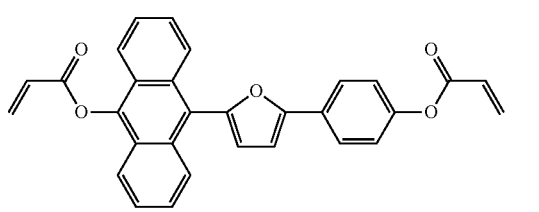
No. 154
No. 155
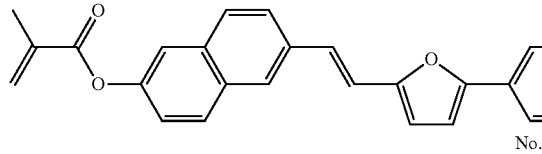
No. 156
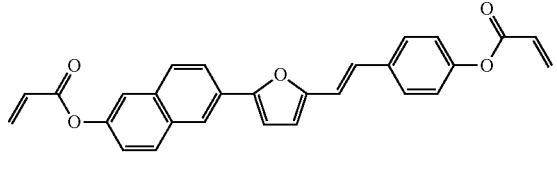
No. 157
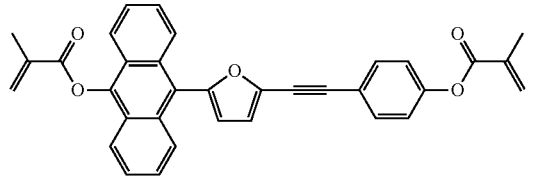
No. 158
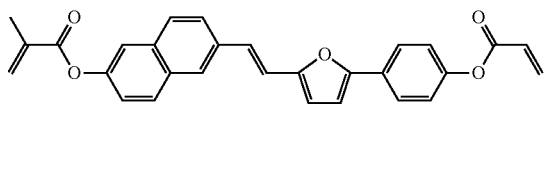
No. 159
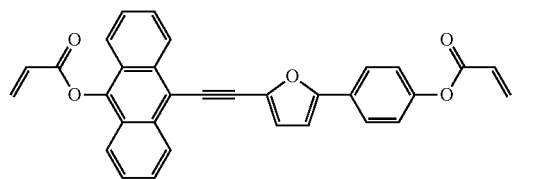
No. 160
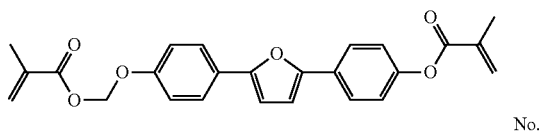
No. 161
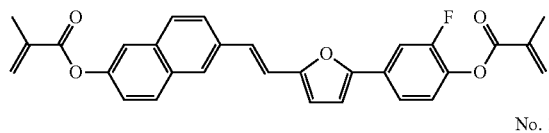
No. 162
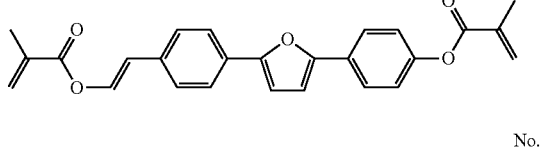
No. 163
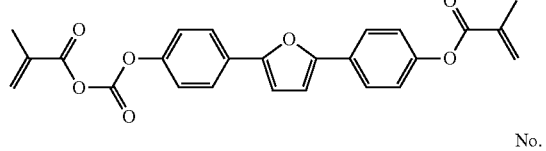
No. 164
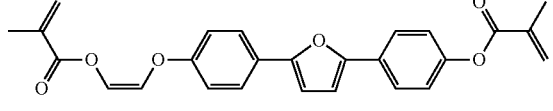
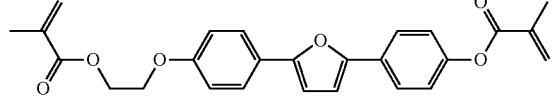

-continued
No. 165
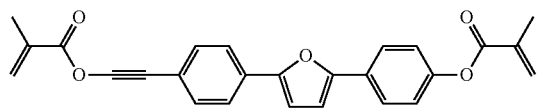
No. 166
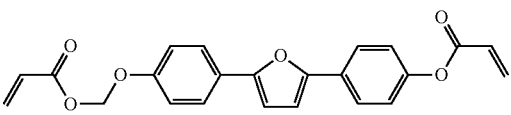
No. 167
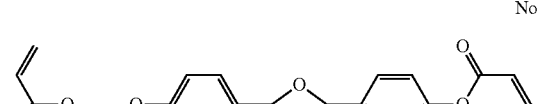
No. 168
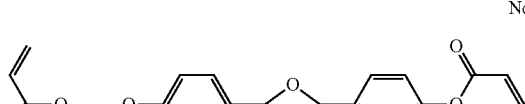
No. 169
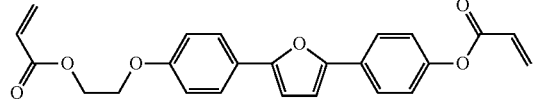
No. 170
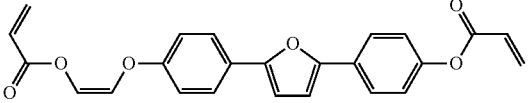
No. 171
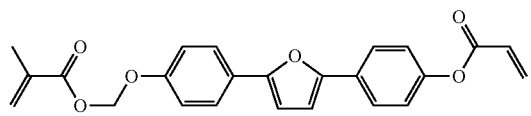
No. 172
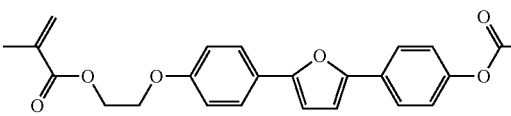
No. 173
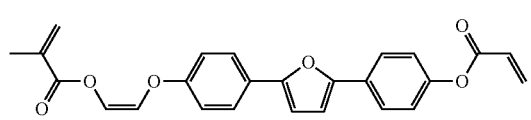
No. 174
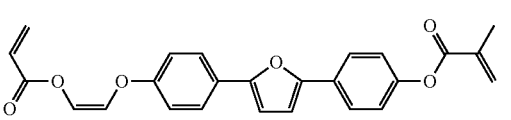
No. 175
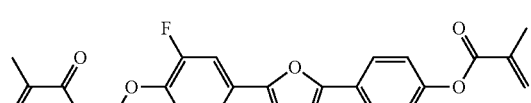
No. 176
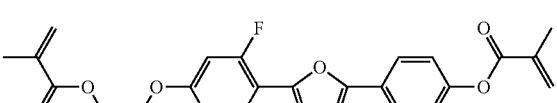
No. 177
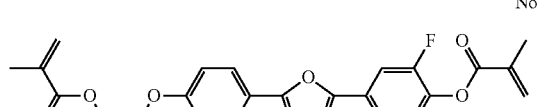
No. 178
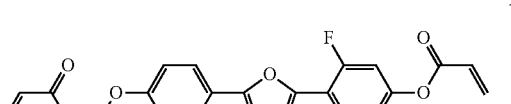
No. 179
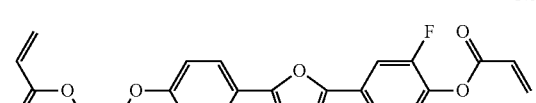
No. 180
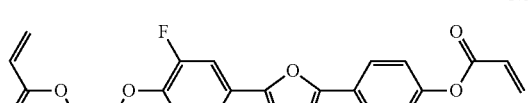
No. 181
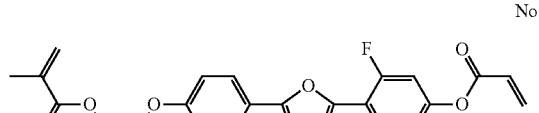
No. 182
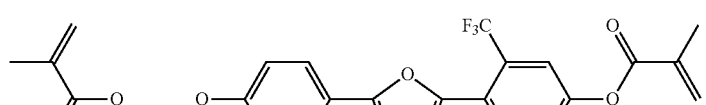
No. 183
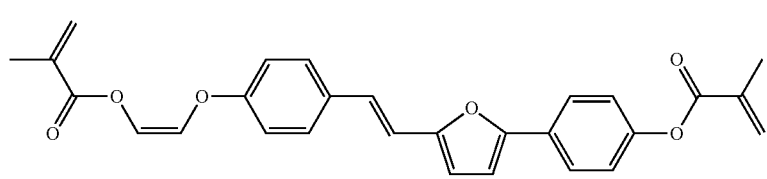
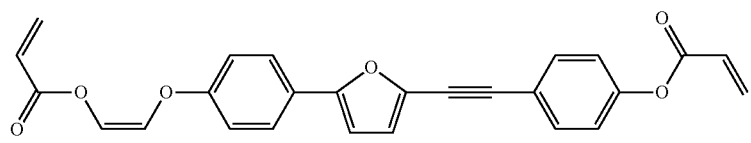

-continued
No. 184
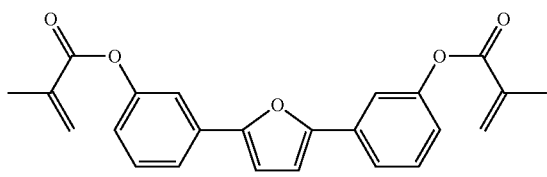
No. 185
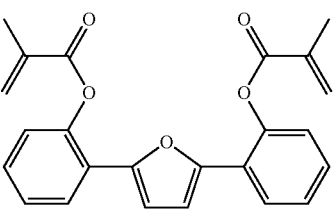
No. 186
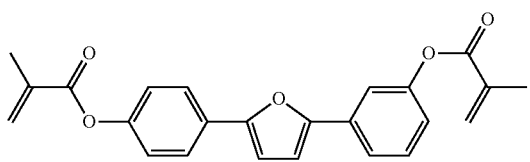
No. 187
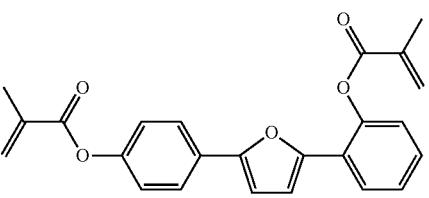
No. 188
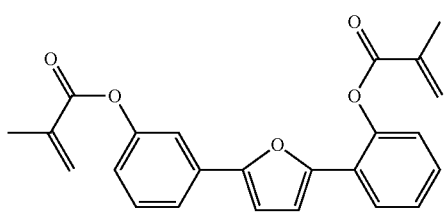
No. 189
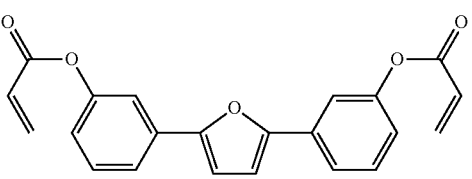
No. 190
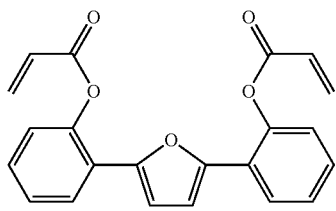
No. 191
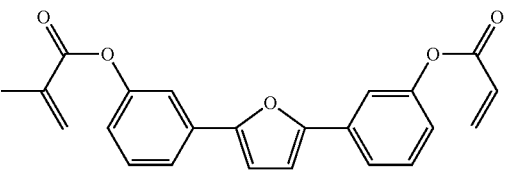
No. 192
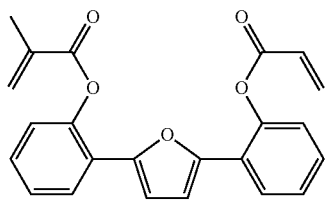
No. 193
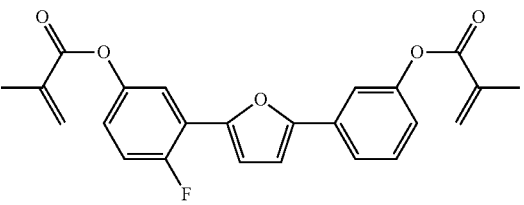
No. 194
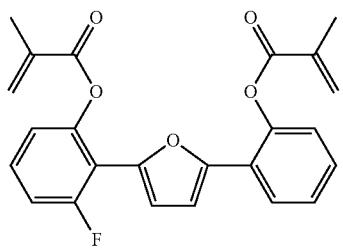
No. 195
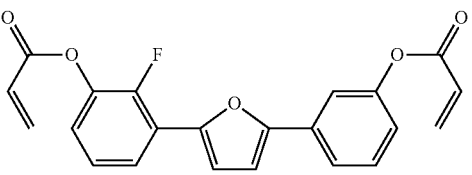
No. 196
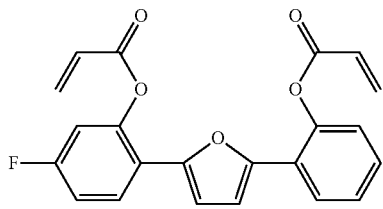
No. 197
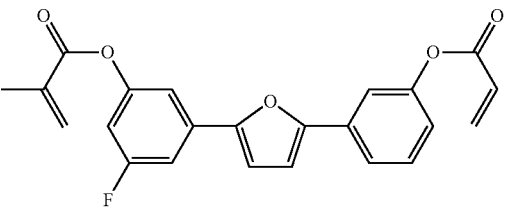

-continued
No. 198
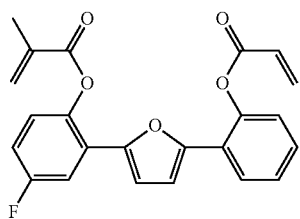
No. 199
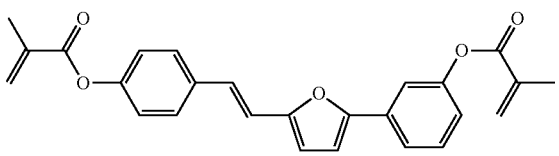
No. 200
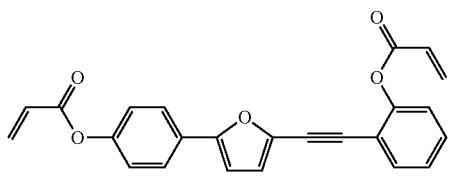
No. 201
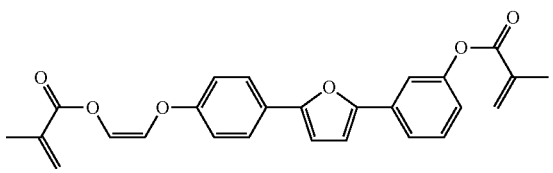
No. 202
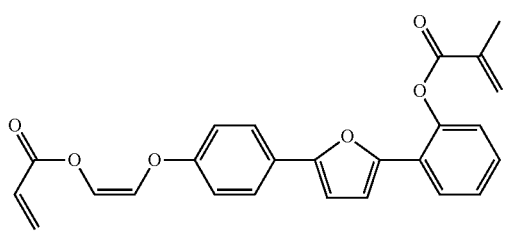
No. 203
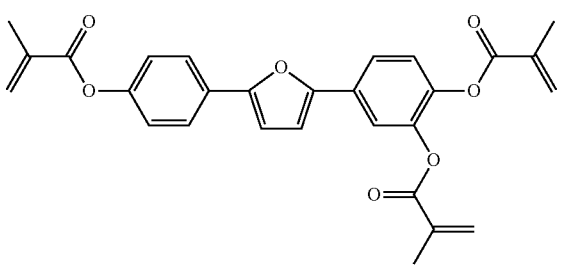
No. 204
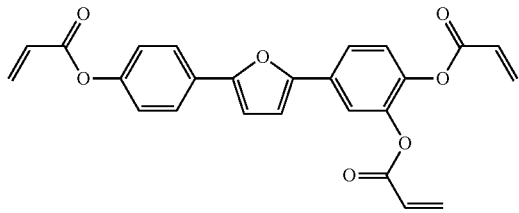
No. 205
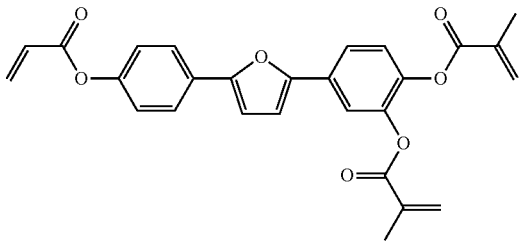
No. 206
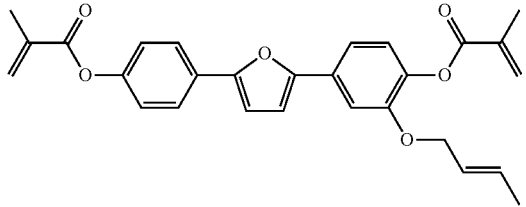
No. 207
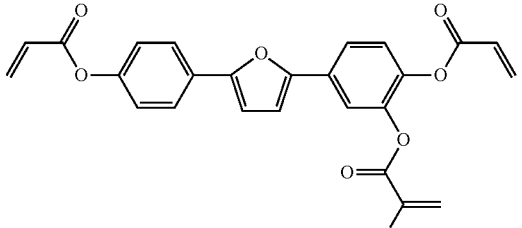
No. 208
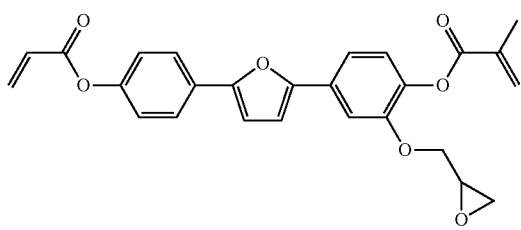
No. 209
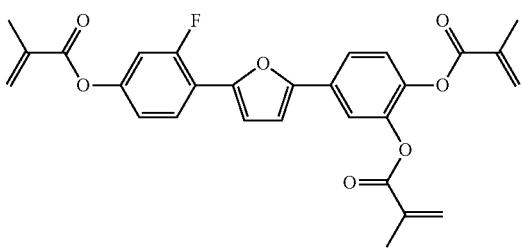

No. 210
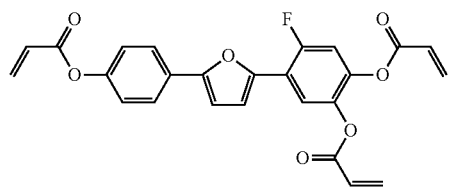
No. 211
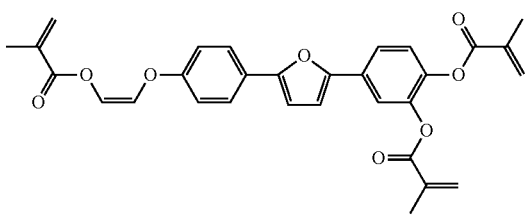
No. 212
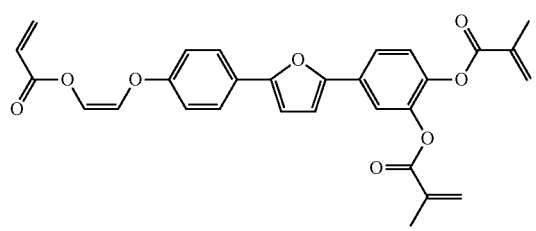
No. 213
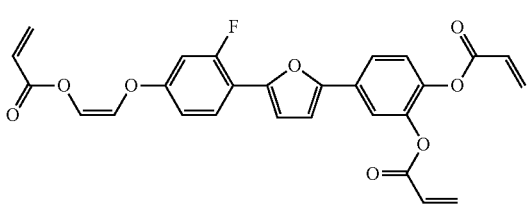
No. 214
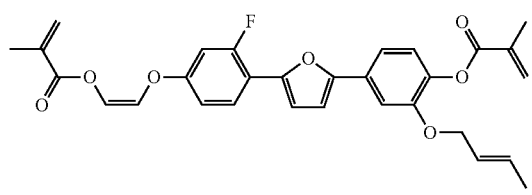
No. 215
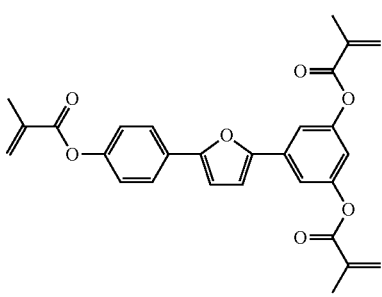
No. 216
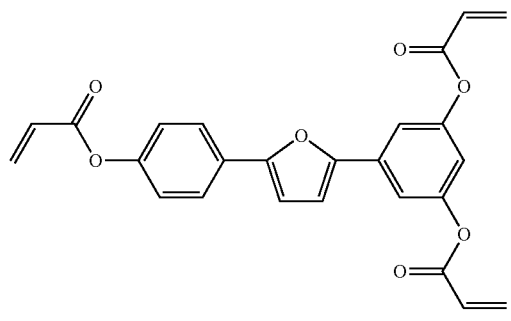
No. 217
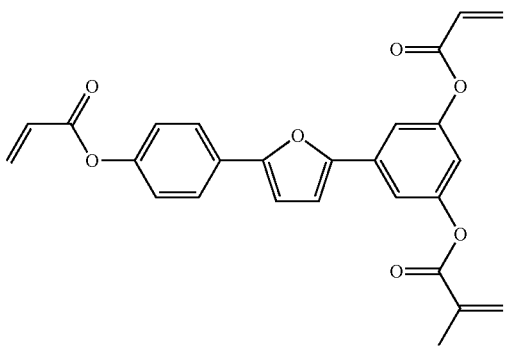
No. 218
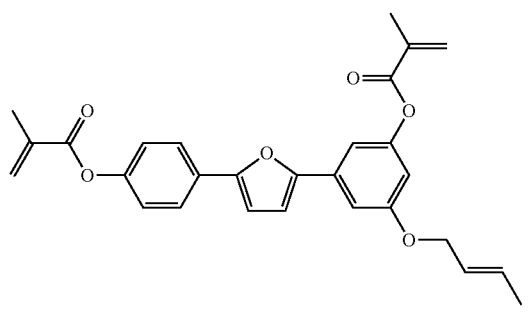
No. 219
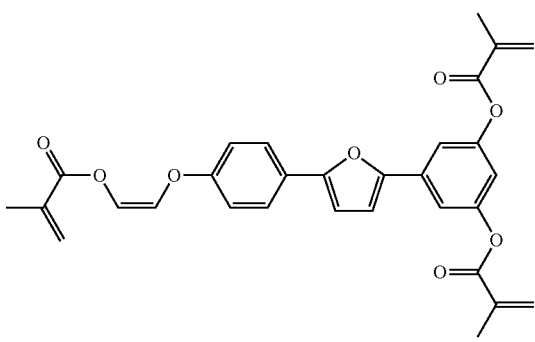

No. 220
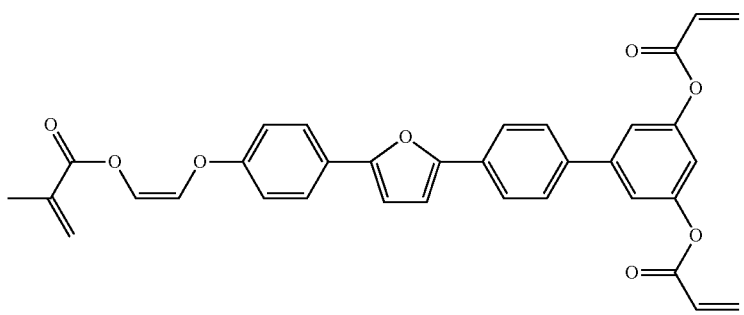
No. 221
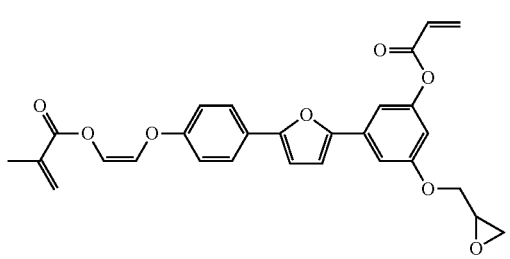
No. 222
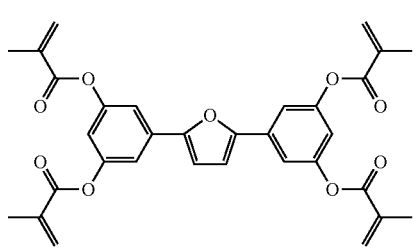
No. 223
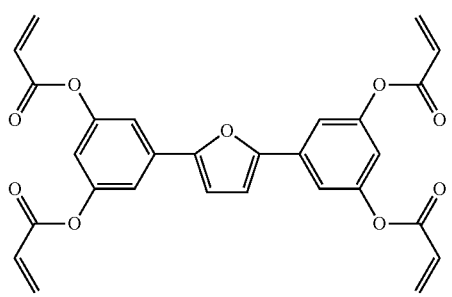
No. 224
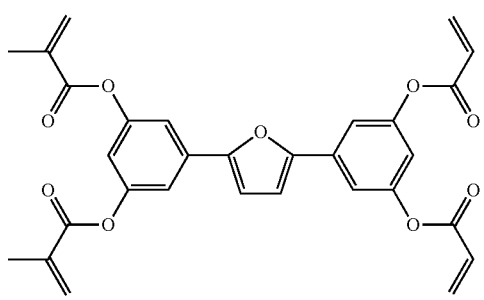
No. 225
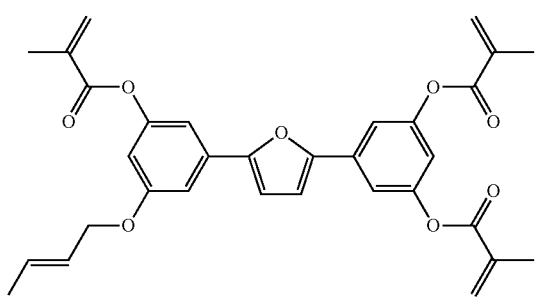
No. 226
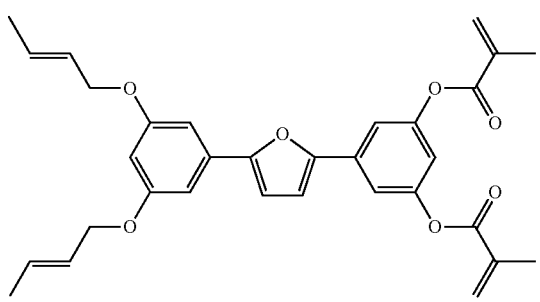
No. 227
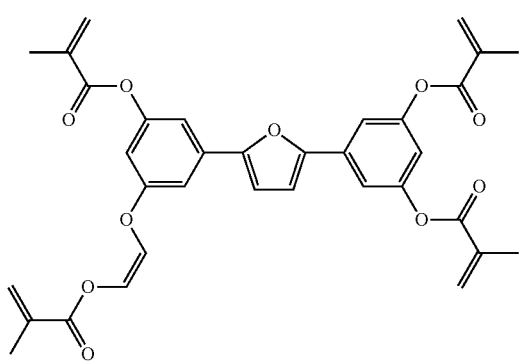
No. 228
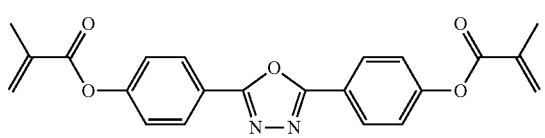

-continued
No. 229
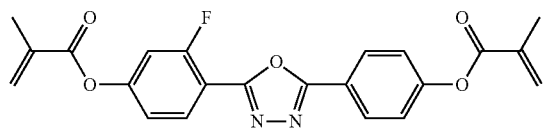
No. 230
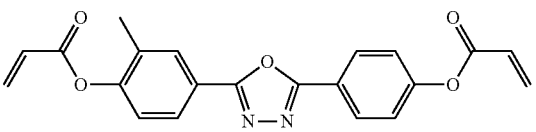
No. 231
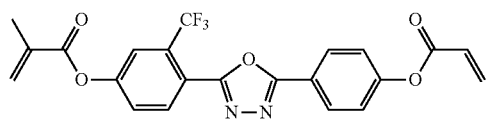
No. 232
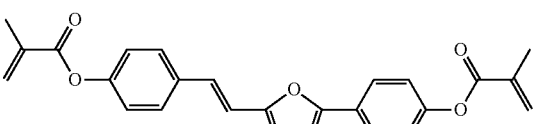
No. 233
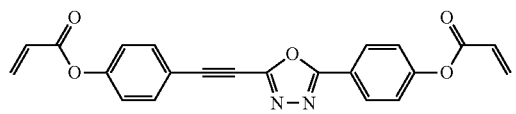
No. 234
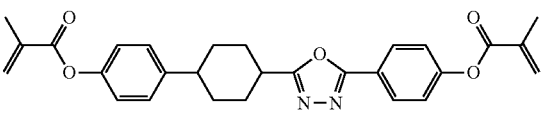
No. 235
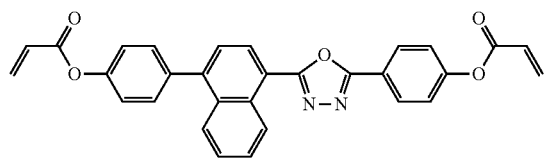
No. 236
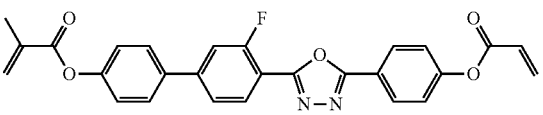
No. 237
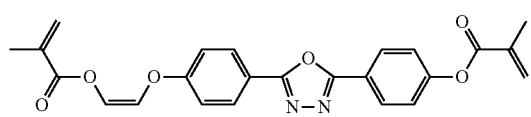
No. 238
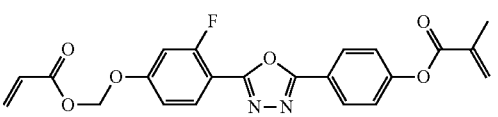
No. 239
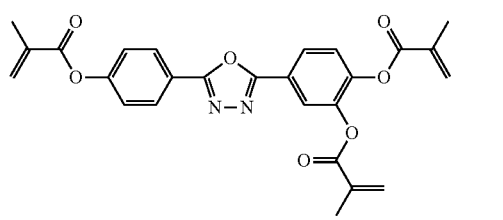
No. 240
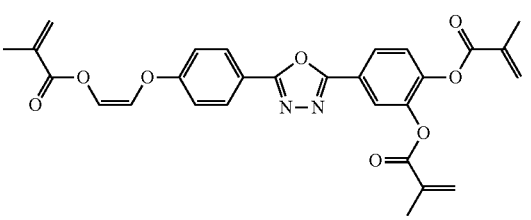
No. 241
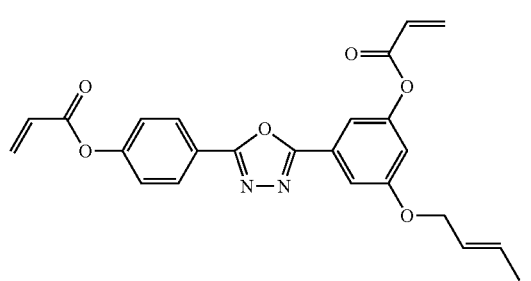
No. 242
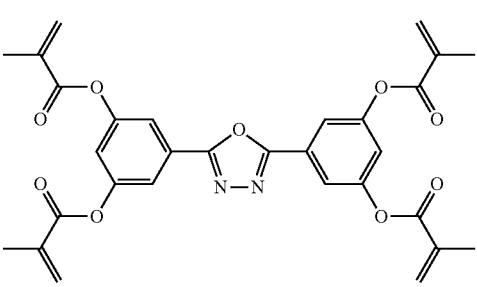

No. 243

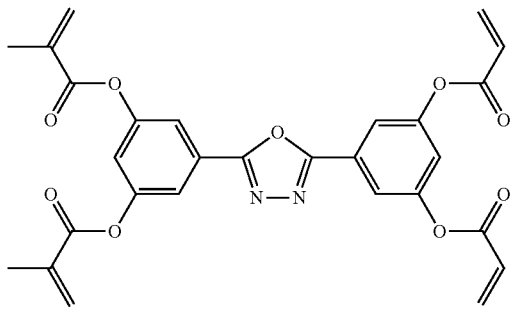

Comparative Example 1

For comparison, compound (R-1) was prepared according to a scheme described below.

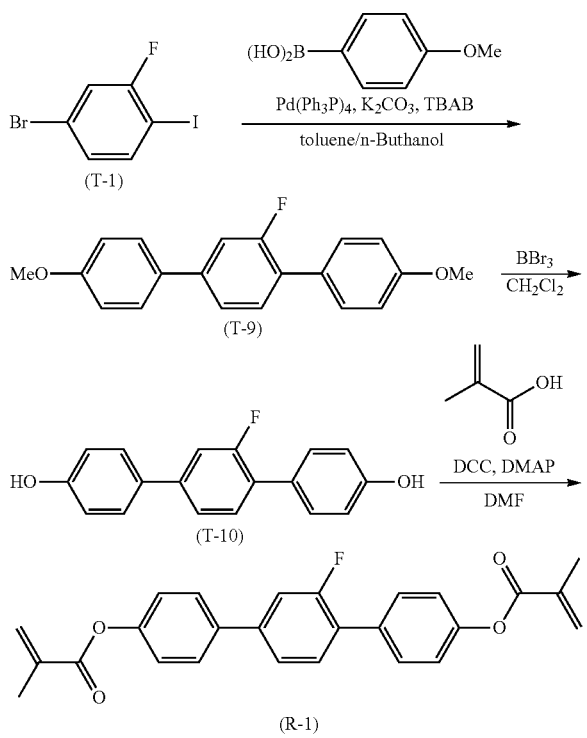

First Step: Synthesis of Compound (T-9)

To compound (T-1) (40.0 g, 0.133 mol), 4-methoxyphenyl-boronic acid (42.42 g, 0.279 mol), 5% Pd—C (1.2 g; made by N.E. Chemcat Corporation), tetrabutylammonium bromide (17.4 g, 0.054 mol) and potassium carbonate (73.49 g, 0.532 mol), a mixture: toluene:2-propanol:water=1:1:1 (volume ratio) (360 mL) was added, and then the resulting mixture was heated and refluxed. After 32 hours, Pd—C was filtrated off, and the resulting filtrate was extracted with toluene. The resulting extract was washed with saturated brine, and then dried and concentrated under reduced pressure. The resulting residue was purified by silica gel chromatography (toluene:ethyl acetate=19:1 in a volume ratio) to give compound (T-9; 3 g, 0.010 mol, yield: 7.3%) as a colorless crystal.

Second Step: Synthesis of Compound (T-10)

To a methylene chloride (100 mL) solution of compound (T-9) (8.62 g, 0.028 mol), boron tribromide (1.0 mol/L methylene chloride solution; 70.0 mL) was added dropwise at −20° C. or lower, and the resulting mixture was stirred at room temperature overnight. The resulting reaction mixture was poured into ice water (100 mL), and extracted with methylene chloride (100 mL). The resulting extract was washed with saturated brine, and then dried and concentrated under reduced pressure. The resulting residue was purified by silica gel chromatography (ethyl acetate) to give compound (T-10) (4.2 g, 0.015 mol, yield: 53.6%) as a brown crystal.

Third Step: Synthesis of (R-1)

Compound (T-10) (4.0 g, 0.014 mol) was subjected to reaction in a manner similar to the reaction in Example 1 to give comparative compound (R-1) as a colorless crystal (3.4 g, 0.008 mol, yield: 57.2%).

$^1$H-NMR (δ ppm; CDCl$_3$): 7.64-7.64 (m, 4H), 7.50 (dd, J=8.1, 8.0 Hz, 1H), 7.43 (dd, J=8.0, 1.7 Hz, 1H), 7.38 (dd, J=11.9, 1.7 Hz, 1H), 7.23 (d, J=8.5 Hz, 2H×2), 6.38 (s, 1H×2), 5.79-5.78 (m, 1H×2), 2.09 (s, 3H×2). $^{19}$F-NMR (δ ppm; CDCl$_3$): −118.10 (dd, J=11.9, 8.1 Hz, 1F).

Physical properties of comparative compound (R-1) were as described below. Melting point: 179.11° C., polymerization starting temperature: 184.15° C.

Comparative Experiment

Liquid crystal composition A described below was used for Comparative Experiment.

| | | |
|---|---|---|
| 3-H2B(2F,3F)-O2 | (6-4) | 18% |
| 5-H2B(2F,3F)-O2 | (6-4) | 17% |
| 3-HH1OCro(7F,8F)-5 | (10-6) | 6% |
| 3-HBB(2F,3F)-O2 | (7-7) | 10% |
| 4-HBB(2F,3F)-O2 | (7-7) | 6% |
| 5-HBB(2F,3F)-O2 | (7-7) | 6% |
| 2-HH-3 | (13-1) | 14% |
| 3-HH-4 | (13-1) | 8% |
| 3-HHB-1 | (14-1) | 5% |
| 3-HHB-3 | (14-1) | 6% |
| 3-HHB-O1 | (14-1) | 4% |

A polymerizable compound was added to liquid crystal composition A at a ratio of 0.3% by weight. The composition was irradiated with ultraviolet light having an intensity of 75 mW/cm$^2$ for 200 seconds (15,000 mJ). A mercury-xenon lamp EXECURE4000-D made by HOYA CANDEO OPTRONICS Corporation was used for irradiation with ultraviolet light. An amount of polymerizable compound remaining in the composition was measured by HPLC. The results obtained by irradiation with ultraviolet light for 400 seconds (30,000 mJ) were also summarized in Table 1. "Unreacted material" was expressed in terms of a ratio of the unreacted polymerizable compound based on the weight of the polymerizable compound added. Then, "2% or less" means incapability of detection of the unreacted polymerizable compound. Table 1 shows that the unreacted material was detected in comparative compound (R-1), but compound (No. 1) according to the invention was consumed by polymerization. Accordingly, the compound according to the invention can be concluded to be excellent from a viewpoint of high reactivity.

TABLE 1

Amount of unreacted polymerizable compound

| Polymerizable compound | Structural formula | Unreacted material (wt %) 15,000 mJ | Unreacted material (wt %) 30,000 mJ |
|---|---|---|---|
| Compound (No. 1) | (methacrylate–phenyl–furan–phenyl–methacrylate structure) | 2% or less | 2% or less |
| Comparative Compound (R-1) | (methacrylate–phenyl–fluorophenyl–phenyl–methacrylate structure) | 41% | 26% |

2. Examples of Polymerizable Compositions

Compounds described in Examples were expressed using symbols according to definitions in Table 2 below. In Table 2, a configuration of 1,4-cyclohexylene is trans. A parenthesized number next to a symbolized compound in Examples corresponds to the number of the compound. A symbol (-) means any other liquid crystal compound. A content (percentage) of a liquid crystal compound is expressed in terms of weight percentage (% by weight) based on the liquid crystal composition. Values of physical properties of the polymerizable composition were summarized in a last part. The physical properties were measured in accordance with the methods described above, and measured values were directly described without extrapolation.

TABLE 2

Method for Description of Compounds using Symbols
$R—(A_1)—Z_1—\ldots—Z_n—(A_n)—R'$

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |

| 2) Right-terminal Group —R' | Symbol |
|---|---|
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —CF=CH—$CF_3$ | —FVCF3 |
| —C≡N | —C |

| 3) Bonding Group —$Z_n$— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

| 4) Ring Structure —$A_n$— | Symbol |
|---|---|
| (cyclohexylene) | H |
| (phenylene) | B |
| (fluorophenylene) | B(F) |
| (2-fluorophenylene) | B(2F) |
| (difluorophenylene) | B(F,F) |
| (2,5-difluorophenylene) | B(2F,5F) |

TABLE 2-continued

Method for Description of Compounds using Symbols
R—(A$_1$)—Z$_1$— ... —Z$_n$—(A$_n$)—R'

| | |
|---|---|
| (difluorobenzene) | B(2F,3F) |
| (fluoro-chlorobenzene) | B(2F,3CL) |
| (1,3-dioxane) | G |
| (tetrahydropyran) | dh |
| (tetrahydropyran isomer) | Dh |
| (difluorochroman) | Cro(7F,8F) |

5) Examples of Description

Example 1  3-BB(F,F)XB(F,F)-F

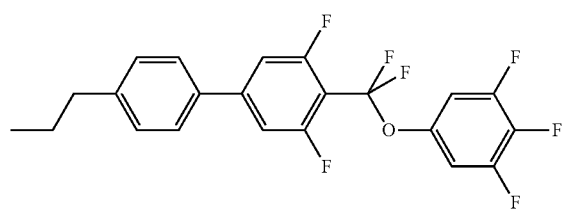

Example 2  3-HBB(2F,3F)-O2

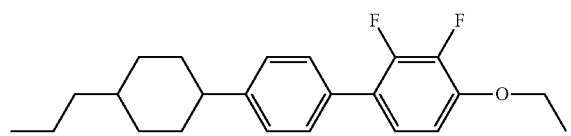

Example 3  3-HH-4

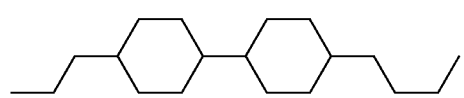

TABLE 2-continued

Method for Description of Compounds using Symbols
R—(A$_1$)—Z$_1$— ... —Z$_n$—(A$_n$)—R'

Example 4  3-HBB(F,F)-F

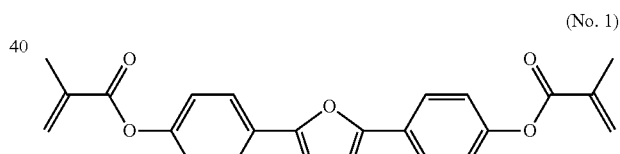

Use Example 1

| | | |
|---|---|---|
| 3-HB-O1 | (13-5) | 15% |
| 3-HH-4 | (13-1) | 2% |
| 3-HH-V | (13-1) | 3% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (14-1) | 6% |

To the composition described above, compound (No. 1) described below was added at a ratio of 0.3% by weight.

(No. 1)

NI=86.5° C.; Δn=0.090; Δ∈=−3.4; η=35.3 mPa·s.

Use Example 2

| | | |
|---|---|---|
| 2-HB-C | (5-1) | 5% |
| 3-HB-C | (5-1) | 12% |
| 3-HB-O2 | (13-5) | 18% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

To the composition described above, compound (No. 228) described below was added at a ratio of 0.25% by weight.

(No. 228)

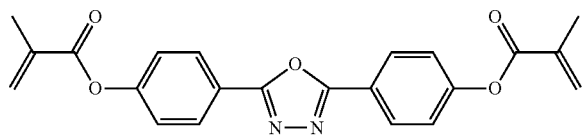

NI=100.7° C.; Δn=0.095; Δ∈=4.5; η=18.1 mPa·s.

Use Example 3

| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 3-HBB(2F,3F)-O2 | (7-7) | 12% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

To the composition described above, compound (No. 13) described below was added at a ratio of 0.2% by weight.

(No. 13)

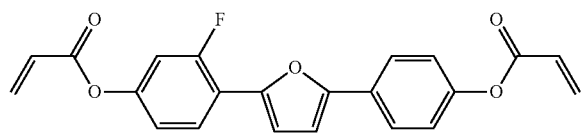 [SMILES: C=C(C)C(=O)Oc1ccc(-c2ccc(-c3ccc(OC(=O)C(=C)C)cc3)o2)cc1]

NI=76.5° C.; Δn=0.093; Δ∈=−4.1; η=19.4 mPa·s.

Use Example 4

| 2-HH-3 | (13-1) | 16% |
| 3-HH-V | (13-1) | 5% |
| 7-HB-1 | (13-5) | 5% |
| 5-HB-O2 | (13-5) | 8% |
| 3-HB(2F,3F)-O2 | (6-1) | 17% |
| 5-HB(2F,3F)-O2 | (6-1) | 16% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-6) | 5% |
| 5-HBB(F)B-2 | (15-5) | 10% |
| 5-HBB(F)B-3 | (15-5) | 10% |

To the composition described above, compound (No. 163) described below was added at a ratio of 0.3% by weight.

(No. 163)

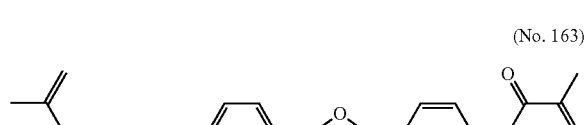

NI=78.1° C.; Δn=0.103; Δ∈=−2.5; η=22.0 mPa·s.

Use Example 5

| 5-HB-CL | (2-2) | 13% |
| 3-HH-4 | (13-1) | 12% |
| 3-HH-5 | (13-1) | 7% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

To the composition described above, compound (No. 205) described below was added at a ratio of 0.2% by weight.

(No. 205)

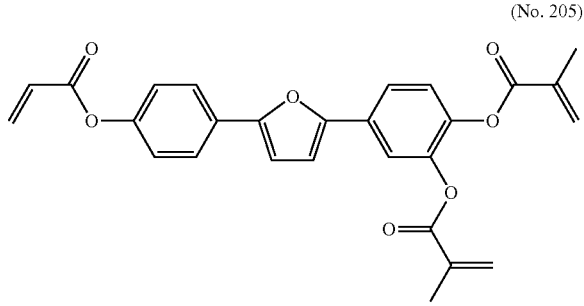 [SMILES: C=CC(=O)Oc1ccc(-c2ccc(-c3ccc(OC(=O)C(=C)C)c(OC(=O)C(=C)C)c3)o2)cc1]

NI=117.3° C.; Δn=0.090; Δ∈=3.6; η=19.3 mPa·s.

Use Example 6

| 5-HB-CL | (2-2) | 11% |
| 3-HH-4 | (13-1) | 8% |
| 3-HHB-1 | (14-1) | 8% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 3% |

To the composition described above, compound (No. 1) described below was added at a ratio of 0.4% by weight.

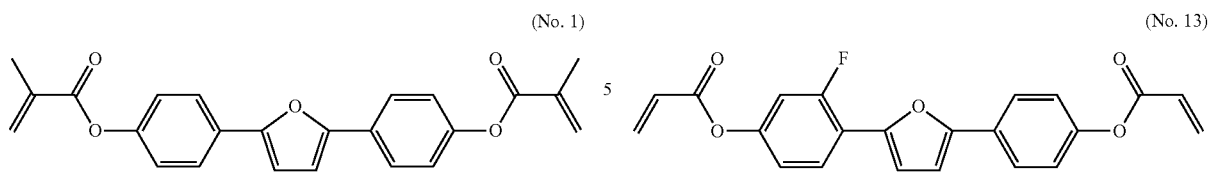

(No. 1)

NI=79.3° C.; Δn=0.102; Δ∈=8.4; η=20.9 mPa·s.

Use Example 7

| | | |
|---|---|---|
| 5-HB-CL | (2-2) | 15% |
| 7-HB(F,F)-F | (2-4) | 3% |
| 3-HH-4 | (13-1) | 10% |
| 3-HH-5 | (13-1) | 5% |
| 3-HB-O2 | (13-5) | 15% |
| 3-HHB-1 | (14-1) | 8% |
| 3-HHB-O1 | (14-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 7% |
| 4-H2HB(F,F)-F | (3-15) | 5% |

To the composition described above, compound (No. 228) described below was added at a ratio of 0.35% by weight.

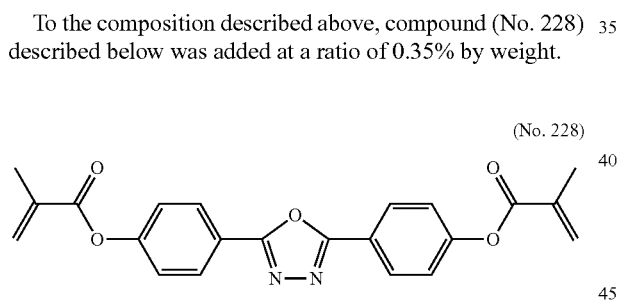

(No. 228)

NI=72.3° C.; Δn=0.074; Δ∈=2.9; η=14.3 mPa·s.

Use Example 8

| | | |
|---|---|---|
| 5-HB-CL | (2-2) | 6% |
| 7-HB(F)-F | (2-3) | 4% |
| 3-HH-4 | (13-1) | 9% |
| 3-HH-EMe | (13-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

To the composition described above, compound (No. 13) described below was added at a ratio of 0.15% by weight.

(No. 13)

NI=80.9° C.; Δn=0.066; Δ∈=5.7; η=19.9 mPa·s.

Use Example 9

| | | |
|---|---|---|
| 1-BB-3 | (13-8) | 10% |
| 3-HH-V | (13-1) | 26% |
| 3-HB-O2 | (13-5) | 3% |
| 3-BB(2F,3F)-O2 | (6-3) | 13% |
| 2-HH1OB(2F,3F)-O2 | (7-5) | 14% |
| 3-HH1OB(2F,3F)-O2 | (7-5) | 20% |
| 3-HHB-1 | (14-1) | 8% |
| 5-B(F)BB-2 | (14-8) | 6% |

To the composition described above, compound (No. 164) described below was added at a ratio of 0.25% by weight.

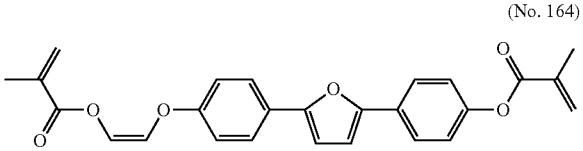 [SMILES: C=C(C)C(=O)O/C=C\Oc1ccc(-c2ccc(-c3ccc(OC(=O)C(=C)C)cc3)o2)cc1]

(No. 164)

NI=74.3° C.; Δn=0.108; Δ∈=−3.1; η=15.4 mPa·s.

Use Example 10

| | | |
|---|---|---|
| 3-GB(F)B(F,F)XB(F,F)-F | (4-57) | 5% |
| 5-HB(F)B(F,F)XB(F,F)-F | (4-41) | 3% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 3% |
| 3-GB(F,F)XB(F,F)-F | (3-113) | 5% |
| 3-HHBB(F,F)-F | (4-6) | 3% |

To the composition described above, compound (No. 222) described below was added at a ratio of 0.3% by weight.

(No. 222)

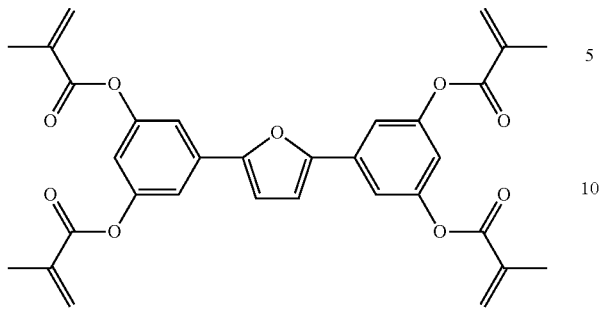

NI=84.4° C.; Δn=0.104; Δ∈=7.4; η=13.5 mPa·s.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal display device having a mode such as PSA can be produced by polymerizing a polymerizable composition containing compound (1) and a liquid crystal composition. The polymerizable compound can also be used as a raw material of an optical isotropic body.

What is claimed is:
1. A compound represented by formula (1):

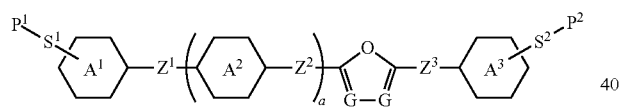

(1)

wherein, in formula (1),
$P^1$ and $P^2$ are independently a polymerizable group;
$S^1$ and $S^2$ are independently a single bond or alkylene having 1 to 6 carbons, and in the alkylene, at least one of —$CH_2$— may be replaced by —O—, —COO—, —OCO—, —CH=CH— or —C≡C—; wherein both G are —CH= or —N=, wherein when one G is —CH=, the other G is —CH=, and wherein one G is —N=, the other G is —N=;
wherein when both G are —CH=, ring $A^1$, ring $A^2$ and ring $A^3$ are independently cyclohexylene, cyclohexenylene, phenylene, naphthylene, anthracenylene, tetrahydropyranylene, dioxanylene, pyrimidinylene or pyridinylene, and in the groups, at least one of hydrogen may be replaced by halogen, alkyl having 1 to 12 carbons, alkoxy having 1 to 12 carbons, alkyl having 1 to 12 carbons in which at least one of hydrogen is replaced by halogen, or alkoxy having 1 to 12 carbons in which at least one of hydrogen is replaced by halogen, one or two of hydrogen may be replaced by —$S^3$—$P^3$, $P^3$ is defined herein in a manner identical with the definition of $P^1$ or $P^2$, and $S^3$ is defined in a manner identical with the definition of $S^1$ or $S^2$;
wherein when both G are —N=, ring $A^1$, ring $A^2$ and ring $A^3$ are independently cyclohexylene, cyclohexenylene, phenylene, naphthylene, anthracenylene, tetrahydropyranylene, or dioxanylene, and in the groups, at least one of hydrogen may be replaced by halogen, alkyl having 1 to 12 carbons, alkoxy having 1 to 12 carbons, alkyl having 1 to 12 carbons in which at least one of hydrogen is replaced by halogen, or alkoxy having 1 to 12 carbons in which at least one of hydrogen is replaced by halogen, one or two of hydrogen may be replaced by —$S^3$—$P^3$, $P^3$ is defined herein in a manner identical with the definition of $P^1$ or $P^2$, and $S^3$ is defined in a manner identical with the definition of $S^1$ or $S^2$;
wherein when both G are —CH=, $Z^1$, $Z^2$ and $Z^3$ are independently a single bond, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—C($CH_3$)=CH—, —C($CH_3$)=C($CH_3$)—COO—, —OCO—C($CH_3$)=C($CH_3$)—, —C≡C—, —COCH=CH—, —CH=CHCO—, —C($CH_3$)=C($CH_3$)—, —CH=CH—$CH_2$O—, —O$CH_2$—CH=CH—, —CH=CH—O$CH_2$—, —$CH_2$O—CH=CH— or —CO—;
wherein when both G are —N=, $Z^1$ is a single bond, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—C($CH_3$)=CH—, —C($CH_3$)=C($CH_3$)—COO—, —OCO—C($CH_3$)=C($CH_3$)—, —C≡C—, —COCH=CH—, —CH=CHCO—, —C($CH_3$)=C($CH_3$)—, —CH=CH—$CH_2$O—, —O$CH_2$—CH=CH—, —CH=CH—O$CH_2$—, —$CH_2$O—CH=CH—, or —CO—; $Z^2$ is a single bond, —COO—, —OCO—, —CH=CH—COO—, —C($CH_3$)=CH—COO—, —CH=C($CH_3$)—COO—, —C($CH_3$)=C($CH_3$)—COO—, —C≡C—, —CH=CHCO—, —CH=CH—$CH_2$O—, —CH=CH—O$CH_2$—, or —CO—; $Z^3$ is a single bond, —COO—, —OCO—, —OCO—CH=CH—, —OCO—CH=C($CH_3$)—, —OCO—C($CH_3$)=CH—, —OCO—C($CH_3$)=C($CH_3$)—, —C≡C—, —COCH=CH—, —O$CH_2$—CH=CH—, —$CH_2$O—CH=CH—, or —CO—;
and a is 0 or 1.

2. The compound according to claim 1, wherein, in formula (1) according to claim 1, $P^1$, $P^2$ and $P^3$ are a group represented by formula (P-1):

wherein, in formula (P-1), M is hydrogen, fluorine, —$CH_3$ or —$CF_3$.

3. The compound according to claim 1, represented by any one of formulas (1-1) to (1-6):

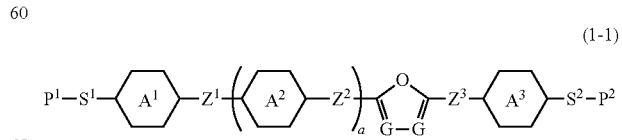

(1-1)

-continued

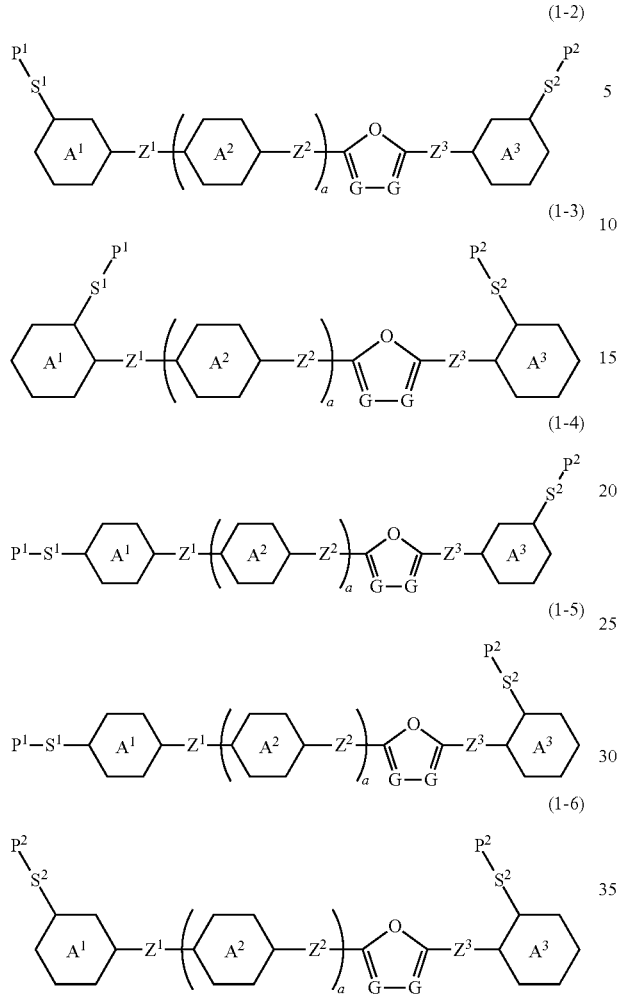

wherein, in formulas (1-1) to (1-6),
$P^1$ and $P^2$ are independently a group represented by formula (P-1):

—OCO-(M)C=CH$_2$ (P-1)

wherein, in group (P-1), M is hydrogen, fluorine, —CH$_3$ or —CF$_3$;
$S^1$ and $S^2$ are independently a single bond, —CH$_2$O—, —OCH$_2$—, —COO—, —OCO—, —CH=CH—, —CH$_2$CH$_2$O—, —OCH$_2$CH$_2$—, —CH=CHO—, —OCH=CH— or —C≡C—;
wherein both G are —CH= or —N=, wherein when one G is —CH=, the other G is —CH=, and wherein when one G is —N=, the other G is —N=;
ring $A^1$, ring $A^2$ and ring $A^3$ are independently cyclohexylene, cyclohexenylene or phenylene, and in the groups, at least one of hydrogen may be replaced by fluorine, alkyl having 1 to 10 carbons, alkoxy having 1 to 10 carbons, alkyl having 1 to 10 carbons in which at least one of hydrogen is replaced by halogen, or alkoxy having 1 to 10 carbons in which at least one of hydrogen is replaced by halogen, one or two of hydrogen may be replaced by —S$^3$—P$^3$, P$^3$ is defined herein in a manner identical with the definition of P$^1$ or P$^2$, and S$^3$ is defined in a manner identical with the definition of S$^1$ or S$^2$;

wherein when both G are —CH=, $Z^1$, $Z^2$ and $Z^3$ are independently a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH— or —CO—;
wherein when both G are —N=, $Z^1$ is a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH—, or —CO—; $Z^2$ is a single bond, —COO—, —OCO—, —CH=CH—COO—, —C(CH$_3$)=CH—COO—, —CH=C(CH$_3$)—COO—, —C(CH$_3$)=C(CH$_3$)—COO—, —C≡C—, —CH=CHCO—, —CH=CH—CH$_2$O—, —CH=CH—OCH$_2$—, or —CO—; $Z^3$ is a single bond, —COO—, —OCO—, —OCO—CH=CH—, —OCO—CH=C(CH$_3$)—, —OCO—C(CH$_3$)=CH—, —OCO—C(CH$_3$)=C(CH$_3$)—, —C≡C—, —COCH=CH—, —OCH$_2$—CH=CH—, —CH$_2$O—CH=CH—, or —CO—;
and a is 0 or 1.

4. The compound according to claim 3, wherein a is 0; wherein when both G are —N=, $Z^1$ is a single bond, —COO—, —OCO—, —CH=CH—COO—, —C(CH$_3$)=CH—COO—, —CH=C(CH$_3$)—COO—, —C(CH$_3$)=C(CH$_3$)—COO—, —C≡C—, —CH=CHCO—, —CH=CH—CH$_2$O—, —CH=CH—OCH$_2$—, or —CO— in formulas (1-1) to (1-6) according to claim 3.

5. The compound according to claim 1, represented by any of formulas (1-a) to (1-f):

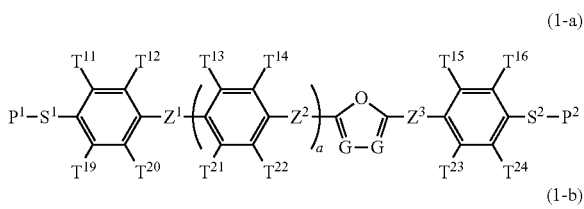

(1-a)

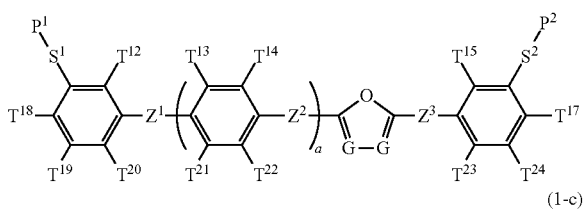

(1-b)

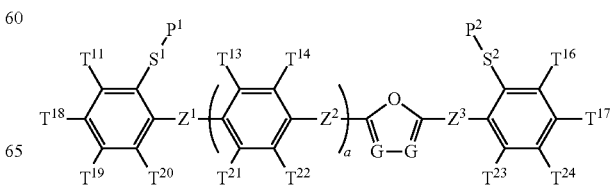

(1-c)

-continued

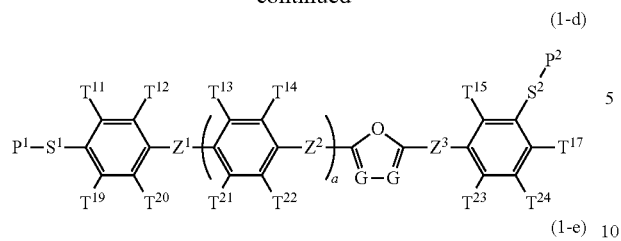
(1-d)

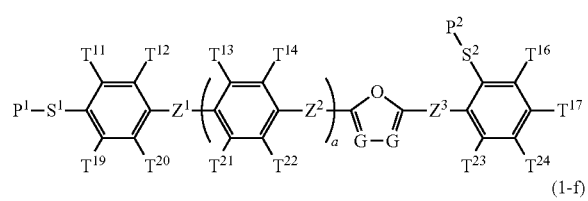
(1-e)

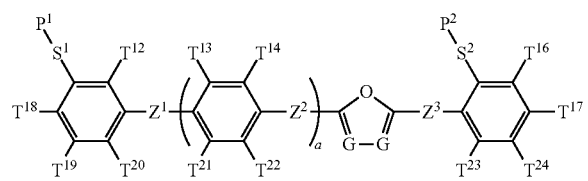
(1-f)

wherein, in formulas (1-a) to (1-f),
P$^1$ and P$^2$ are independently a group represented by formula (P-1):

—OCO-(M)C=CH$_2$     (P-1)

wherein, in formula (P-1), M is hydrogen, fluorine, —CH$_3$ or —CF$_3$:
wherein both G are —CH= or —N=, wherein when one G is —CH=, the other G is —CH=, and wherein when one G is —N=, the other G is —N=;
S$^1$ and S$^2$ are independently a single bond, —CH$_2$O—, —OCH$_2$—, —COO—, —OCO—, —CH=CH—, —CH$_2$CH$_2$O—, —OCH$_2$CH$_2$—, —CH=CHO—, —OCH=CH— or —C≡C—; two of G are —CH= or —N=;
T$^{11}$, T$^{12}$, T$^{13}$, T$^{14}$, T$^{15}$, T$^{16}$, T$^{17}$, T$^{18}$, T$^{19}$, T$^{20}$, T$^{21}$, T$^{22}$, T$^{23}$ and T$^{24}$ are independently hydrogen, fluorine, —CH$_3$, —CHF$_2$ or —CF$_3$;
wherein when both G are —CH=, Z$^1$, Z$^2$ and Z$^3$ are independently a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH— or —CO—
wherein when both G are —N=, Z$^1$ is a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)—, —C≡C—, —COCH=CH—, —CH=CHCO—, —C(CH$_3$)=C(CH$_3$)—, —CH=CH—CH$_2$O—, —OCH$_2$—CH=CH—, —CH=CH—OCH$_2$—, —CH$_2$O—CH=CH—, or —CO—; Z$^2$ is a single bond, —COO—, —OCO—, —CH=CH—COO—, —C(CH$_3$)=CH—COO—, —CH=C(CH$_3$)—COO—, —C(CH$_3$)=C(CH$_3$)—COO—, —C≡C—, —CH=CHCO—, —CH=CH—CH$_2$O—, —CH=CH—OCH$_2$—, or —CO—; Z$^3$ is a single bond, —COO—, —OCO—, —OCO—CH=CH—, —OCO—CH=C(CH$_3$)—, —OCO—C(CH$_3$)=CH—, —OCO—C(CH$_3$)=C(CH$_3$)—, —C≡C—, —COCH=CH—, —OCH$_2$—CH=CH—, —CH$_2$O—CH=CH—, or —CO—; and a is 0 or 1.

6. The compound according to claim 5, wherein a is 0; wherein when both G are —N=, Z$^1$ is a single bond, —COO—, —OCO—, —CH=CH—COO—, —C(CH$_3$)=CH—COO—, —CH=C(CH$_3$)—COO—, —C(CH$_3$)=C(CH$_3$)—COO—, —C≡C—, —CH=CHCO—, —CH=CH—CH$_2$O—, —CH=CH—OCH$_2$—, or —CO— in formulas (1-a) to (1-f) according to claim 5.

7. The compound according to claim 5, wherein, in formulas (1-a) to (1-f) according to claim 5, P$^1$ and P$^2$ are independently —OCO—CH=CH$_2$ or —OCO—(CH$_3$)C=CH$_2$; S$^1$ and S$^2$ are independently a single bond, —CH$_2$O—, —OCH$_2$—, —CH$_2$CH$_2$O—, —OCH$_2$CH$_2$—, —CH=CHO— or —OCH=CH—; wherein both G are —CH= or —N=, wherein when one G is —CH=, the other G is —CH=, and wherein one G is —N=, the other G is —N=; T$^{11}$, T$^{12}$, T$^{13}$, T$^{14}$, T$^{15}$, T$^{16}$, T$^{17}$, T$^{18}$, T$^{19}$, T$^{20}$, T$^{21}$, T$^{22}$, T$^{23}$ and T$^{24}$ are independently hydrogen or fluorine; wherein when both G are —CH=, Z$^1$ and Z$^3$ are a single bond, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—C(CH$_3$)=CH—, —C(CH$_3$)=C(CH$_3$)—COO—, —OCO—C(CH$_3$)=C(CH$_3$)— or —C≡C—; wherein when both G are —N=, Z$^1$ is a single bond, —COO—, —OCO—, —CH=CH—COO—, —C(CH$_3$)=CH—COO—, —CH=C(CH$_3$)—COO—, —C(CH$_3$)=C(CH$_3$)—COO—, or —C≡C—; when both G are —N=, Z$^3$ is a single bond, —COO—, —OCO—, —OCO—CH=CH—, —OCO—CH=C(CH$_3$)—, —OCO—C(CH$_3$)=CH—, —OCO—C(CH$_3$)=C(CH$_3$)—, or —C≡C—; and a is 0.

8. The compound according to claim 5, wherein, in formula (1-a) according to claim 5, P$^1$ and P$^2$ are independently —OCO—CH=CH$_2$ or —OCO—(CH$_3$)C=CH$_2$; S$^1$ and S$^2$ are a single bond; wherein both G are —CH= or —N=, wherein when one G is —CH=, the other G is —CH=, and wherein one G is —N=, the other G is —N=; T$^{11}$, T$^{12}$, T$^{15}$, T$^{16}$, T$^{19}$, T$^{20}$, T$^{23}$ and T$^{24}$ are hydrogen; Z$^1$ and Z$^3$ are a single bond; and a is 0.

9. A polymerizable composition, comprising at least one compound according to claim 1.

10. The polymerizable composition according to claim 9, further comprising at least one compound selected from the group of compounds represented by formulas (2) to (4):

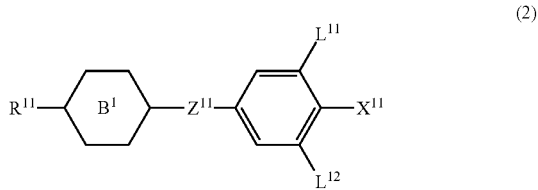
(2)

-continued

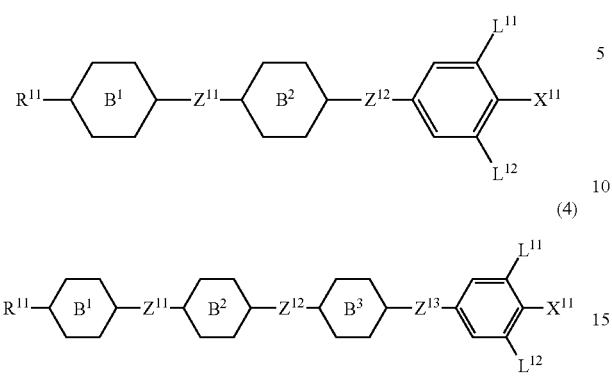

wherein, in formulas (2) to (4),

R$^{11}$ is alkyl having 1 to 10 carbons or alkenyl having 2 to 10 carbons, and in the alkyl and the alkenyl, at least one of —CH$_2$— may be replaced by —O—, and in the groups, at least one of hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring B$^1$, ring B$^2$ and ring B$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

Z$^{11}$, Z$^{12}$ and Z$^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine.

11. The polymerizable composition according to claim 9, further comprising at least one compound selected from the group of compounds represented by formula (5):

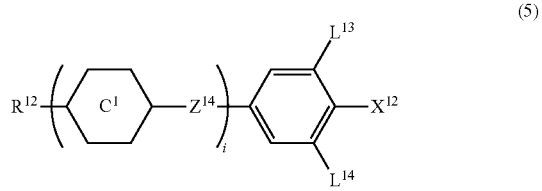

wherein, in formula (5),

R$^{12}$ is alkyl having 1 to 10 carbons or alkenyl having 2 to 10 carbons, and in the alkyl and the alkenyl, at least one of —CH$_2$— may be replaced by —O—, and in the groups, at least one of hydrogen may be replaced by fluorine;

X$^{12}$ is —C≡N or —C≡C—C≡N;

ring C$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

Z$^{14}$ is a single bond, —CH$_2$CH$_2$—, —C≡C—, —COO—, —CF$_2$O—, —OCF$_2$— or —CH$_2$O—;

L$^{13}$ and L$^{14}$ are independently hydrogen or fluorine; and i is 1, 2, 3 or 4.

12. The polymerizable composition according to claim 9, further comprising at least one compound selected from the group of compounds represented by formulas (6) to (12):

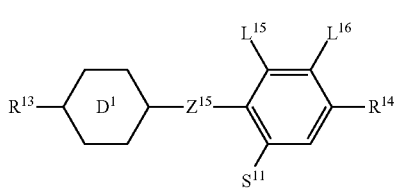

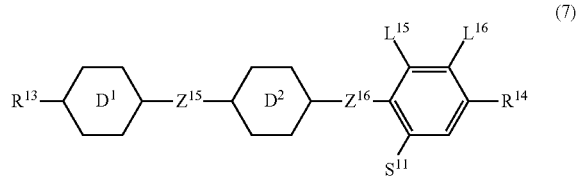

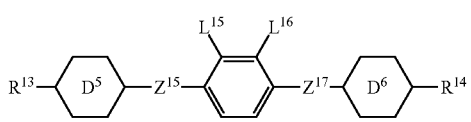

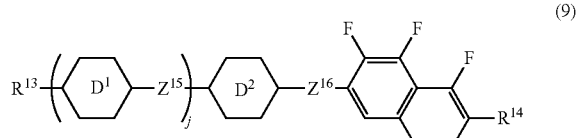

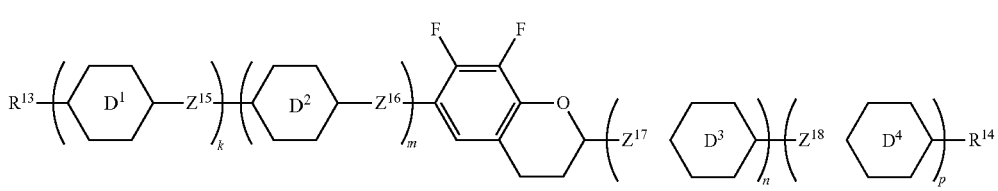

-continued

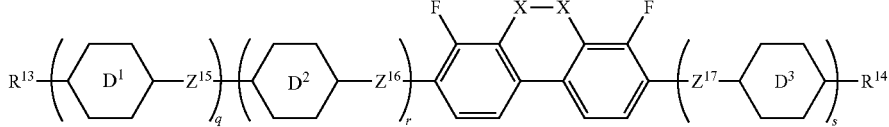
(11)

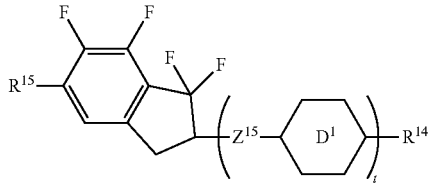
(12)

wherein, in formulas (6) to (12),
$R^{13}$ and $R^{14}$ are independently alkyl having 1 to 10 carbons or alkenyl having 2 to 10 carbons, and in the alkyl and the alkenyl, at least one of —$CH_2$— may be replaced by —O—, and in the groups, at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and in the groups, at least one of hydrogen may be replaced by fluorine;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or —$CH_3$;

X is —CHF— or —$CF_2$—; and j, k, m, n, p, q, r and s are independently 0 or 1, a sum of k, m, n, and p is 1 or 2, a sum of q, r, and s is 0, 1, 2 or 3, and t is 1, 2 or 3.

13. The polymerizable composition according to claim 9, further comprising at least one compound selected from the group of compounds represented by formulas (13) to (15):

(13)

-continued

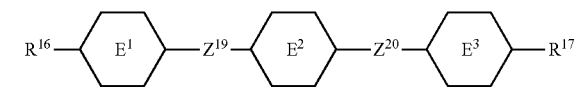
(14)

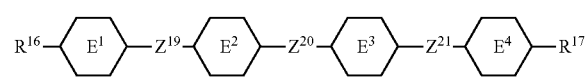
(15)

wherein, in formulas (13) to (15),
$R^{16}$ and $R^{17}$ are independently alkyl having 1 to 10 carbons or alkenyl having 2 to 10 carbons, and in the alkyl or the alkenyl, at least one of —$CH_2$— may be replaced by —O—, and in the groups, at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene, or pyrimidine-2,5-diyl; and $Z^{19}$, $Z^{20}$ and $Z^{21}$ are independently a single bond, —$CH_2CH_2$—, —CH=CH—, —C≡C—, or —COO—.

14. A liquid crystal composite, formed by polymerization of the polymerizable composition according to claim 9.

15. An optical isotropic body, formed by polymerization of the polymerizable composition according to claim 9.

16. A liquid crystal display device, comprising the polymerizable composition according to claim 9.

17. A liquid crystal display system, comprising the compound according to claim 1 in a liquid crystal display device.

* * * * *